US010087213B2

(12) United States Patent
Chen et al.

(10) Patent No.: US 10,087,213 B2
(45) Date of Patent: Oct. 2, 2018

(54) INTEIN MEDIATED PURIFICATION OF PROTEIN

(71) Applicant: THE TEXAS A&M UNIVERSITY SYSTEM, College Station, TX (US)

(72) Inventors: Zhilei Chen, College Station, TX (US); Miguel A. Ramirez, Dunedin (NZ); Dongli Guan, College Station, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 0 days.

(21) Appl. No.: 14/760,392

(22) PCT Filed: Jan. 10, 2014

(86) PCT No.: PCT/US2014/011076
§ 371 (c)(1),
(2) Date: Jul. 10, 2015

(87) PCT Pub. No.: WO2014/110393
PCT Pub. Date: Jul. 17, 2014

(65) Prior Publication Data
US 2015/0353597 A1 Dec. 10, 2015

Related U.S. Application Data

(60) Provisional application No. 61/751,735, filed on Jan. 11, 2013.

(51) Int. Cl.
*C07K 1/14* (2006.01)
*C12N 9/16* (2006.01)
*C07K 1/22* (2006.01)
*C07K 1/32* (2006.01)

(52) U.S. Cl.
CPC .......... *C07K 1/14* (2013.01); *C07K 1/22* (2013.01); *C07K 1/32* (2013.01); *C12N 9/16* (2013.01); *C07K 2319/20* (2013.01); *C07K 2319/92* (2013.01); *C12Y 301/00* (2013.01)

(58) Field of Classification Search
None
See application file for complete search history.

(56) References Cited

U.S. PATENT DOCUMENTS

2006/0141570 A1    6/2006    Wood et al.

FOREIGN PATENT DOCUMENTS

| EP | 1117693 | | 7/2001 |
|---|---|---|---|
| EP | 1151117 | | 7/2001 |
| EP | 1642980 | A1 | 4/2006 |
| JP | 2004-535802 | A | 12/2004 |
| WO | 2000018881 | A2 | 4/2000 |
| WO | 2000047751 | | 8/2000 |
| WO | WO02095036 | * | 11/2002 |
| WO | 2012100176 | A2 | 7/2012 |
| WO | 2014110393 | A1 | 7/2014 |

OTHER PUBLICATIONS

Al-Ali et al. Bioconjugate Chem., 2007, 18 (4), pp. 1294-1302.*
Singh et al. Curr Protein Pept Sci. 2017, 18, 1-11.*
Ramirez et al. Protein Engineering, Design and Selection, vol. 26, Issue 3, Mar. 1, 2013, pp. 215-223, published online Dec. 4, 2012.*
Amitai, et al. "Modulation of intein activity by its neighboring extein substrates" (Jul. 2009) Proc Natl Acad Sci U S A, 106, 11005-11010.
Banki, et al. "Inteins and Affinity Resin Substitutes for Protein purification and scale up" Microbial Cell Factories, Biomed Central, London, NL, vol. 4, No. 1, Nov. 11, 2005.
Banki, et al. "Simple bioseparations using self-cleaving elastin-like polypeptide tags" (Sep. 2005) Nature Methods, 2, 659-661.
Carvajal-Vallejos, et al. "Unprecedented rates and efficiencies revealed for new natural split inteins from metagenomic sources" J. Biol. Chem. 287, 28686-28696 (Aug. 17, 2012).
Chen, et al. Intramolecular disulfide bond between catalytic cysteines in an intein precursor. J Am Chem Soc 134, 2500-2503 (published Jan. 23, 2012).
Chong, et al. "Protein splicing involving the *Saccharomyces cerevisiae* VMA intein" (1996) J Biol Chem, 271, 22159-22168.
Chong, et al. "Modulation of protein splicing of the *Saccharomyces cerevisiae* vacuolar membrane ATPase intein" (Apr. 24, 1998). Journal of Biological Chemistry 273, 10567-10577.
Chong, et al. "Utilizing the C-terminal cleavage activity of a protein splicing element to purify recombinant proteins in a single chromatographic step" (Nov. 15, 1998) Nucleic Acids Res, 26, 5109-5115.
Cosello, et al. "Zinc inhibition of mitochondrial aconitase and its importance in citrate metabolism of prostate epithelial cells" J Biol Chem 272, 28875-28881 (1997).
Dassa, et al. "Fractured genes: a novel genomic arrangement involving new split inteins and a new homing endonuclease family" (2009) Nucleic Acids Research, 37, 2560-2573.
Ding, et al. "Crystal Structure of a Mini-intein Reveals a Conserved Catalytic Module Involved in Side Chain Cyclization of Asparagine during Protein Splicing" (Oct. 3, 2003) Journal of Biological Chemistry, 278, 39133-39142.
European Patent Office (ISA), International Search Report & Written Opinion for PCT/US2014/011076 dated Apr. 2, 2014.

(Continued)

Primary Examiner — Christian L Fronda
(74) Attorney, Agent, or Firm — Edwin S. Flores; Chalker Flores, LLP

(57) ABSTRACT

The present invention includes methods, compositions, uses, and kits for purifying a protein of interest (POI) comprising contacting a first fusion protein comprising the POI fused to the C-terminus of an intein C-fragment with a second fusion protein comprising an intein N-fragment and a purification tag to form a complex between the first fusion protein and the second fusion protein, cleaving the POI from the intein C-fragment, wherein the protein is released from the complex; and isolating the POI; the present invention also includes fusion proteins and vector.

15 Claims, 23 Drawing Sheets
Specification includes a Sequence Listing.

(56) References Cited

OTHER PUBLICATIONS

Frutos, et al. "Branched intermediate formation stimulates peptide bond cleavage in protein splicing" (published online May 23, 2010) Nat Chem Biol, 6, 527-533.
Hashimoto, et al. "Expression and characterization of the chitin-binding domain of chitinase A1 from Bacillus circulans WL-12" Journal of bacteriology 182, 3045-3054 (2000).
Hong, et al. "Simple protein purification through affinity adsorption on regenerated amorphous cellulose followed by intein self-cleavage". J Chromatogr A 1194, 150-154 (2008).
Iwai, et al. "Highly efficient protein trans-splicing by a naturally split DnaE intein from Nostoc punctiforme" (available online Feb. 24, 2006) FEBS Lett, 580, 1853-1858.
Iwai, et al. "Solution structure of DnaE intein from Nostoc punctiforme: Structural basis for the design of a new split intein suitable for site-specific chemical modification" (available online Apr. 1, 2009) Febs Letters, 583, 1451-1456.
Johannes, et al. "Directed evolution of a thermostable phosphite dehydrogenase for NAD(P)H regeneration" Appl Environ Microbiol vol. 71, No. 10, 5728-5734 (Oct. 2005).
Johannes, et al. "Efficient regeneration of NADPH using an engineered phosphite dehydrogenase" (Jan. 1, 2007). Biotechnol Bioeng 96, 18-26.
Johnson, et al. "NMR structure of a KlbA intein precursor from Methanococcus jannaschii" (2007) Protein Science : a publication of the Protein Society, 16, 1316-1328.
Lockless, et al. "Traceless protein splicing utilizing evolved split inteins" (Jul. 7, 2009). Proceedings of the National Academy of Sciences of the United States of America 106, 10999-11004.
Malakhov, et al. "SUMO fusions and SUMO-specific protease for efficient expression and purification of proteins" J Struct. Funct Genomics 5, 75-86 (Mar. 2004).
Oeemig, et al. "Solution structure of DnaE intein from Nostoc punctiforme: structural basis for the design of a new split intein suitable for site-specific chemical modification" FEBS Lett 583, 1451-1456 (available online 2009).
Pereira, et al. "Spontaneous Proton Transfer to a Conserved Intein Residue Determines On-Pathway Protein Splicing" (2011) Journal of Molecular Biology, 406, 430-442.
Perry, et al. Zinc is a potent inhibitor of the apoptotic protease, caspase-3. A novel target for zinc in the inhibition of apoptosis. J Biol Chem 272, 18530-18533 (1997).
Pietrokovski, S. "Conserved sequence features of inteins (protein introns) and their use in identifying new inteins and related proteins" (Dec. 1994) Protein Science, 3, 2340-2350.
Ramirez, et al. "Engineering split intein DnaE from Nostoc punctiforme for rapid protein purification" 2012 (Protein Engineering Design Selection (accepted)).
Shah, et al. "Kinetic control of one-pot trans-splicing reactions by using a wild-type and designed split intein" Angew Chem Int Ed Engl 50, 6511-6515 (Jul. 11, 2011).
Southworth, et al. "Purification of proteins fused to either the amino or carboxy terminus of the *Mycobacterium xenopi* gyrase A intein" (Jul. 1999) BioTechniques 27, 110-114, 116, 118-120.
Sun, et al. "Crystal structures of an intein from the split dnaE gene of *Synechocystis* sp PCC6803 reveal the catalytic model without the penultimate histidine and the mechanism of zinc ion inhibition of protein splicing" Journal of Molecular Biology 353, 1093-1105 (2005).
Tori, et al. "Splicing of the Mycobacteriophage Bethlehem DnaB Intein Identification of a New Mechanistic Class of Inteins That Contain an Obligate Block F Nucleophile*" (Jan. 2010) The Journal of Biological Chemistry, 285, 2515-2526.
Volkmann, et al. "Controllable protein cleavages through intein fragment complementation" (published online Sep. 18, 2009). Protein Science.
Waugh, D.S. "An overview of enzymatic reagents for the removal of affinity tags" Protein Expr. Purif. 80, 283-293 (Dec. 2011).
Wood, et al. "Optimized single-step affinity purification with a self-cleaving intein applied to human acidic fibroblast growth factor" (Published on web Sep. 30, 2000). Biotechnology Progress 16, 1055-1063.
Xu, et al. "The mechanism of protein splicing and its modulation by mutation" EMBO J. 15, 5146-5153 (Oct. 1, 1996).
Zettler, et al. "The naturally split Npu DnaE intein exhibits an extraordinarily high rate in the protein trans-splicing reaction" FEBS Lett 583, 909-914 (Available online Feb. 10, 2009).
Brenzel, et al. "Segmental Isotopic Labeling of Proteins for Nuclear Magnetic Resonance" (2006) Biochemistry, 45, 1571-1578.
Japanese Patent Office, Notification of Reasons for Refusal for Japanese Patent Appl. No. 2015-552813 (National Phase of PCT/US2014/011076) dated Jan. 9, 2018.
Nichols, et al. "Zinc Ion Effects on Individual Ssp DnaE Intein Splicing Steps: Regulatory Pathway Progression" Biochemistry, 2003, 42, 5301-52311.

* cited by examiner

| Trans-splicing | | | | N, C-Cleavage | | | |
|---|---|---|---|---|---|---|---|
| Intein | T(°C) | $t_{1/2}$ | Ref. | N/C | T(°C) | $t_{1/2}$ | Ref. |
| NpuDnaE | 37 | 63s | 1 | N | n.r. | -- | -- |
| | | | | C | 37 | 16min | this work |
| SspDnaE | 23 | 175min | 1 | N | 23 | 11.5min[a] | 2 |
| | 37 | 35min | 1 | C | 23 | 60.8min[a,b] | 2 |
| SceVma[c] | 25 | 6min | 1 | N | 23 | 6min | 3 |
| | | | | C | 23 | 2-6hr | 4 |
| Split SspDnaB | 25 | 12min | 1 | N | RT | 57.8min[a] | 5 |
| | | | | C | RT | 39.4min[a] | 5 |
| MtuRecA[c] | 30 | 60-120min | 6 | N | n.r. | -- | -- |
| | | | | C | 37 | <1hr | 7 |
| gp41-1 | 45 | 3.8s | 8 | N | n.r. | -- | 8 |
| | | | | C | 37 | 5min | |
| gp41-8 | 37 | 15s | 8 | N | n.r. | -- | 8 |
| | | | | C | 37 | 150min | |
| NrdJ-1 | 37 | 7s | 8 | N | n.r. | -- | 8 |
| | | | | C | 37 | 48min | |
| IMPDH-1 | 37 | 8s | 8 | N | n.r. | -- | 8 |
| | | | | C | 37 | 15min | |

FIG. 1

| Construct | Short Name | Protein Sequence | Molecular Weight (kDa) |
|---|---|---|---|
| 1 | C-GFP | NpuC-CFN-GFP-HHHHHH | 32.1 |
| 2 | ChBD- N | ChBD-2x(GGGGS)-NpuN-HHHHHH | 20.5 |
| 3 | C*-GFP | NpuC D118G-CFN-GFP-HHHHHH | 32.0 |
| 4 | ChBD- N<sub>C1A</sub> | ChBD-2x(GGGGS)-NpuN C1A-HHHHHH | 20.5 |
| 5 | ELP- N | ELP-2x(GGGGS)-NpuN-HHHHHH | 59.8 |
| 6 | C*-PTDH | NpuC D118G-CFNAS-PTDH-HHHHHH | 42.2 |
| 7 | C*-DsRed | NpuC D118G-CFNAS-DsRed-HHHHHH | 31.3 |
| 8 | C*-β_Gal | NpuC D118G-CFNAS-β_Gal-HHHHHH | 122.1 |
| 9 | C*-CAT | NpuC D118G-CFNAS-CAT-HHHHHH | 31.3 |
| 10 | C*-MBP | NpuC D118G-CFNAS-MBP-HHHHHH | 48.2 |
| 11 | N-CBD | NpuN-2x(GGGGS)-CBD-6xH | 20.6 |
| 12 | N<sub>C1A</sub>-CBD | NpuNC1A-2x(GGGGS)-CBD-6xH | 20.6 |
| 13 | C-PTDH | NpuC-CFNAS-PTDH-6xH | 42.2 |
| 14 | C*-A-GFP | NpuCD118G-AFN-GFP-6xH | 32.0 |
| 15 | C*-D-GFP | NpuCD118G-DFN-GFP-6xH | 32.0 |
| 16 | C*-L-GFP | NpuCD118G-LFN-GFP-6xH | 32.0 |
| 17 | C*-P-GFP | NpuCD118G-PFN-GFP-6xH | 32.0 |
| 18 | C*-R-GFP | NpuCD118G-RFN-GFP-6xH | 32.0 |

FIG. 3

A-Block

```
              1            10            20            30            40            50
Npu_DnaE      CLSYETEILTVEYGLLP-IGKIVEKRIECTVYSVDNNGNIYTQPVAQWHDRGEQEVFFEYC
Ssp_DnaE      CLSFGTEILTVEYGPLP-IGKIVSEEINCSVYSVDPEGRVYTQAIAQWHDRGEQEVLEYE
Mini-Mtu_RecA CLAEGTRIFDPVTGTTHRIEDVVDGRKPIHVVAAAKDGTLHARPVVSWFDQGTRDVIGLR
              **:  *     *  ::  ** ::    * :  *    :    ::::. * .::*: .:*:
```

B-Block

```
              60           70            80            90           100
Npu_DnaE      LEDGSLIRATKDHKFMTVD-----GQMLPIDEIFE-RELD-LMRVDNLPN------------
Ssp_DnaE      LEDGSVIRATSDHRFLTTD-----YQLLAIEEIFA-RQLD-LLTLENIKQTEEALDNHRL
Mini-Mtu_RecA IAGGAIVWATPDHKVLTEYGWRAAGELRKGDRVAQPRRFDGFGDSAPIPARVQALADALD
              : . ::* ** **:.:* .     :  : .   .   : *     :  :
```

```
                        F-Block     G-Block
              ||    118
              103    110
Npu_DnaE      -----MIKIATRKYLYLGKQ---NVYDIGVERDHNFALKNGFIASN
Ssp_DnaE      PFPLLDAGTIKMVKVIGRRSLGVQ---RIFDIGLPQDHNFLLANGAIAAN
Mini-Mtu_RecA DKFLHDMLAEELRYSVIREVLPTRRARTFDLEVEELH-TLVAEGVVVHN
                  : *.  :    :. .:      *  :*::*:     * :  *
```

FIG. 6

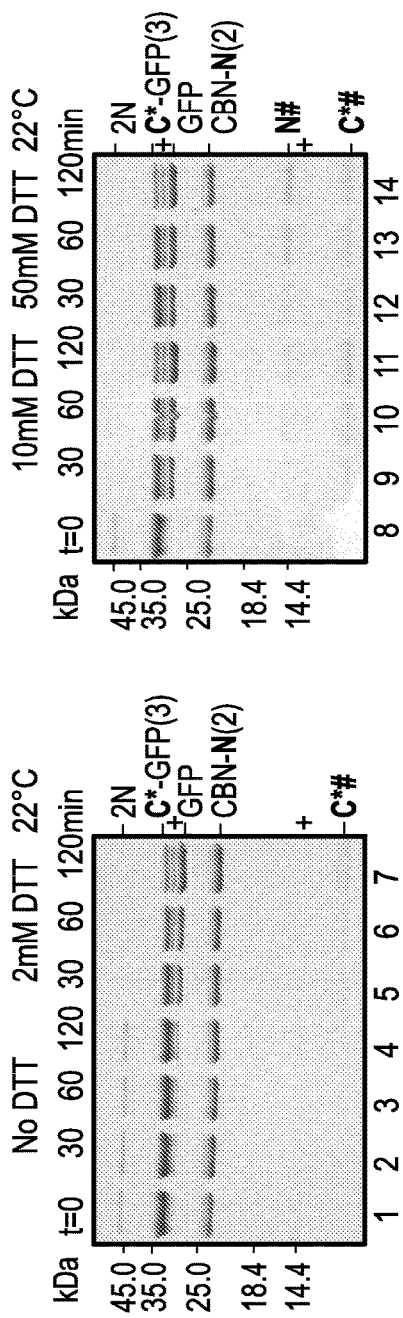
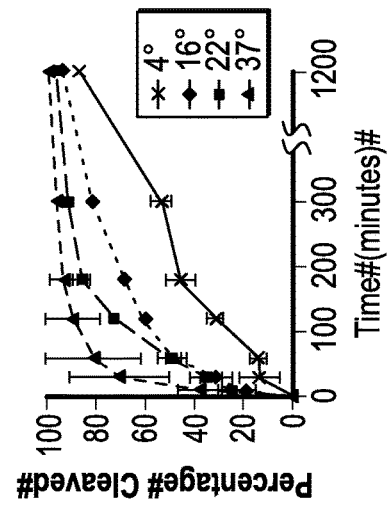
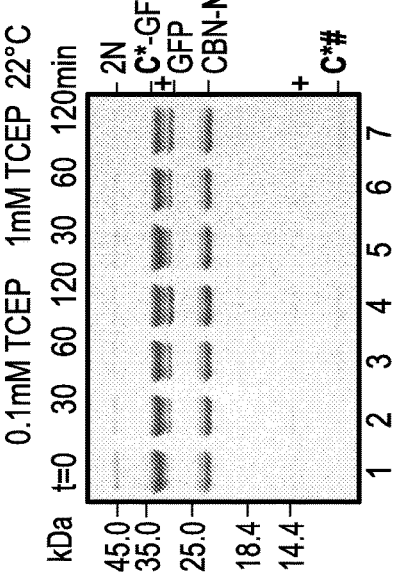
FIG. 7A
FIG. 7B
FIG. 7C

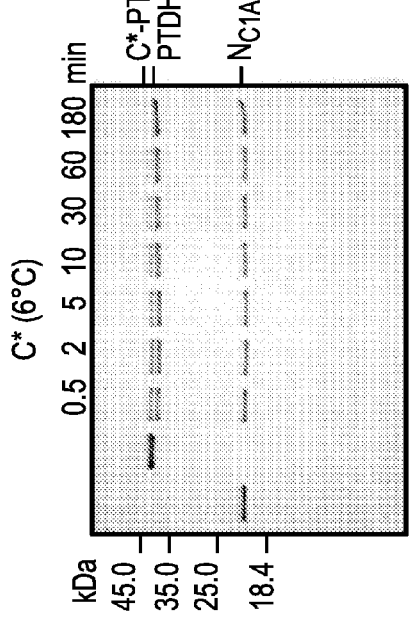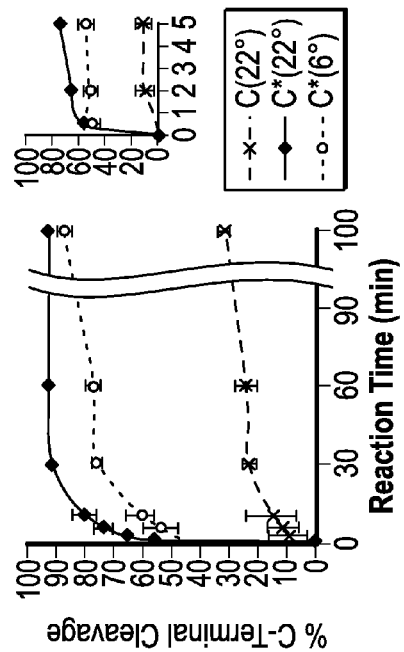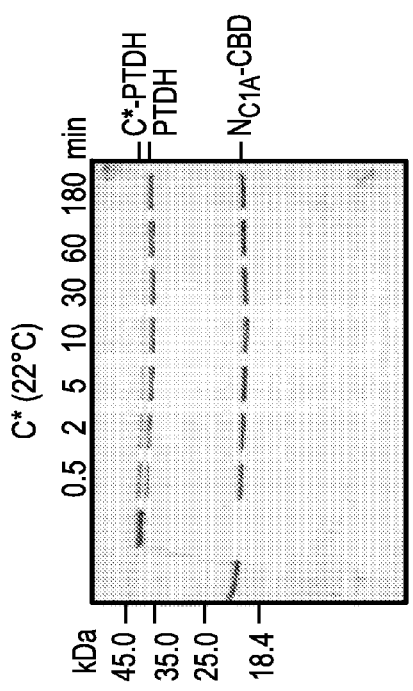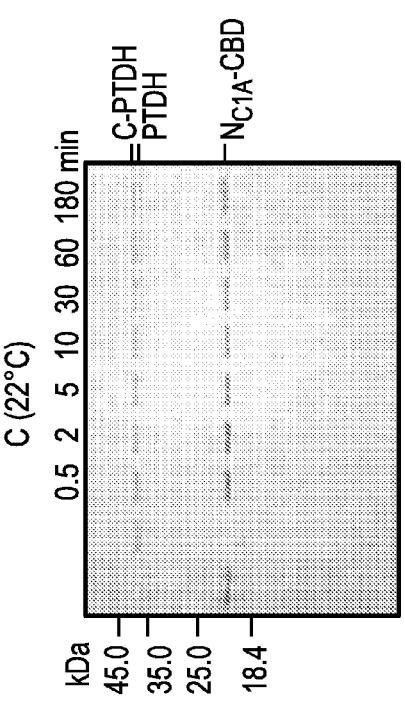
FIG. 10A
FIG. 10B
FIG. 10C
FIG. 10D

| Protein | Size (kDa) | Structure | Yield (mg/L)[b] | | Percent Recovery[c] | | Activity[d] |
|---|---|---|---|---|---|---|---|
| | | | 3h[a] | 20h[a] | 3h[a] | 20h[a] | |
| PTDH | 38.2 | Dimer | 49.8 | 59.3 | 34 | 42 | NBT-methosulfate assay |
| β-Gal | 117 | Tetramer | 68.1 | 84.5 | 68(55)[f] | 76(57)[f] | 261 Units/mg |
| CAT | 27.2 | Trimer | 57.2 | 70.6 | 49 | 61 | ND[e] |
| MBP | 44.1 | Monomer | 53.6 | 57.9 | 26 | 31 | Affinity to Amylose |
| DsRed | 27.2 | Tetramer | 48.9 | 54.4 | 44(45)[f] | 57(55)[f] | Fluorescense at 590nm |
| GFP | 28.2 | Monomer | 56.2 | 62.2 | 43(32)[f] | 47(35)[f] | Fluorescense at 537nm |

FIG. 19

| Activity | β-Gal | DsRed | GFP |
|---|---|---|---|
| Pull-down efficiency[a] | 93% | 93% | 41% |
| Yield (3h)[b] | 56% | 45% | 32% |
| Yield (20h)[c] | 59% | 48% | 37% |
FIG. 20
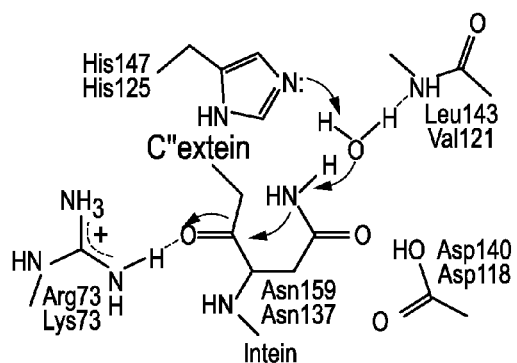
FIG. 21A
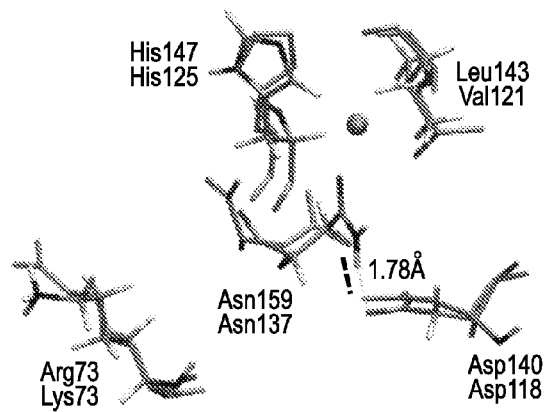
FIG. 21B

| DnaE Intein Name | Genus | Species | Strain |
|---|---|---|---|
| Npu | Nostoc | punctiforme | PCC73102 |
| Ssp | Synechocystis | species | PCC6803 |
| Aha | Aphanothece | halophytica | |
| Aov | Aphanizomenon | ovalisporum | |
| Asp | Anabaena | species | PCC7120 |
| Ava | Anabaena | variabilis | ATCC29413 |
| Cra(CS505) | Cylindrospermopsis | raciborskii | CS-505 |
| Csp(CCY0110) | Cyanothece | species | CCY0110 |
| Csp(PCC8801) | Cyanothece | species | PCC8801 |
| Cwa | Crocosphaera | watsonii | WH 8501 |
| Maer(NIES843) | Microcystis | aeruginosa | NIES-843 |
| Mcht(PCC7420)-2 | Microcoleus | chthonoplastes | PCC7420 |
| Oli | Oscillatoria | limnetica | Solar Lake |
| Sel(PC7942) | Synechococcus | elongatus | PC7942 |
| Ssp(PCC7002) | Synechococcus | species | PCC7002 |
| Tel | Thermosynechococcus | elongatus | BP-1 |
| Ter-3 | Trichodesmium | erythraeum | IMS101 |
| Tvu | Thermosynechococcus | vulcanus | |

FIG. 23

| Name | C-Intein Sequence |
|---|---|
| | 103　　　　　110　　　　　120　　　　　130 |
| Npu | MIKIATRKYLGKQNVYDIGVERDHNFALKNGFIASN |
| Ssp | MVKVIGRRSLGVQRIFDIGLPQDHNFLLANGAIAAN |
| Aha | MVKIIKRQSLGRQNVYDVCVETDHNFVLANGCVASN |
| Aov | MVKITARKFVGRENVYDICVEHHHNFAIKNGLIASN |
| Asp | MIKIASRKFLGVENVYDIGVRRDHNFFIKNGLIASN |
| Ava | MIKIASRKFLGVENVYDIGVGRDHNFFVKNGLIASN |
| Cra (CS505) | MVKIVSRRYLGKADVYDIGVAKDHNFIIKNGLVASN |
| Csp (CCY0110) | MVKIIERRSLGKQNVYDIGVEKDHNFLLSNNLIASN |
| Csp (PCC8801) | MVKIVSYRSLGKQFVDIGVAQDHNFLLANGSIASN |
| Cwa | MVKIIGCRSLGTQKVYDIGVEKDHNFLLANGSIASN |
| Maer (NIES843) | MVKIIGRQSLGRKPVYDIGVEKDHNFLLGNGLIASN |
| Mcht (PCC7420) | MVKIVRRQSLGVQNVYDIGVEKDHNFCLASGEIASN |
| Oli | MVKIVRRQSLGVQNVYDIGVEKDHNFCLASGEIASN |
| Sel (PC7942) | MVKIVRRRSLGVQPVYDIGVATVHNFVLANGLVASN |
| Ssp (PC7002) | MVKIIRRKFIGHAPTYDIGLSQDHNFLLGQGLIAAN |
| Tel | M-KIVGRRLMGWQAVYDIGLAADHNFVLANGAIAAN |
| Ter | MVKIVSRKLAKTENVYDIGVTKDHNFVLANGLIASN |
| Tvu | M-KIVGRRLVGWQAVYDIGLAGDHNFLLANGAIAAN |

Numbering Scheme:
Follows PDB 2KEQ for Npu
Excludes variable N-intein tail
Excludes N-terminal Met for C-inteins

Color Scheme:
A, F, G, I, L, M, P, V, W, Y
C, H, N, Q, S, T
D, E
K, R

FIG. 24B

SEQUENCE LISTING

```
<160> NUMBER OF SEQ IDS: 87

<210> SEQ ID NO 1
<211> LENGTH: 849
<212> TYPE: DNA
<213> ORGANISM: Artificial Sequence
<220> FEATURE:
<223> OTHER INFORMATION: Synthetic primer

<400> SEQUENCE: 1
atgatcaaaa tagccacacg taaatattta ggcaaacaaa atgtctatga cattggagtt      60
gagcgcgacc ataattttgc actcaaaaat ggcttcatag cttctaattg tttcaatgtg     120
agcaagggcg aggagctgtt caccggggtg gtgcccatcc tggtcgagct ggacggcgac     180
gtaaacggcc acaagttcag cgtgtccggc gagggcgagg gcgatgccac ctacggcaag     240
ctgaccctga agttcatctg caccaccggc aagctgcccg tgcccggcc cacccctcgtg     300 accaccctga cctacggcgt gcagtgcttc agccgctacc ccgaccacat gaagcagcac     360
gacttcttca gtccgccat gcccgaaggc tacgtccagg agcgcaccat cttcttcaag     420
gacgacggca actacaagac ccgcgccgag gtgaagttcg agggcgacac cctggtgaac     480
cgcatcgagc tgaagggcat cgacttcaag gaggacggca acatcctggg gcacaagctg     540
gagtacaact acaacagcca caacgtctat atcatggccg acaagcagaa gaacggcatc     600
aaggtgaact tcaagatccg ccacaacatc gaggacggca gcgtgcagct cgccgaccac     660
taccagcaga cacccccat cggcgacggc cccgtgctgc tgcccgacaa ccactacctg     720
agcacccagt ccgccctgag caaagacccc aacgagaagc gcgatcacat ggtcctgctg     780
```

```
gagttcgtga ccgccgccgg gatcactctc ggcatggacg agttactcga gcaccaccac      840
caccaccac                                                              849
```

<210> SEQ ID NO 2
<211> LENGTH: 283
<212> TYPE: PRT
<213> ORGANISM: Artificial Sequence
<220> FEATURE:
<223> OTHER INFORMATION: Synthetic peptide

<400> SEQUENCE: 2

```
Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Asn Cys Phe Asn Val Ser Lys Gly Glu Glu Leu Phe Thr
        35                  40                  45

Gly Val Val Pro Ile Leu Val Glu Leu Asp Gly Asp Val Asn Gly His
    50                  55                  60

Lys Phe Ser Val Ser Gly Glu Gly Glu Gly Asp Ala Thr Tyr Gly Lys
65                  70                  75                  80

Leu Thr Leu Lys Phe Ile Cys Thr Thr Gly Lys Leu Pro Val Pro Trp
                85                  90                  95

Pro Thr Leu Val Thr Thr Leu Thr Tyr Gly Val Gln Cys Phe Ser Arg
            100                 105                 110

Tyr Pro Asp His Met Lys Gln His Asp Phe Phe Lys Ser Ala Met Pro
        115                 120                 125

Glu Gly Tyr Val Gln Glu Arg Thr Ile Phe Phe Lys Asp Asp Gly Asn
    130                 135                 140

Tyr Lys Thr Arg Ala Glu Val Lys Phe Glu Gly Asp Thr Leu Val Asn
145                 150                 155                 160

Arg Ile Glu Leu Lys Gly Ile Asp Phe Lys Glu Asp Gly Asn Ile Leu
                165                 170                 175

Gly His Lys Leu Glu Tyr Asn Tyr Asn Ser His Asn Val Tyr Ile Met
            180                 185                 190

Ala Asp Lys Gln Lys Asn Gly Ile Lys Val Asn Phe Lys Ile Arg His
        195                 200                 205

Asn Ile Glu Asp Gly Ser Val Gln Leu Ala Asp His Tyr Gln Gln Asn
    210                 215                 220

Thr Pro Ile Gly Asp Gly Pro Val Leu Leu Pro Asp Asn His Tyr Leu
225                 230                 235                 240

Ser Thr Gln Ser Ala Leu Ser Lys Asp Pro Asn Glu Lys Arg Asp His
                245                 250                 255

Met Val Leu Leu Glu Phe Val Thr Ala Ala Gly Ile Thr Leu Gly Met
            260                 265                 270

Asp Glu Leu Leu Glu His His His His His His
        275                 280
```

<210> SEQ ID NO 3
<211> LENGTH: 552
<212> TYPE: DNA
<213> ORGANISM: Artificial Sequence
<220> FEATURE:
<223> OTHER INFORMATION: Synthetic primer

<400> SEQUENCE: 3

```
atgaaaatcg aagaaggtaa actgacaaat cctggtgtat ccgcttggca ggtcaacaca      60
```

```
gcttatactg cgggacaatt ggtcacatat aacggcaaga cgtataaatg tttgcagccc      120
cacacctcct tggcaggatg ggaaccatcc aacgttcctg ccttgtggca gcttcaagaa      180
gcttgtggag gcggagggag cggaggcgga gggagcgcta gctgtttaag ctatgaaacg      240
gaaatattga cagtagaata tggattatta ccgattggta aaattgtaga aaagcgcatc      300
gaatgtactg tttatagcgt tgataataat ggaaatattt atacacaacc tgtagcacaa      360
tggcacgatc gcggagaaca agaggtgttt gagtattgtt tggaagatgg ttcattgatt      420
cgggcaacaa aagaccataa gtttatgact gttgatggtc aaatgttgcc aattgatgaa      480
atatttgaac gtgaattgga tttgatgcgg gttgataatt tgccgaatct cgagcaccac      540
caccaccacc ac                                                          552
```

```
<210> SEQ ID NO 4
<211> LENGTH: 184
<212> TYPE: PRT
<213> ORGANISM: Artificial Sequence
<220> FEATURE:
<223> OTHER INFORMATION: Synthetic peptide

<400> SEQUENCE: 4

Met Lys Ile Glu Glu Gly Lys Leu Thr Asn Pro Gly Val Ser Ala Trp
1               5                   10                  15

Gln Val Asn Thr Ala Tyr Thr Ala Gly Gln Leu Val Thr Tyr Asn Gly
            20                  25                  30

Lys Thr Tyr Lys Cys Leu Gln Pro His Thr Ser Leu Ala Gly Trp Glu
        35                  40                  45

Pro Ser Asn Val Pro Ala Leu Trp Gln Leu Gln Glu Ala Cys Gly Gly
    50                  55                  60

Gly Gly Ser Gly Gly Gly Ser Ala Ser Cys Leu Ser Tyr Glu Thr
65                  70                  75                  80

Glu Ile Leu Thr Val Glu Tyr Gly Leu Leu Pro Ile Gly Lys Ile Val
                85                  90                  95

Glu Lys Arg Ile Glu Cys Thr Val Tyr Ser Val Asp Asn Asn Gly Asn
            100                 105                 110

Ile Tyr Thr Gln Pro Val Ala Gln Trp His Asp Arg Gly Glu Gln Glu
        115                 120                 125

Val Phe Glu Tyr Cys Leu Glu Asp Gly Ser Leu Ile Arg Ala Thr Lys
    130                 135                 140

Asp His Lys Phe Met Thr Val Asp Gly Gln Met Leu Pro Ile Asp Glu
145                 150                 155                 160

Ile Phe Glu Arg Glu Leu Asp Leu Met Arg Val Asp Asn Leu Pro Asn
                165                 170                 175

Leu Glu His His His His His His
            180
```

```
<210> SEQ ID NO 5
<211> LENGTH: 849
<212> TYPE: DNA
<213> ORGANISM: Artificial Sequence
<220> FEATURE:
<223> OTHER INFORMATION: Synthetic primer

<400> SEQUENCE: 5
atgatcaaaa tagccacacg taaatattta ggcaaacaaa atgtctatgg cattggagtt       60
gagcgcgacc ataattttgc actcaaaaat ggcttcatag cttctaattg tttcaatgtg      120
```

-continued

```
agcaagggcg aggagctgtt caccggggtg gtgcccatcc tggtcgagct ggacggcgac    180
gtaaacggcc acaagttcag cgtgtccggc gagggcgagg gcgatgccac ctacggcaag    240
ctgaccctga agttcatctg caccaccggc aagctgcccg tgccctggcc caccctcgtg    300
accaccctga cctacggcgt gcagtgcttc agccgctacc ccgaccacat gaagcagcac    360
gacttcttca gtccgccat gcccgaaggc tacgtccagg agcgcaccat cttcttcaag    420
gacgacggca actacaagac ccgcgccgag gtgaagttcg agggcgacac cctggtgaac    480
cgcatcgagc tgaagggcat cgacttcaag gaggacggca acatcctggg gcacaagctg    540
gagtacaact acaacagcca caacgtctat atcatggccg acaagcagaa gaacggcatc    600
aaggtgaact tcaagatccg ccacaacatc gaggacggca gcgtgcagct cgccgaccac    660
taccagcaga acaccccat cggcgacggc cccgtgctgc tgcccgacaa ccactacctg    720
agcacccagt ccgccctgag caagacccc aacgagaagc gcgatcacat ggtcctgctg    780
gagttcgtga ccgccgccgg gatcactctc ggcatggacg agttactcga gcaccaccac    840
caccaccac                                                            849
```

<210> SEQ ID NO 6
<211> LENGTH: 184
<212> TYPE: PRT
<213> ORGANISM: Artificial Sequence
<220> FEATURE:
<223> OTHER INFORMATION: Synthetic peptide

<400> SEQUENCE: 6

```
Met Lys Ile Glu Glu Gly Lys Leu Thr Asn Pro Gly Val Ser Ala Trp
1               5                   10                  15

Gln Val Asn Thr Ala Tyr Thr Ala Gly Gln Leu Val Thr Tyr Asn Gly
            20                  25                  30

Lys Thr Tyr Lys Cys Leu Gln Pro His Thr Ser Leu Ala Gly Trp Glu
        35                  40                  45

Pro Ser Asn Val Pro Ala Leu Trp Gln Leu Gln Glu Ala Cys Gly Gly
    50                  55                  60

Gly Gly Ser Gly Gly Gly Ser Ala Ser Ala Leu Ser Tyr Glu Thr
65                  70                  75                  80

Glu Ile Leu Thr Val Glu Tyr Gly Leu Leu Pro Ile Gly Lys Ile Val
                85                  90                  95

Glu Lys Arg Ile Glu Cys Thr Val Tyr Ser Val Asp Asn Asn Gly Asn
            100                 105                 110

Ile Tyr Thr Gln Pro Val Ala Gln Trp His Asp Arg Gly Glu Gln Glu
        115                 120                 125

Val Phe Glu Tyr Cys Leu Glu Asp Gly Ser Leu Ile Arg Ala Thr Lys
    130                 135                 140

Asp His Lys Phe Met Thr Val Asp Gly Gln Met Leu Pro Ile Asp Glu
145                 150                 155                 160

Ile Phe Glu Arg Glu Leu Asp Leu Met Arg Val Asp Asn Leu Pro Asn
                165                 170                 175

Leu Glu His His His His His His
            180
```

<210> SEQ ID NO 7
<211> LENGTH: 552
<212> TYPE: DNA
<213> ORGANISM: Artificial Sequence
<220> FEATURE:
<223> OTHER INFORMATION: Synthetic primer

<400> SEQUENCE: 7

```
atgaaaatcg aagaaggtaa actgacaaat cctggtgtat ccgcttggca ggtcaacaca      60
gcttatactg cgggacaatt ggtcacatat aacggcaaga cgtataaatg tttgcagccc     120
cacacctcct tggcaggatg ggaaccatcc aacgttcctg ccttgtgca gcttcaagaa     180
gcttgtggag gcggagggag cggaggcgga gggagcgcta gcgccttaag ctatgaaacg     240
gaaatattga cagtagaata tggattatta ccgattggta aaattgtaga aaagcgcatc     300
gaatgtactg tttatagcgt tgataataat ggaaatattt atacacaacc tgtagcacaa     360
tggcacgatc gcggagaaca agaggtgttt gagtattgtt tggaagatgg ttcattgatt     420
cgggcaacaa agaccataa gtttatgact gttgatggtc aaatgttgcc aattgatgaa     480
atatttgaac gtgaattgga tttgatgcgg gttgataatt tgccgaatct cgagcaccac     540
caccaccacc ac                                                         552
```

<210> SEQ ID NO 8
<211> LENGTH: 184
<212> TYPE: PRT
<213> ORGANISM: Artificial Sequence
<220> FEATURE:
<223> OTHER INFORMATION: Synthetic peptide

<400> SEQUENCE: 8

```
Met Lys Ile Glu Glu Gly Lys Leu Thr Asn Pro Gly Val Ser Ala Trp
1               5                   10                  15
Gln Val Asn Thr Ala Tyr Thr Ala Gly Gln Leu Val Thr Tyr Asn Gly
            20                  25                  30
Lys Thr Tyr Lys Cys Leu Gln Pro His Thr Ser Leu Ala Gly Trp Glu
        35                  40                  45
Pro Ser Asn Val Pro Ala Leu Trp Gln Leu Gln Glu Ala Cys Gly Gly
    50                  55                  60
Gly Gly Ser Gly Gly Gly Gly Ser Ala Ser Ala Leu Ser Tyr Glu Thr
65                  70                  75                  80
Glu Ile Leu Thr Val Glu Tyr Gly Leu Leu Pro Ile Gly Lys Ile Val
                85                  90                  95
Glu Lys Arg Ile Glu Cys Thr Val Tyr Ser Val Asp Asn Asn Gly Asn
            100                 105                 110
Ile Tyr Thr Gln Pro Val Ala Gln Trp His Asp Arg Gly Glu Gln Glu
        115                 120                 125
Val Phe Glu Tyr Cys Leu Glu Asp Gly Ser Leu Ile Arg Ala Thr Lys
    130                 135                 140
Asp His Lys Phe Met Thr Val Asp Gly Gln Met Leu Pro Ile Asp Glu
145                 150                 155                 160
Ile Phe Glu Arg Glu Leu Asp Leu Met Arg Val Asp Asn Leu Pro Asn
                165                 170                 175
Leu Glu His His His His His His
            180
```

<210> SEQ ID NO 9
<211> LENGTH: 2103
<212> TYPE: DNA
<213> ORGANISM: Artificial Sequence
<220> FEATURE:
<223> OTHER INFORMATION: Synthetic primer

<400> SEQUENCE: 9

```
atgggccacg gcgtgggtgt tccgggcgtg gtgttccgg gtggcggtgt gccgggcgca      60
ggtgttcctg gtgtaggtgt gccgggtgtt ggtgtgccgg gtgttggtgt accaggtggc     120
ggtgttccgg gtgcaggcgt tccgggtggc ggtgtgccgg gcgtgggtgt tccgggcgtg    180
ggtgttccgg gtggcggtgt gccgggcgca ggtgttcctg gtgtaggtgt gccgggtgtt    240
ggtgtgccgg gtgttggtgt accaggtggc ggtgttccgg gtgcaggcgt tccgggtggc    300
ggtgtgccgg gcgtgggtgt tccgggcgtg gtgttccgg gtggcggtgt gccgggcgca    360
ggtgttcctg gtgtaggtgt gccgggtgtt ggtgtgccgg gtgttggtgt accaggtggc    420
ggtgttccgg gtgcaggcgt tccgggtggc ggtgtgccgg gcgtgggtgt tccgggcgtg    480
ggtgttccgg gtggcggtgt gccgggcgca ggtgttcctg gtgtaggtgt gccgggtgtt    540
ggtgtgccgg gtgttggtgt accaggtggc ggtgttccgg gtgcaggcgt tccgggtggc    600
ggtgtgccgg gcgtgggtgt tccgggcgtg gtgttccgg gtggcggtgt gccgggcgca    660
ggtgttcctg gtgtaggtgt gccgggtgtt ggtgtgccgg gtgttggtgt accaggtggc    720
ggtgttccgg gtgcaggcgt tccgggtggc ggtgtgccgg gcgtgggtgt tccgggcgtg    780
ggtgttccgg gtggcggtgt gccgggcgca ggtgttcctg gtgtaggtgt gccgggtgtt    840
ggtgtgccgg gtgttggtgt accaggtggc ggtgttccgg gtgcaggcgt tccgggtggc    900
ggtgtgccgg gcgtgggtgt tccgggcgtg gtgttccgg gtggcggtgt gccgggcgca    960
ggtgttcctg gtgtaggtgt gccgggtgtt ggtgtgccgg gtgttggtgt accaggtggc   1020
ggtgttccgg gtgcaggcgt tccgggtggc ggtgtgccgg gcgtgggtgt tccgggcgtg   1080
ggtgttccgg gtggcggtgt gccgggcgca ggtgttcctg gtgtaggtgt gccgggtgtt   1140
ggtgtgccgg gtgttggtgt accaggtggc ggtgttccgg gtgcaggcgt tccgggtggc   1200
ggtgtgccgg gcgtgggtgt tccgggcgtg gtgttccgg gtggcggtgt gccgggcgca   1260
ggtgttcctg gtgtaggtgt gccgggtgtt ggtgtgccgg gtgttggtgt accaggtggc   1320
ggtgttccgg gtgcaggcgt tccgggtggc ggtgtgccgg gcgtgggtgt tccgggcgtg   1380
ggtgttccgg gtggcggtgt gccgggcgca ggtgttcctg gtgtaggtgt gccgggtgtt   1440
ggtgtgccgg gtgttggtgt accaggtggc ggtgttccgg gtgcaggcgt tccgggtggc   1500
ggtgtgccgg gcgtgggtgt tccgggcgtg gtgttccgg gtggcggtgt gccgggcgca   1560
ggtgttcctg gtgtaggtgt gccgggtgtt ggtgtgccgg gtgttggtgt accaggtggc   1620
ggtgttccgg gtgcaggcgt tccgggtggc ggtgtgccgg gcgggctggt gagctcgaac   1680
aacaacaaca ataacaataa caacaacctc gggatcgagg gaaggatttc agaattcgga   1740
ggcggaggga gcggaggcgg agggagcgct agctgtttaa gctatgaaac ggaaatattg   1800
acagtagaat atggattatt accgattggt aaaattgtag aaaagcgcat cgaatgtact   1860
gtttatagcg ttgataataa tggaaatatt tatacacaac ctgtagcaca atggcacgat   1920
cgcggagaac aagaggtgtt tgagtattgt ttggaagatg gttcattgat tcgggcaaca   1980
aaagaccata agtttatgac tgttgatggt caaatgttgc caattgatga aatatttgaa   2040
cgtgaattgg atttgatgcg ggttgataat ttgccgaatc tcgagcacca ccaccaccac   2100
cac                                                                 2103
```

<210> SEQ ID NO 10
<211> LENGTH: 701
<212> TYPE: PRT
<213> ORGANISM: Artificial Sequence
<220> FEATURE:
<223> OTHER INFORMATION: Synthetic peptide

<400> SEQUENCE: 10

```
Met Gly His Gly Val Gly Val Pro Gly Val Gly Val Pro Gly Gly Gly
1               5                   10                  15

Val Pro Gly Ala Gly Val Pro Gly Val Gly Val Pro Gly Val Gly Val
                20                  25                  30

Pro Gly Val Gly Val Pro Gly Gly Val Pro Gly Ala Gly Val Pro
            35                  40                  45

Gly Gly Gly Val Pro Gly Val Gly Val Pro Gly Val Gly Val Pro Gly
50                  55                  60

Gly Gly Val Pro Gly Ala Gly Val Pro Gly Val Gly Val Pro Gly Val
65                  70                  75                  80

Gly Val Pro Gly Val Gly Val Pro Gly Gly Gly Val Pro Gly Ala Gly
                85                  90                  95

Val Pro Gly Gly Gly Val Pro Gly Val Gly Val Pro Gly Val Gly Val
                100                 105                 110

Pro Gly Gly Gly Val Pro Gly Ala Gly Val Pro Gly Val Gly Val Pro
            115                 120                 125

Gly Val Gly Val Pro Gly Val Gly Val Pro Gly Gly Gly Val Pro Gly
            130                 135                 140

Ala Gly Val Pro Gly Gly Val Pro Gly Val Gly Val Pro Gly Val
145                 150                 155                 160

Gly Val Pro Gly Gly Gly Val Pro Gly Ala Gly Val Pro Gly Val Gly
                165                 170                 175

Val Pro Gly Val Gly Val Pro Gly Val Gly Val Pro Gly Gly Gly Val
                180                 185                 190

Pro Gly Ala Gly Val Pro Gly Gly Val Pro Gly Val Gly Val Pro
            195                 200                 205

Gly Val Gly Val Pro Gly Gly Val Pro Gly Ala Gly Val Pro Gly
            210                 215                 220

Val Gly Val Pro Gly Val Gly Val Pro Gly Val Gly Val Pro Gly Gly
225                 230                 235                 240

Gly Val Pro Gly Ala Gly Val Pro Gly Gly Val Pro Gly Val Gly
                245                 250                 255

Val Pro Gly Val Gly Val Pro Gly Gly Gly Val Pro Gly Ala Gly Val
            260                 265                 270

Pro Gly Val Gly Val Pro Gly Val Gly Val Pro Gly Val Gly Val Pro
            275                 280                 285

Gly Gly Gly Val Pro Gly Ala Gly Val Pro Gly Gly Gly Val Pro Gly
290                 295                 300

Val Gly Val Pro Gly Val Gly Val Pro Gly Gly Gly Val Pro Gly Ala
305                 310                 315                 320

Gly Val Pro Gly Val Gly Val Pro Gly Val Gly Val Pro Gly Val Gly
                325                 330                 335

Val Pro Gly Gly Gly Val Pro Gly Ala Gly Val Pro Gly Gly Gly Val
                340                 345                 350

Pro Gly Val Gly Val Pro Gly Val Gly Val Pro Gly Gly Gly Val Pro
            355                 360                 365

Gly Ala Gly Val Pro Gly Val Gly Val Pro Gly Val Gly Val Pro Gly
            370                 375                 380

Val Gly Val Pro Gly Gly Gly Val Pro Gly Ala Gly Val Pro Gly Gly
385                 390                 395                 400

Gly Val Pro Gly Val Gly Val Pro Gly Val Gly Val Pro Gly Gly Gly
```

-continued

```
                405                 410                 415
Val Pro Gly Ala Gly Val Pro Gly Val Gly Val Pro Gly Val Gly Val
            420                 425                 430
Pro Gly Val Gly Val Pro Gly Gly Val Pro Gly Ala Gly Val Pro
        435                 440                 445
Gly Gly Gly Val Pro Gly Val Gly Val Pro Gly Val Gly Val Pro Gly
450                 455                 460
Gly Gly Val Pro Gly Ala Gly Val Pro Gly Val Gly Val Pro Gly Val
465                 470                 475                 480
Gly Val Pro Gly Val Gly Val Pro Gly Gly Val Pro Gly Ala Gly
                485                 490                 495
Val Pro Gly Gly Gly Val Pro Gly Val Gly Val Pro Gly Val Gly Val
            500                 505                 510
Pro Gly Gly Gly Val Pro Gly Ala Gly Val Pro Gly Val Gly Val Pro
        515                 520                 525
Gly Val Gly Val Pro Gly Val Gly Val Pro Gly Gly Val Pro Gly
        530                 535                 540
Ala Gly Val Pro Gly Gly Val Pro Gly Gly Leu Val Ser Ser Asn
545                 550                 555                 560
Asn Asn Asn Asn Asn Asn Asn Leu Gly Ile Glu Gly Arg Ile
                565                 570                 575
Ser Glu Phe Gly Gly Gly Ser Gly Gly Gly Ser Ala Ser Cys
            580                 585                 590
Leu Ser Tyr Glu Thr Glu Ile Leu Thr Val Glu Tyr Gly Leu Leu Pro
            595                 600                 605
Ile Gly Lys Ile Val Glu Lys Arg Ile Glu Cys Thr Val Tyr Ser Val
        610                 615                 620
Asp Asn Asn Gly Asn Ile Tyr Thr Gln Pro Val Ala Gln Trp His Asp
625                 630                 635                 640
Arg Gly Glu Gln Glu Val Phe Glu Tyr Cys Leu Glu Asp Gly Ser Leu
                645                 650                 655
Ile Arg Ala Thr Lys Asp His Lys Phe Met Thr Val Asp Gly Gln Met
            660                 665                 670
Leu Pro Ile Asp Glu Ile Phe Glu Arg Glu Leu Asp Leu Met Arg Val
        675                 680                 685
Asp Asn Leu Pro Asn Leu Glu His His His His His
        690                 695                 700
```

<210> SEQ ID NO 11
<211> LENGTH: 1155
<212> TYPE: DNA
<213> ORGANISM: Artificial Sequence
<220> FEATURE:
<223> OTHER INFORMATION: Synthetic primer

<400> SEQUENCE: 11

```
atgatcaaaa tagccacacg taaatattta ggcaaacaaa atgtctatgg cattggagtt    60
gagcgcgacc ataatttgc actcaaaaat ggcttcatag cttctaattg tttcaatgct   120
agcatgctgc cgaaactcgt tataactcac cgagtacacg aagagatcct gcaactgctg   180
gcgccacatt gcgagctgat aaccaaccag accgacagca cgctgacgcg cgaggaaatt   240
ctgcgccgct gtcgcgatgc tcaggcgatg atggcgttca tgcccgatcg ggtcgatgca   300
gactttcttc aagcctgccc tgagctgcgt gtaatcggct gcgcgctcaa gggcttcgac   360
aatttcgatg tggacgcctg tactgcccgc ggggtctggc tgaccttcgt gcctgatctg   420
```

```
ttgacggtcc cgactgccga gctggcgatc ggactggcgg tggggctggg gcggcatctg    480
cgggcagcag atgcgttcgt ccgctctggc aagttccggg gctggcaacc acggttctac    540
ggcacggggc tggataacgc tacggtcggc ttccttggca tgggcgccat cggactggcc    600
atggctgatc gcttgcaggg atggggcgcg accctgcagt accacgcgcg gaaggctctg    660
gatacacaaa ccgagcaacg gctcggcctg cgccaggtgg cgtgcagcga actcttcgcc    720
agctcggact tcatcctgct ggcgcttccc ttgaatgccg ataccctgca tctggtcaac    780
gccgagctgc ttgccctcgt acggccgggc gctctgcttg taaaccctg tcgtggctcg      840 gtagtggatg aagccgccgt gctcgcggcg cttgagcgag ccagctcgg cgggtatgcg       900 gcggatgtat tcgaaatgga agactgggct cgcgcggacc ggccgcagca gatcgatcct    960
gcgctgctcg cgcatccgaa tacgctgttc actccgcaca tagggtcggc agtgcgcgcg    1020
gtgcgcctgg agattgaacg ttgtgcagcg cagaacatcc tccaggcatt ggcaggtgag    1080
cgcccaatca cgctgtgaa ccgtctgccc aaggccaatc ctgccgcaga cctcgagcac     1140
caccaccacc accac                                                     1155
```

<210> SEQ ID NO 12
<211> LENGTH: 385
<212> TYPE: PRT
<213> ORGANISM: Artificial Sequence
<220> FEATURE:
<223> OTHER INFORMATION: Synthetic peptide

<400> SEQUENCE: 12

```
Met Ile Lys Ile Ala Thr Arg Lys Tyr Leu Gly Lys Gln Asn Val Tyr
1               5                   10                  15

Gly Ile Gly Val Glu Arg Asp His Asn Phe Ala Leu Lys Asn Gly Phe
            20                  25                  30

Ile Ala Ser Asn Cys Phe Asn Ala Ser Met Leu Pro Lys Leu Val Ile
        35                  40                  45

Thr His Arg Val His Glu Glu Ile Leu Gln Leu Leu Ala Pro His Cys
    50                  55                  60

Glu Leu Ile Thr Asn Gln Thr Asp Ser Thr Leu Thr Arg Glu Glu Ile
65                  70                  75                  80

Leu Arg Arg Cys Arg Asp Ala Gln Ala Met Met Ala Phe Met Pro Asp
                85                  90                  95

Arg Val Asp Ala Asp Phe Leu Gln Ala Cys Pro Glu Leu Arg Val Ile
            100                 105                 110

Gly Cys Ala Leu Lys Gly Phe Asp Asn Phe Val Asp Ala Cys Thr
        115                 120                 125

Ala Arg Gly Val Trp Leu Thr Phe Val Pro Asp Leu Leu Thr Val Pro
    130                 135                 140

Thr Ala Glu Leu Ala Ile Gly Leu Ala Val Gly Leu Gly Arg His Leu
145                 150                 155                 160

Arg Ala Ala Asp Ala Phe Val Arg Ser Gly Lys Phe Arg Gly Trp Gln
                165                 170                 175

Pro Arg Phe Tyr Gly Thr Gly Leu Asp Asn Ala Thr Val Gly Phe Leu
            180                 185                 190

Gly Met Gly Ala Ile Gly Leu Ala Met Ala Asp Arg Leu Gln Gly Trp
        195                 200                 205

Gly Ala Thr Leu Gln Tyr His Ala Arg Lys Ala Leu Asp Thr Gln Thr
    210                 215                 220
```

```
Glu Gln Arg Leu Gly Leu Arg Gln Val Ala Cys Ser Glu Leu Phe Ala
225                 230                 235                 240

Ser Ser Asp Phe Ile Leu Leu Ala Leu Pro Leu Asn Ala Asp Thr Leu
            245                 250                 255

His Leu Val Asn Ala Glu Leu Leu Ala Leu Val Arg Pro Gly Ala Leu
        260                 265                 270

Leu Val Asn Pro Cys Arg Gly Ser Val Val Asp Glu Ala Ala Val Leu
    275                 280                 285

Ala Ala Leu Glu Arg Gly Gln Leu Gly Gly Tyr Ala Ala Asp Val Phe
290                 295                 300

Glu Met Glu Asp Trp Ala Arg Ala Asp Arg Pro Gln Gln Ile Asp Pro
305                 310                 315                 320

Ala Leu Leu Ala His Pro Asn Thr Leu Phe Thr Pro His Ile Gly Ser
            325                 330                 335

Ala Val Arg Ala Val Arg Leu Glu Ile Glu Arg Cys Ala Ala Gln Asn
        340                 345                 350

Ile Leu Gln Ala Leu Ala Gly Glu Arg Pro Ile Asn Ala Val Asn Arg
    355                 360                 365

Leu Pro Lys Ala Asn Pro Ala Ala Asp Leu Glu His His His His His
370                 375                 380

His
385

<210> SEQ ID NO 13
<211> LENGTH: 819
<212> TYPE: DNA
<213> ORGANISM: Artificial Sequence
<220> FEATURE:
<223> OTHER INFORMATION: Synthetic primer

<400> SEQUENCE: 13
atgatcaaaa tagccacacg taaatattta ggcaaacaaa atgtctatgg cattggagtt      60
gagcgcgacc ataattttgc actcaaaaat ggcttcatag cttctaattg tttcaatgct     120
agcgcctcct ccgaggacgt catcaaggag ttcatgcgct tcaaggtgcg catggagggc     180
tccgtgaacg gccacgagtt cgagatcgag ggcgaggggc gaggccgccc ctacgagggc     240
acccagaccg ccaagctgaa ggtgaccaag gcggcccccc tgcccttcgc ctgggacatc     300
ctgtcccccc agttccagta cggctccaag gtgtacgtga agcaccccgc cgacatcccc     360
gactacaaga gctgtccttt ccccgagggc ttcaagtggg agcgcgtgat gaacttcgag     420
gacggcggcg tggtgaccgt gacccaggac tcctccctgc aggacggctc cttcatctac     480
aaggtgaagt tcatcggcgt gaacttcccc tccgacggcc ccgtaatgca gaagaagact     540
atgggctggg aggcctccac cgagcgcctg taccccgcg acggcgtgct gaagggcgag     600
atccacaagg ccctgaagct gaaggacggc ggccactacc tggtggagtt caagtccatc     660
tacatggcca agaagcccgt gcagctgccc ggctactact acgtggactc caagctggac     720
atcacctccc acaacgagga ctacaccatc gtggagcagt acgagcgcgc cgagggccgc     780
caccacctgt cctgctcga gcaccaccac caccaccac                              819

<210> SEQ ID NO 14
<211> LENGTH: 273
<212> TYPE: PRT
<213> ORGANISM: Artificial Sequence
<220> FEATURE:
<223> OTHER INFORMATION: Synthetic peptide
```

-continued

<400> SEQUENCE: 14

Met Ile Lys Ile Ala Thr Arg Lys Tyr Leu Gly Lys Gln Asn Val Tyr
1               5                   10                  15

Gly Ile Gly Val Glu Arg Asp His Asn Phe Ala Leu Lys Asn Gly Phe
            20                  25                  30

Ile Ala Ser Asn Cys Phe Asn Ala Ser Ala Ser Ser Glu Asp Val Ile
        35                  40                  45

Lys Glu Phe Met Arg Phe Lys Val Arg Met Glu Gly Ser Val Asn Gly
    50                  55                  60

His Glu Phe Glu Ile Glu Gly Glu Gly Arg Pro Tyr Glu Gly
65                  70                  75                  80

Thr Gln Thr Ala Lys Leu Lys Val Thr Lys Gly Gly Pro Leu Pro Phe
                85                  90                  95

Ala Trp Asp Ile Leu Ser Pro Gln Phe Gln Tyr Gly Ser Lys Val Tyr
            100                 105                 110

Val Lys His Pro Ala Asp Ile Pro Asp Tyr Lys Lys Leu Ser Phe Pro
        115                 120                 125

Glu Gly Phe Lys Trp Glu Arg Val Met Asn Phe Glu Asp Gly Gly Val
    130                 135                 140

Val Thr Val Thr Gln Asp Ser Ser Leu Gln Asp Gly Ser Phe Ile Tyr
145                 150                 155                 160

Lys Val Lys Phe Ile Gly Val Asn Phe Pro Ser Asp Gly Pro Val Met
                165                 170                 175

Gln Lys Lys Thr Met Gly Trp Glu Ala Ser Thr Glu Arg Leu Tyr Pro
            180                 185                 190

Arg Asp Gly Val Leu Lys Gly Glu Ile His Lys Ala Leu Lys Leu Lys
        195                 200                 205

Asp Gly Gly His Tyr Leu Val Glu Phe Lys Ser Ile Tyr Met Ala Lys
    210                 215                 220

Lys Pro Val Gln Leu Pro Gly Tyr Tyr Tyr Val Asp Ser Lys Leu Asp
225                 230                 235                 240

Ile Thr Ser His Asn Glu Asp Tyr Thr Ile Val Glu Gln Tyr Glu Arg
                245                 250                 255

Ala Glu Gly Arg His His Leu Phe Leu Leu Glu His His His His
            260                 265                 270

His

<210> SEQ ID NO 15
<211> LENGTH: 3219
<212> TYPE: DNA
<213> ORGANISM: Artificial Sequence
<220> FEATURE:
<223> OTHER INFORMATION: Synthetic primer

<400> SEQUENCE: 15
atgatcaaaa tagccacacg taaatatttta ggcaaacaaa atgtctatgg cattggagtt      60
gagcgcgacc ataattttgc actcaaaaat ggcttcatag cttctaattg tttcaatgct     120
agcatgacca tgattacgga ttcactcgcc gtcgttttac aacgtcgtga ctgggaaaac     180
cctggcgtta cccaacttaa tcgccttgca gcacatcccc ctttcgccag ctggcgtaat     240
agcgaagagg cccgcaccga tcgcccttcc aacagttgc gcagcctgaa tggcgaatgg     300
cgctttgcct ggtttccggc accagaagcg gtgccggaaa gctggctgga gtgcgatctt     360
cctgaggccg atactgtcgt cgtcccctca aactggcaga tgcacggtta cgatgcgccc     420

-continued

```
atctacacca acgtgaccta tcccattacg gtcaatccgc cgtttgttcc cacggagaat      480
ccgacgggtt gttactcgct cacatttaat gttgatgaaa gctggctaca ggaaggccag      540
acgcgaatta tttttgatgg cgttaactcg gcgtttcatc tgtggtgcaa cgggcgctgg      600
gtcggttacg gccaggacag tcgtttgccg tctgaatttg acctgagcgc attttttacgc     660 gccggagaaa accgcctcgc ggtgatggtg ctgcgctgga gtgacggcag ttatctggaa      720
gatcaggata tgtggcggat gagcggcatt ttccgtgacg tctcgttgct gcataaaccg      780
actacacaaa tcagcgattt ccatgttgcc actcgcttta atgatgattt cagccgcgct      840
gtactggagg ctgaagttca gatgtgcggc gagttgcgtg actacctacg ggtaacagtt      900
tctttatggc agggtgaaac gcaggtcgcc agcggcaccg cgcctttcgg cggtgaaatt      960
atcgatgagc gtggtggtta tgccgatcgc gtcacactac gtctgaacgt cgaaaacccg     1020
aaactgtgga gcgccgaaat cccgaatctc tatcgtgcgg tggttgaact gcacaccgcc     1080
gacggcacgc tgattgaagc agaagcctgc gatgtcggtt ccgcgaggt gcggattgaa      1140 aatggtctgc tgctgctgaa cggcaagccg ttgctgattc gaggcgttaa ccgtcacgag     1200
catcatcctc tgcatggtca ggtcatggat gagcagacga tggtgcagga tatcctgctg     1260
atgaagcaga acaactttaa cgccgtgcgc tgttcgcatt atccgaacca tccgctgtgg     1320
tacacgctgt gcgaccgcta cggcctgtat gtggtggatg aagccaatat tgaaacccac     1380
ggcatggtgc aatgaatcg tctgaccgat gatccgcgct ggctaccggc gatgagcgaa      1440
cgcgtaacgc gaatggtgca gcgcgatcgt aatcacccga gtgtgatcat ctggtcgctg     1500
gggaatgaat caggccacgg cgctaatcac gacgcgctgt atcgctggat caaatctgtc     1560
gatccttccc gcccggtgca gtatgaaggc ggcggagccg acaccacggc caccgatatt     1620
atttgcccga tgtacgcgcg cgtggatgaa accagcccct tcccggctgt gccgaaatgg     1680
tccatcaaaa aatggctttc gctacctgga gagacgcgcc cgctgatcct ttgcgaatac     1740
gcccacgcga tgggtaacag tcttggcggt ttcgctaaat actggcaggc gtttcgtcag     1800
tatccccgtt tacagggcgg cttcgtctgg gactgggtgg atcagtcgct gattaaatat     1860
gatgaaaacg caacccgtg gtcggcttac ggcggtgatt ttggcgatac gccgaacgat     1920
cgccagttct gtatgaacgg tctggtcttt gccgaccgca cgccgcatcc agcgctgacg     1980
gaagcaaaac accagcagca gttttttccag ttccgtttat ccgggcaaac catcgaagtg     2040
accagcgaat acctgttccg tcatagcgat aacgagctcc tgcactggat ggtggcgctg     2100
gatggtaagc cgctggcaag cggtgaagtg cctctggatg tcgctccaca aggtaaacag     2160
ttgattgaac tgcctgaact accgcagccg gagagcgccg ggcaactctg gctcacagta     2220
cgcgtagtgc aaccgaacgc gaccgcatgg tcagaagccg ggcacatcag cgcctggcag     2280
cagtggcgtc tggcggaaaa cctcagtgtg acgctccccg ccgcgtccca cgccatcccg     2340
catctgacca ccagcgaaat ggattttttgc atcgagctgg gtaataagcg ttggcaattt     2400
aaccgccagt caggctttct ttcacagatg tggattggcg ataaaaaaca actgctgacg     2460
ccgctgcgcg atcagttcac ccgtgcaccg ctggataacg acattggcgt aagtgaagcg     2520
acccgcattg accctaacgc ctgggtcgaa cgctggaagg cggcgggcca ttaccaggcc     2580
gaagcagcgt tgttgcagtg cacggcagat acacttgctg atgcggtgct gattacgacc     2640
gctcacgcgt ggcagcatca ggggaaaacc ttatttatca gccggaaaac ctaccggatt     2700
gatggtagtg gtcaaatggc gattaccgtt gatgttgaag tggcgagcga tacaccgcat     2760
ccggcgcgga ttggcctgaa ctgccagctg gcgcaggtag cagagcgggt aaactggctc     2820
```

```
ggattagggc cgcaagaaaa ctatcccgac cgccttactg ccgcctgttt tgaccgctgg    2880
gatctgccat tgtcagacat gtatacccg tacgtcttcc cgagcgaaaa cggtctgcgc    2940
tgcgggacgc gcgaattgaa ttatggccca caccagtggc gcggcgactt ccagttcaac    3000
atcagccgct acagtcaaca gcaactgatg gaaaccagcc atcgccatct gctgcacgcg    3060
gaagaaggca catggctgaa atcgacggt tccatatgg ggattggtgg cgacgactcc     3120
tggagcccgt cagtatcggc ggaattccag ctgagcgccg tcgctacca ttaccagttg     3180 gtctggtgtc aaaaactcga gcaccaccac caccaccac                          3219
```

<210> SEQ ID NO 16
<211> LENGTH: 1073
<212> TYPE: PRT
<213> ORGANISM: Artificial Sequence
<220> FEATURE:
<223> OTHER INFORMATION: Synthetic peptide

<400> SEQUENCE: 16

```
Met Ile Lys Ile Ala Thr Arg Lys Tyr Leu Gly Lys Gln Asn Val Tyr
1               5                   10                  15

Gly Ile Gly Val Glu Arg Asp His Asn Phe Ala Leu Lys Asn Gly Phe
            20                  25                  30

Ile Ala Ser Asn Cys Phe Asn Ala Ser Met Thr Met Ile Thr Asp Ser
        35                  40                  45

Leu Ala Val Val Leu Gln Arg Arg Asp Trp Glu Asn Pro Gly Val Thr
    50                  55                  60

Gln Leu Asn Arg Leu Ala Ala His Pro Pro Phe Ala Ser Trp Arg Asn
65                  70                  75                  80

Ser Glu Glu Ala Arg Thr Asp Arg Pro Ser Gln Gln Leu Arg Ser Leu
                85                  90                  95

Asn Gly Glu Trp Arg Phe Ala Trp Phe Pro Ala Pro Glu Ala Val Pro
            100                 105                 110

Glu Ser Trp Leu Glu Cys Asp Leu Pro Glu Ala Asp Thr Val Val Val
        115                 120                 125

Pro Ser Asn Trp Gln Met His Gly Tyr Asp Ala Pro Ile Tyr Thr Asn
    130                 135                 140

Val Thr Tyr Pro Ile Thr Val Asn Pro Pro Phe Val Pro Thr Glu Asn
145                 150                 155                 160

Pro Thr Gly Cys Tyr Ser Leu Thr Phe Asn Val Asp Glu Ser Trp Leu
                165                 170                 175

Gln Glu Gly Gln Thr Arg Ile Ile Phe Asp Gly Val Asn Ser Ala Phe
            180                 185                 190

His Leu Trp Cys Asn Gly Arg Trp Val Gly Tyr Gly Gln Asp Ser Arg
        195                 200                 205

Leu Pro Ser Glu Phe Asp Leu Ser Ala Phe Leu Arg Ala Gly Glu Asn
    210                 215                 220

Arg Leu Ala Val Met Val Leu Arg Trp Ser Asp Gly Ser Tyr Leu Glu
225                 230                 235                 240

Asp Gln Asp Met Trp Arg Met Ser Gly Ile Phe Arg Asp Val Ser Leu
                245                 250                 255

Leu His Lys Pro Thr Thr Gln Ile Ser Asp Phe His Val Ala Thr Arg
            260                 265                 270

Phe Asn Asp Asp Phe Ser Arg Ala Val Leu Glu Ala Glu Val Gln Met
        275                 280                 285
```

-continued

Cys Gly Glu Leu Arg Asp Tyr Leu Arg Val Thr Val Ser Leu Trp Gln
290                 295                 300

Gly Glu Thr Gln Val Ala Ser Gly Thr Ala Pro Phe Gly Gly Glu Ile
305                 310                 315                 320

Ile Asp Glu Arg Gly Gly Tyr Ala Asp Arg Val Thr Leu Arg Leu Asn
            325                 330                 335

Val Glu Asn Pro Lys Leu Trp Ser Ala Glu Ile Pro Asn Leu Tyr Arg
            340                 345                 350

Ala Val Val Glu Leu His Thr Ala Asp Gly Thr Leu Ile Glu Ala Glu
            355                 360                 365

Ala Cys Asp Val Gly Phe Arg Glu Val Arg Ile Glu Asn Gly Leu Leu
370                 375                 380

Leu Leu Asn Gly Lys Pro Leu Leu Ile Arg Gly Val Asn Arg His Glu
385                 390                 395                 400

His His Pro Leu His Gly Gln Val Met Asp Glu Gln Thr Met Val Gln
                405                 410                 415

Asp Ile Leu Leu Met Lys Gln Asn Asn Phe Asn Ala Val Arg Cys Ser
            420                 425                 430

His Tyr Pro Asn His Pro Leu Trp Tyr Thr Leu Cys Asp Arg Tyr Gly
            435                 440                 445

Leu Tyr Val Val Asp Glu Ala Asn Ile Glu Thr His Gly Met Val Pro
450                 455                 460

Met Asn Arg Leu Thr Asp Asp Pro Arg Trp Leu Pro Ala Met Ser Glu
465                 470                 475                 480

Arg Val Thr Arg Met Val Gln Arg Asp Arg Asn His Pro Ser Val Ile
                485                 490                 495

Ile Trp Ser Leu Gly Asn Glu Ser Gly His Gly Ala Asn His Asp Ala
            500                 505                 510

Leu Tyr Arg Trp Ile Lys Ser Val Asp Pro Ser Arg Pro Val Gln Tyr
            515                 520                 525

Glu Gly Gly Gly Ala Asp Thr Thr Ala Thr Asp Ile Ile Cys Pro Met
530                 535                 540

Tyr Ala Arg Val Asp Glu Asp Gln Pro Phe Pro Ala Val Pro Lys Trp
545                 550                 555                 560

Ser Ile Lys Lys Trp Leu Ser Leu Pro Gly Glu Thr Arg Pro Leu Ile
                565                 570                 575

Leu Cys Glu Tyr Ala His Ala Met Gly Asn Ser Leu Gly Gly Phe Ala
            580                 585                 590

Lys Tyr Trp Gln Ala Phe Arg Gln Tyr Pro Arg Leu Gln Gly Gly Phe
            595                 600                 605

Val Trp Asp Trp Val Asp Gln Ser Leu Ile Lys Tyr Asp Glu Asn Gly
610                 615                 620

Asn Pro Trp Ser Ala Tyr Gly Gly Asp Phe Gly Asp Thr Pro Asn Asp
625                 630                 635                 640

Arg Gln Phe Cys Met Asn Gly Leu Val Phe Ala Asp Arg Thr Pro His
                645                 650                 655

Pro Ala Leu Thr Glu Ala Lys His Gln Gln Gln Phe Phe Gln Phe Arg
            660                 665                 670

Leu Ser Gly Gln Thr Ile Glu Val Thr Ser Glu Tyr Leu Phe Arg His
            675                 680                 685

Ser Asp Asn Glu Leu Leu His Trp Met Val Ala Leu Asp Gly Lys Pro
690                 695                 700

Leu Ala Ser Gly Glu Val Pro Leu Asp Val Ala Pro Gln Gly Lys Gln

```
                705                 710                 715                 720
Leu Ile Glu Leu Pro Glu Leu Pro Gln Pro Glu Ser Ala Gly Gln Leu
                    725                 730                 735

Trp Leu Thr Val Arg Val Val Gln Pro Asn Ala Thr Ala Trp Ser Glu
                740                 745                 750

Ala Gly His Ile Ser Ala Trp Gln Gln Trp Arg Leu Ala Glu Asn Leu
            755                 760                 765

Ser Val Thr Leu Pro Ala Ala Ser His Ala Ile Pro His Leu Thr Thr
770                 775                 780

Ser Glu Met Asp Phe Cys Ile Glu Leu Gly Asn Lys Arg Trp Gln Phe
785                 790                 795                 800

Asn Arg Gln Ser Gly Phe Leu Ser Gln Met Trp Ile Gly Asp Lys Lys
                805                 810                 815

Gln Leu Leu Thr Pro Leu Arg Asp Gln Phe Thr Arg Ala Pro Leu Asp
                820                 825                 830

Asn Asp Ile Gly Val Ser Glu Ala Thr Arg Ile Asp Pro Asn Ala Trp
            835                 840                 845

Val Glu Arg Trp Lys Ala Ala Gly His Tyr Gln Ala Glu Ala Ala Leu
        850                 855                 860

Leu Gln Cys Thr Ala Asp Thr Leu Ala Asp Ala Val Leu Ile Thr Thr
865                 870                 875                 880

Ala His Ala Trp Gln His Gln Gly Lys Thr Leu Phe Ile Ser Arg Lys
                885                 890                 895

Thr Tyr Arg Ile Asp Gly Ser Gly Gln Met Ala Ile Thr Val Asp Val
                900                 905                 910

Glu Val Ala Ser Asp Thr Pro His Pro Ala Arg Ile Gly Leu Asn Cys
        915                 920                 925

Gln Leu Ala Gln Val Ala Glu Arg Val Asn Trp Leu Gly Leu Gly Pro
    930                 935                 940

Gln Glu Asn Tyr Pro Asp Arg Leu Thr Ala Ala Cys Phe Asp Arg Trp
945                 950                 955                 960

Asp Leu Pro Leu Ser Asp Met Tyr Thr Pro Tyr Val Phe Pro Ser Glu
                965                 970                 975

Asn Gly Leu Arg Cys Gly Thr Arg Glu Leu Asn Tyr Gly Pro His Gln
                980                 985                 990

Trp Arg Gly Asp Phe Gln Phe Asn Ile Ser Arg Tyr Ser  Gln Gln Gln
            995                 1000                1005

Leu Met Glu Thr Ser His Arg  His Leu Leu His Ala  Glu Glu Gly
    1010                1015                1020

Thr Trp Leu Asn Ile Asp Gly  Phe His Met Gly Ile  Gly Gly Asp
    1025                1030                1035

Asp Ser Trp Ser Pro Ser Val  Ser Ala Glu Phe Gln  Leu Ser Ala
    1040                1045                1050

Gly Arg Tyr His Tyr Gln Leu  Val Trp Cys Gln Lys  Leu Glu His
    1055                1060                1065

His His  His His His
    1070

<210> SEQ ID NO 17
<211> LENGTH: 804
<212> TYPE: DNA
<213> ORGANISM: Artificial Sequence
<220> FEATURE:
<223> OTHER INFORMATION: Synthetic primer
```

<400> SEQUENCE: 17

```
atgatcaaaa tagccacacg taaatattta ggcaaacaaa atgtctatgg cattggagtt    60
gagcgcgacc ataattttgc actcaaaaat ggcttcatag cttctaattg tttcaatgct   120
agcatggaga aaaaaatcac tggatatacc accgttgata tatcccaatg catcgtaaa   180
gaacattttg aggcatttca gtcagttgct caatgtacct ataaccagac cgttcagctg   240
gatattacgg cctttttaaa gaccgtaaag aaaaataagc acaagtttta tccggccttt   300
attcacattc ttgcccgcct gatgaatgct catccggaat ttcgtatggc aatgaaagac   360
ggtgagctgg tgtatatggga tagtgttcac ccttgttaca ccgttttcca tgagcaaact   420
gaaacgtttt catcgctctg gagtgaatac cacgacgatt tccggcagtt tctacacata   480
tattcgcaag atgtggcgtg ttacggtgaa aacctggcct atttccctaa agggtttatt   540
gagaatatgt ttttcgtctc agccaatccc tgggtgagtt tcaccagttt tgatttaaac   600
gtggccaata tggacaactt cttcgccccc gttttcacca tgggcaaata ttatacgcaa   660
ggcgacaagg tgctgatgcc gctggcgatt caggttcatc atgccgtctg tgatggcttc   720
catgtcggca gaatgcttaa tgaattacaa cagtactgcg atgagtggca gggcggggcg   780
ctcgagcacc accaccacca ccac                                          804
```

<210> SEQ ID NO 18
<211> LENGTH: 268
<212> TYPE: PRT
<213> ORGANISM: Artificial Sequence
<220> FEATURE:
<223> OTHER INFORMATION: Synthetic peptide

<400> SEQUENCE: 18

```
Met Ile Lys Ile Ala Thr Arg Lys Tyr Leu Gly Lys Gln Asn Val Tyr
  1               5                  10                  15

Gly Ile Gly Val Glu Arg Asp His Asn Phe Ala Leu Lys Asn Gly Phe
             20                  25                  30

Ile Ala Ser Asn Cys Phe Asn Ala Ser Met Glu Lys Lys Ile Thr Gly
         35                  40                  45

Tyr Thr Thr Val Asp Ile Ser Gln Trp His Arg Lys Glu His Phe Glu
     50                  55                  60

Ala Phe Gln Ser Val Ala Gln Cys Thr Tyr Asn Gln Thr Val Gln Leu
 65                  70                  75                  80

Asp Ile Thr Ala Phe Leu Lys Thr Val Lys Lys Asn Lys His Lys Phe
                 85                  90                  95

Tyr Pro Ala Phe Ile His Ile Leu Ala Arg Leu Met Asn Ala His Pro
            100                 105                 110

Glu Phe Arg Met Ala Met Lys Asp Gly Glu Leu Val Ile Trp Asp Ser
        115                 120                 125

Val His Pro Cys Tyr Thr Val Phe His Glu Gln Thr Glu Thr Phe Ser
    130                 135                 140

Ser Leu Trp Ser Glu Tyr His Asp Asp Phe Arg Gln Phe Leu His Ile
145                 150                 155                 160

Tyr Ser Gln Asp Val Ala Cys Tyr Gly Glu Asn Leu Ala Tyr Phe Pro
                165                 170                 175

Lys Gly Phe Ile Glu Asn Met Phe Phe Val Ser Ala Asn Pro Trp Val
            180                 185                 190

Ser Phe Thr Ser Phe Asp Leu Asn Val Ala Asn Met Asp Asn Phe Phe
        195                 200                 205
```

Ala Pro Val Phe Thr Met Gly Lys Tyr Tyr Thr Gln Gly Asp Lys Val
        210                 215                 220

Leu Met Pro Leu Ala Ile Gln Val His His Ala Val Cys Asp Gly Phe
225                 230                 235                 240

His Val Gly Arg Met Leu Asn Glu Leu Gln Gln Tyr Cys Asp Glu Trp
                245                 250                 255

Gln Gly Gly Ala Leu Glu His His His His His His
            260                 265

<210> SEQ ID NO 19
<211> LENGTH: 1311
<212> TYPE: DNA
<213> ORGANISM: Artificial Sequence
<220> FEATURE:
<223> OTHER INFORMATION: Synthetic primer

<400> SEQUENCE: 19

| | | | | | |
|---|---|---|---|---|---|
| atgatcaaaa | tagccacacg | taaatattta | ggcaaacaaa | atgtctatgg cattggagtt | 60 |
| gagcgcgacc | ataattttgc | actcaaaaat | ggcttcatag | cttctaattg tttcaatgct | 120 |
| agcatgaaaa | tcgaagaagg | taaactggta | atctggatta | acggcgataa aggctataac | 180 |
| ggtctcgctg | aagtcggtaa | gaaattcgag | aaagataccg | gaattaaagt caccgttgag | 240 |
| catccggata | aactggaaga | gaaattccca | caggttgcgg | caactggcga tggccctgac | 300 |
| attatcttct | gggcacacga | ccgctttggt | ggctacgctc | aatctggcct gttggctgaa | 360 |
| atcaccccgg | acaaagcgtt | ccaggacaag | ctgtatccgt | ttacctggga tgccgtacgt | 420 |
| tacaacggca | agctgattgc | ttacccgatc | gctgttgaag | cgttatcgct gatttataac | 480 |
| aaagatctgc | tgccgaaccc | gccaaaaacc | tgggaagaga | tcccggcgct ggataaagaa | 540 |
| ctgaaagcga | aggtaagag | cgcgctgatg | ttcaacctgc | aagaaccgta cttcacctgg | 600 |
| ccgctgattg | ctgctgacgg | gggttatgcg | ttcaagtatg | aaaacggcaa gtacgacatt | 660 |
| aaagacgtgg | gcgtggataa | cgctggcgcg | aaagcgggtc | tgaccttcct ggttgacctg | 720 |
| attaaaaaca | acacatgaa | tgcagacacc | gattactcca | tcgcagaagc tgcctttaat | 780 |
| aaaggcgaaa | cagcgatgac | catcaacggc | ccgtgggcat | ggtccaacat cgacaccagc | 840 |
| aaagtgaatt | atggtgtaac | ggtactgccg | accttcaagg | gtcaaccatc caaaccgttc | 900 |
| gttggcgtgc | tgagcgcagg | tattaacgcc | gccagtccga | acaaagagct ggcaaaagag | 960 |
| ttcctcgaaa | actatctgct | gactgatgaa | ggtctggaag | cggttaataa agacaaaccg | 1020 |
| ctgggtgccg | tagcgctgaa | gtcttacgag | aagagttgg | cgaaagatcc acgtattgcc | 1080 |
| gccaccatgg | aaaacgccca | gaaaggtgaa | atcatgccga | acatcccgca gatgtccgct | 1140 |
| ttctggtatg | ccgtgcgtac | tgcggtgatc | aacgccgcca | gcggtcgtca gactgtcgat | 1200 |
| gaagccctga | agacgcgca | gactaattcg | agctcgaaca | caacaacaa taacaataac | 1260 |
| aacaacctcg | ggatcgaggg | aaggggactc | gagcaccacc | accaccacca c | 1311 |

<210> SEQ ID NO 20
<211> LENGTH: 437
<212> TYPE: PRT
<213> ORGANISM: Artificial Sequence
<220> FEATURE:
<223> OTHER INFORMATION: Synthetic peptide

<400> SEQUENCE: 20

Met Ile Lys Ile Ala Thr Arg Lys Tyr Leu Gly Lys Gln Asn Val Tyr
1               5                   10                  15

```
Gly Ile Gly Val Glu Arg Asp His Asn Phe Ala Leu Lys Asn Gly Phe
                20                  25                  30
Ile Ala Ser Asn Cys Phe Asn Ala Ser Met Lys Ile Glu Glu Gly Lys
            35                  40                  45
Leu Val Ile Trp Ile Asn Gly Asp Lys Gly Tyr Asn Gly Leu Ala Glu
    50                  55                  60
Val Gly Lys Lys Phe Glu Lys Asp Thr Gly Ile Lys Val Thr Val Glu
65                  70                  75                  80
His Pro Asp Lys Leu Glu Glu Lys Phe Pro Gln Val Ala Ala Thr Gly
                85                  90                  95
Asp Gly Pro Asp Ile Ile Phe Trp Ala His Asp Arg Phe Gly Gly Tyr
            100                 105                 110
Ala Gln Ser Gly Leu Leu Ala Glu Ile Thr Pro Asp Lys Ala Phe Gln
    115                 120                 125
Asp Lys Leu Tyr Pro Phe Thr Trp Asp Ala Val Arg Tyr Asn Gly Lys
130                 135                 140
Leu Ile Ala Tyr Pro Ile Ala Val Glu Ala Leu Ser Leu Ile Tyr Asn
145                 150                 155                 160
Lys Asp Leu Leu Pro Asn Pro Pro Lys Thr Trp Glu Glu Ile Pro Ala
                165                 170                 175
Leu Asp Lys Glu Leu Lys Ala Lys Gly Lys Ser Ala Leu Met Phe Asn
            180                 185                 190
Leu Gln Glu Pro Tyr Phe Thr Trp Pro Leu Ile Ala Ala Asp Gly Gly
    195                 200                 205
Tyr Ala Phe Lys Tyr Glu Asn Gly Lys Tyr Asp Ile Lys Asp Val Gly
210                 215                 220
Val Asp Asn Ala Gly Ala Lys Ala Gly Leu Thr Phe Leu Val Asp Leu
225                 230                 235                 240
Ile Lys Asn Lys His Met Asn Ala Asp Thr Asp Tyr Ser Ile Ala Glu
                245                 250                 255
Ala Ala Phe Asn Lys Gly Glu Thr Ala Met Thr Ile Asn Gly Pro Trp
            260                 265                 270
Ala Trp Ser Asn Ile Asp Thr Ser Lys Val Asn Tyr Gly Val Thr Val
    275                 280                 285
Leu Pro Thr Phe Lys Gly Gln Pro Ser Lys Pro Phe Val Gly Val Leu
290                 295                 300
Ser Ala Gly Ile Asn Ala Ala Ser Pro Asn Lys Glu Leu Ala Lys Glu
305                 310                 315                 320
Phe Leu Glu Asn Tyr Leu Leu Thr Asp Glu Gly Leu Glu Ala Val Asn
                325                 330                 335
Lys Asp Lys Pro Leu Gly Ala Val Ala Leu Lys Ser Tyr Glu Glu Glu
            340                 345                 350
Leu Ala Lys Asp Pro Arg Ile Ala Ala Thr Met Glu Asn Ala Gln Lys
    355                 360                 365
Gly Glu Ile Met Pro Asn Ile Pro Gln Met Ser Ala Phe Trp Tyr Ala
370                 375                 380
Val Arg Thr Ala Val Ile Asn Ala Ala Ser Gly Arg Gln Thr Val Asp
385                 390                 395                 400
Glu Ala Leu Lys Asp Ala Gln Thr Asn Ser Ser Ser Asn Asn Asn Asn
                405                 410                 415
Asn Asn Asn Asn Asn Asn Leu Gly Ile Glu Gly Arg Gly Leu Glu His
            420                 425                 430
His His His His His
```

<210> SEQ ID NO 21
<211> LENGTH: 555
<212> TYPE: DNA
<213> ORGANISM: Artificial Sequence
<220> FEATURE:
<223> OTHER INFORMATION: Synthetic primer

<400> SEQUENCE: 21

```
atgtgtttaa gctatgaaac ggaaatattg acagtagaat atggattatt accgattggt      60
aaaattgtag aaaagcgcat cgaatgtact gtttatagcg ttgataataa tggaaatatt     120
tatacacaac ctgtagcaca atggcacgat cgcggagaac aagaggtgtt tgagtattgt     180
ttggaagatg gttcattgat tcgggcaaca aaagaccata agtttatgac tgttgatggt     240
caaatgttgc caattgatga atatttgaa cgtgaattgg atttgatgcg ggttgataat      300
ttgccgaata agcttggagg cggagggagc ggaggcggag ggagcgctag catgaaaatc     360
gaagaaggta aactgacaaa tcctggtgta tccgcttggc aggtcaacac agcttatact     420
gcgggacaat tggtcacata taacggcaag acgtataaat gtttgcagcc ccacacctcc     480
ttggcaggat gggaaccatc caacgttcct gccttgtggc agcttcaact cgagcaccac     540
caccaccacc actga                                                      555
```

<210> SEQ ID NO 22
<211> LENGTH: 184
<212> TYPE: PRT
<213> ORGANISM: Artificial Sequence
<220> FEATURE:
<223> OTHER INFORMATION: Synthetic peptide

<400> SEQUENCE: 22

```
Met Cys Leu Ser Tyr Glu Thr Glu Ile Leu Thr Val Glu Tyr Gly Leu
  1               5                  10                  15

Leu Pro Ile Gly Lys Ile Val Glu Lys Arg Ile Glu Cys Thr Val Tyr
             20                  25                  30

Ser Val Asp Asn Asn Gly Asn Ile Tyr Thr Gln Pro Val Ala Gln Trp
         35                  40                  45

His Asp Arg Gly Glu Gln Glu Val Phe Glu Tyr Cys Leu Glu Asp Gly
     50                  55                  60

Ser Leu Ile Arg Ala Thr Lys Asp His Lys Phe Met Thr Val Asp Gly
 65                  70                  75                  80

Gln Met Leu Pro Ile Asp Glu Ile Phe Glu Arg Glu Leu Asp Leu Met
                 85                  90                  95

Arg Val Asp Asn Leu Pro Asn Lys Leu Gly Gly Gly Ser Gly Gly
            100                 105                 110

Gly Gly Ser Ala Ser Met Lys Ile Glu Glu Gly Lys Leu Thr Asn Pro
        115                 120                 125

Gly Val Ser Ala Trp Gln Val Asn Thr Ala Tyr Thr Ala Gly Gln Leu
    130                 135                 140

Val Thr Tyr Asn Gly Lys Thr Tyr Lys Cys Leu Gln Pro His Thr Ser
145                 150                 155                 160

Leu Ala Gly Trp Glu Pro Ser Asn Val Pro Ala Leu Trp Gln Leu Gln
                165                 170                 175

Leu Glu His His His His His His
            180
```

<210> SEQ ID NO 23
<211> LENGTH: 555
<212> TYPE: DNA
<213> ORGANISM: Artificial Sequence
<220> FEATURE:
<223> OTHER INFORMATION: Synthetic primer

<400> SEQUENCE: 23

```
atggctttaa gctatgaaac ggaaatattg acagtagaat atggattatt accgattggt      60
aaaattgtag aaaagcgcat cgaatgtact gtttatagcg ttgataataa tggaaatatt     120
tatacacaac ctgtagcaca atggcacgat cgcggagaac aagaggtgtt tgagtattgt     180
ttggaagatg gttcattgat tcggcaacaa aaagaccata agtttatgac tgttgatggt     240
caaatgttgc caattgatga atatttgaa cgtgaattgg atttgatgcg ggttgataat     300
ttgccgaata gcttggagg cggagggagc ggaggcggag ggagcgctag catgaaaatc     360
gaagaaggta aactgacaaa tcctggtgta tccgcttggc aggtcaacac agcttatact     420
gcgggacaat tggtcacata acggcaag acgtataaat gtttgcagcc ccacacctcc     480
ttggcaggat gggaaccatc caacgttcct gccttgtggc agcttcaact cgagcaccac     540
caccaccacc actga                                                     555
```

<210> SEQ ID NO 24
<211> LENGTH: 184
<212> TYPE: PRT
<213> ORGANISM: Artificial Sequence
<220> FEATURE:
<223> OTHER INFORMATION: Synthetic peptide

<400> SEQUENCE: 24

```
Met Ala Leu Ser Tyr Glu Thr Glu Ile Leu Thr Val Glu Tyr Gly Leu
1               5                   10                  15
Leu Pro Ile Gly Lys Ile Val Glu Lys Arg Ile Glu Cys Thr Val Tyr
            20                  25                  30
Ser Val Asp Asn Asn Gly Asn Ile Tyr Thr Gln Pro Val Ala Gln Trp
        35                  40                  45
His Asp Arg Gly Glu Gln Glu Val Phe Glu Tyr Cys Leu Glu Asp Gly
    50                  55                  60
Ser Leu Ile Arg Ala Thr Lys Asp His Lys Phe Met Thr Val Asp Gly
65                  70                  75                  80
Gln Met Leu Pro Ile Asp Glu Ile Phe Glu Arg Glu Leu Asp Leu Met
                85                  90                  95
Arg Val Asp Asn Leu Pro Asn Lys Leu Gly Gly Gly Ser Gly Gly
            100                 105                 110
Gly Gly Ser Ala Ser Met Lys Ile Glu Glu Gly Lys Leu Thr Asn Pro
        115                 120                 125
Gly Val Ser Ala Trp Gln Val Asn Thr Ala Tyr Thr Ala Gly Gln Leu
    130                 135                 140
Val Thr Tyr Asn Gly Lys Thr Tyr Lys Cys Leu Gln Pro His Thr Ser
145                 150                 155                 160
Leu Ala Gly Trp Glu Pro Ser Asn Val Pro Ala Leu Trp Gln Leu Gln
                165                 170                 175
Leu Glu His His His His His His
            180
```

<210> SEQ ID NO 25
<211> LENGTH: 1155
<212> TYPE: DNA

<213> ORGANISM: Artificial Sequence
<220> FEATURE:
<223> OTHER INFORMATION: Synthetic primer

<400> SEQUENCE: 25

```
atgatcaaaa tagccacacg taaatatta ggcaaacaaa atgtctatga cattggagtt      60
gagcgcgacc ataattttgc actcaaaaat ggcttcatag cttctaattg tttcaatgct    120
agcatgctgc cgaaactcgt tataactcac cgagtacacg aagagatcct gcaactgctg    180
gcgccacatt gcgagctgat aaccaaccag accgacagca cgctgacgcg cgaggaaatt    240
ctgcgccgct gtcgcgatgc tcaggcgatg atggcgttca tgcccgatcg ggtcgatgca    300
gactttcttc aagcctgccc tgagctgcgt gtaatcggct gcgcgctcaa gggcttcgac    360
aatttcgatg tggacgcctg tactgcccgc ggggtctggc tgaccttcgt gcctgatctg    420
ttgacggtcc cgactgccga gctggcgatc ggactggcgg tggggctggg gcggcatctg    480
cgggcagcag atgcgttcgt ccgctctggc aagttccggg gctggcaacc acggttctac    540
ggcacggggc tggataacgc tacggtcggc ttccttggca tgggcgccat cggactggcc    600
atggctgatc gcttgcaggg atggggcgcg accctgcagt accacgcgcg gaaggctctg    660
gatacacaaa ccgagcaacg gctcggcctg cgccaggtgg cgtgcagcga actcttcgcc    720
agctcggact tcatcctgct ggcgcttccc ttgaatgccg ataccctgca tctggtcaac    780
gccgagctgc ttgccctcgt acggccgggc gctctgcttg taaaccctg tcgtggctcg    840
gtagtggatg aagccgccgt gctcgcggcg cttgagcgag ccagctcgg cgggtatgcg    900
gcggatgtat tcgaaatgga agactgggct cgcgcggacc ggccgcagca gatcgatcct    960
gcgctgctcg cgcatccgaa tacgctgttc actccgcaca tagggtcggc agtgcgcgcg   1020
gtgcgcctgg agattgaacg ttgtgcagcg cagaacatcc tccaggcatt ggcaggtgag   1080
cgcccaatca acgctgtgaa ccgtctgccc aaggccaatc ctgccgcaga cctcgagcac   1140
caccaccacc accac                                                    1155
```

<210> SEQ ID NO 26
<211> LENGTH: 385
<212> TYPE: PRT
<213> ORGANISM: Artificial Sequence
<220> FEATURE:
<223> OTHER INFORMATION: Synthetic peptide

<400> SEQUENCE: 26

```
Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Asn Cys Phe Asn Ala Ser Met Leu Pro Lys Leu Val Ile
        35                  40                  45

Thr His Arg Val His Glu Glu Ile Leu Gln Leu Leu Ala Pro His Cys
    50                  55                  60

Glu Leu Ile Thr Asn Gln Thr Asp Ser Thr Leu Thr Arg Glu Glu Ile
65                  70                  75                  80

Leu Arg Arg Cys Arg Asp Ala Gln Ala Met Met Ala Phe Met Pro Asp
                85                  90                  95

Arg Val Asp Ala Asp Phe Leu Gln Ala Cys Pro Glu Leu Arg Val Ile
            100                 105                 110

Gly Cys Ala Leu Lys Gly Phe Asp Asn Phe Asp Val Asp Ala Cys Thr
        115                 120                 125
```

```
Ala Arg Gly Val Trp Leu Thr Phe Val Pro Asp Leu Leu Thr Val Pro
            130                 135                 140

Thr Ala Glu Leu Ala Ile Gly Leu Ala Val Gly Leu Gly Arg His Leu
145                 150                 155                 160

Arg Ala Ala Asp Ala Phe Val Arg Ser Gly Lys Phe Arg Gly Trp Gln
                165                 170                 175

Pro Arg Phe Tyr Gly Thr Gly Leu Asp Asn Ala Thr Val Gly Phe Leu
            180                 185                 190

Gly Met Gly Ala Ile Gly Leu Ala Met Ala Asp Arg Leu Gln Gly Trp
        195                 200                 205

Gly Ala Thr Leu Gln Tyr His Ala Arg Lys Ala Leu Asp Thr Gln Thr
    210                 215                 220

Glu Gln Arg Leu Gly Leu Arg Gln Val Ala Cys Ser Glu Leu Phe Ala
225                 230                 235                 240

Ser Ser Asp Phe Ile Leu Leu Ala Leu Pro Leu Asn Ala Asp Thr Leu
                245                 250                 255

His Leu Val Asn Ala Glu Leu Ala Leu Val Arg Pro Gly Ala Leu
            260                 265                 270

Leu Val Asn Pro Cys Arg Gly Ser Val Val Asp Glu Ala Ala Val Leu
        275                 280                 285

Ala Ala Leu Glu Arg Gly Gln Leu Gly Gly Tyr Ala Ala Asp Val Phe
    290                 295                 300

Glu Met Glu Asp Trp Ala Arg Ala Asp Arg Pro Gln Gln Ile Asp Pro
305                 310                 315                 320

Ala Leu Leu Ala His Pro Asn Thr Leu Phe Thr Pro His Ile Gly Ser
                325                 330                 335

Ala Val Arg Ala Val Arg Leu Glu Ile Glu Arg Cys Ala Ala Gln Asn
            340                 345                 350

Ile Leu Gln Ala Leu Ala Gly Glu Arg Pro Ile Asn Ala Val Asn Arg
        355                 360                 365

Leu Pro Lys Ala Asn Pro Ala Ala Asp Leu Glu His His His His His
    370                 375                 380

His
385

<210> SEQ ID NO 27
<211> LENGTH: 849
<212> TYPE: DNA
<213> ORGANISM: Artificial Sequence
<220> FEATURE:
<223> OTHER INFORMATION: Synthetic primer

<400> SEQUENCE: 27
atgatcaaaa tagccacacg taaatattta ggcaaacaaa atgtctatgg cattggagtt     60
gagcgcgacc ataattttgc actcaaaaat ggcttcatag cttctaatgc gttcaatgtg    120
agcaagggcg aggagctgtt caccggggtg gtgcccatcc tggtcgagct ggacggcgac    180
gtaaacggcc acaagttcag cgtgtccggc gagggcgagg gcgatgccac ctacggcaag    240
ctgaccctga agttcatctg caccaccggc aagctgcccg tgccctggcc caccctcgtg    300
accaccctga cctacggcgt gcagtgcttc agccgctacc ccgaccacat gaagcagcac    360
gacttcttca gtccgccat gcccgaaggc tacgtccagg agcgcaccat cttcttcaag    420
gacgacggca actacaagac ccgcgccgag gtgaagttcg agggcgacac cctggtgaac    480
cgcatcgagc tgaagggcat cgacttcaag gaggacggca acatcctggg gcacaagctg    540
```

```
gagtacaact acaacagcca caacgtctat atcatggccg acaagcagaa gaacggcatc      600
aaggtgaact tcaagatccg ccacaacatc gaggacggca gcgtgcagct cgccgaccac      660
taccagcaga acacccccat cggcgacggc cccgtgctgc tgcccgacaa ccactacctg      720
agcacccagt ccgccctgag caaagacccc aacgagaagc gcgatcacat ggtcctgctg      780
gagttcgtga ccgccgccgg gatcactctc ggcatggacg agttactcga gcaccaccac      840
caccaccac                                                              849
```

<210> SEQ ID NO 28
<211> LENGTH: 283
<212> TYPE: PRT
<213> ORGANISM: Artificial Sequence
<220> FEATURE:
<223> OTHER INFORMATION: Synthetic peptide

<400> SEQUENCE: 28

```
Met Ile Lys Ile Ala Thr Arg Lys Tyr Leu Gly Lys Gln Asn Val Tyr
 1               5                   10                  15

Gly Ile Gly Val Glu Arg Asp His Asn Phe Ala Leu Lys Asn Gly Phe
            20                  25                  30

Ile Ala Ser Asn Ala Phe Asn Val Ser Lys Gly Glu Glu Leu Phe Thr
        35                  40                  45

Gly Val Val Pro Ile Leu Val Glu Leu Asp Gly Asp Val Asn Gly His
    50                  55                  60

Lys Phe Ser Val Ser Gly Glu Gly Glu Gly Asp Ala Thr Tyr Gly Lys
65                  70                  75                  80

Leu Thr Leu Lys Phe Ile Cys Thr Thr Gly Lys Leu Pro Val Pro Trp
                85                  90                  95

Pro Thr Leu Val Thr Thr Leu Thr Tyr Gly Val Gln Cys Phe Ser Arg
            100                 105                 110

Tyr Pro Asp His Met Lys Gln His Asp Phe Phe Lys Ser Ala Met Pro
        115                 120                 125

Glu Gly Tyr Val Gln Glu Arg Thr Ile Phe Phe Lys Asp Asp Gly Asn
    130                 135                 140

Tyr Lys Thr Arg Ala Glu Val Lys Phe Glu Gly Asp Thr Leu Val Asn
145                 150                 155                 160

Arg Ile Glu Leu Lys Gly Ile Asp Phe Lys Glu Asp Gly Asn Ile Leu
                165                 170                 175

Gly His Lys Leu Glu Tyr Asn Tyr Asn Ser His Asn Val Tyr Ile Met
            180                 185                 190

Ala Asp Lys Gln Lys Asn Gly Ile Lys Val Asn Phe Lys Ile Arg His
        195                 200                 205

Asn Ile Glu Asp Gly Ser Val Gln Leu Ala Asp His Tyr Gln Gln Asn
    210                 215                 220

Thr Pro Ile Gly Asp Gly Pro Val Leu Leu Pro Asp Asn His Tyr Leu
225                 230                 235                 240

Ser Thr Gln Ser Ala Leu Ser Lys Asp Pro Asn Glu Lys Arg Asp His
                245                 250                 255

Met Val Leu Leu Glu Phe Val Thr Ala Ala Gly Ile Thr Leu Gly Met
            260                 265                 270

Asp Glu Leu Leu Glu His His His His His His
        275                 280
```

<210> SEQ ID NO 29

<211> LENGTH: 849
<212> TYPE: DNA
<213> ORGANISM: Artificial Sequence
<220> FEATURE:
<223> OTHER INFORMATION: Synthetic primer

<400> SEQUENCE: 29

```
atgatcaaaa tagccacacg taaatattta ggcaaacaaa atgtctatgg cattggagtt      60
gagcgcgacc ataattttgc actcaaaaat ggcttcatag cttctaatga tttcaatgtg     120
agcaagggcg aggagctgtt caccggggtg gtgcccatcc tggtcgagct ggacggcgac     180
gtaaacggcc acaagttcag cgtgtccggc gagggcgagg gcgatgccac ctacggcaag     240
ctgaccctga agttcatctg caccaccggc aagctgcccg tgcctggcc caccctcgtg      300
accaccctga cctacggcgt gcagtgcttc agccgctacc ccgaccacat gaagcagcac     360
gacttcttca gtccgccat gcccgaaggc tacgtccagg agcgcaccat cttcttcaag      420
gacgacggca actacaagac ccgcgccgag gtgaagttcg agggcgacac cctggtgaac     480
cgcatcgagc tgaagggcat cgacttcaag gaggacggca catcctggg gcacaagctg      540
gagtacaact acaacagcca caacgtctat atcatggccg acaagcagaa gaacggcatc     600
aaggtgaact tcaagatccg ccacaacatc gaggacggca gcgtgcagct cgccgaccac     660
taccagcaga acacccccat cggcgacggc cccgtgctgc tgcccgacaa ccactacctg     720
agcacccagt ccgccctgag caaagacccc aacgagaagc gcgatcacat ggtcctgctg     780
gagttcgtga ccgccgccgg gatcactctc ggcatggacg agttactcga gcaccaccac     840
caccaccac                                                             849
```

<210> SEQ ID NO 30
<211> LENGTH: 280
<212> TYPE: PRT
<213> ORGANISM: Artificial Sequence
<220> FEATURE:
<223> OTHER INFORMATION: Synthetic peptide

<400> SEQUENCE: 30

```
Met Ile Lys Ile Ala Thr Arg Lys Tyr Leu Gly Lys Gln Asn Val Tyr
1               5                   10                  15

Gly Ile Gly Val Glu Arg Asp His Asn Phe Ala Leu Lys Asn Gly Phe
            20                  25                  30

Ile Ala Ser Asn Asp Phe Asn Val Ser Lys Gly Glu Glu Leu Phe Thr
        35                  40                  45

Gly Val Val Pro Ile Leu Val Glu Leu Asp Gly Asp Val Asn Gly His
    50                  55                  60

Lys Phe Ser Val Ser Gly Glu Gly Glu Gly Asp Ala Thr Tyr Gly Lys
65                  70                  75                  80

Leu Thr Leu Lys Phe Ile Cys Thr Thr Gly Lys Leu Pro Val Pro Trp
                85                  90                  95

Pro Thr Leu Val Thr Thr Leu Thr Tyr Gly Val Gln Cys Phe Ser Arg
            100                 105                 110

Tyr Pro Asp His Met Lys Gln His Asp Phe Phe Lys Ser Ala Met Pro
        115                 120                 125

Glu Gly Tyr Val Gln Glu Arg Thr Ile Phe Phe Lys Asp Asp Gly Asn
    130                 135                 140

Tyr Lys Thr Arg Ala Glu Val Lys Phe Glu Gly Asp Thr Leu Val Asn
145                 150                 155                 160

Arg Ile Glu Leu Lys Gly Ile Asp Phe Lys Glu Asp Gly Asn Ile Leu
```

```
                    165                 170                 175
Gly His Lys Leu Glu Tyr Asn Tyr Asn Ser His Asn Val Tyr Ile Met
                180                 185                 190

Ala Asp Lys Gln Lys Asn Gly Ile Lys Val Asn Phe Lys Ile Arg His
            195                 200                 205

Asn Ile Glu Asp Gly Ser Val Gln Leu Ala Asp His Tyr Gln Gln Asn
        210                 215                 220

Thr Pro Ile Gly Asp Gly Pro Val Leu Pro Asp Asn His Tyr Leu
225                 230                 235                 240

Ser Thr Gln Ser Ala Leu Ser Lys Asp Pro Asn Glu Lys Arg Asp His
                245                 250                 255

Met Val Leu Leu Glu Phe Val Thr Ala Ala Gly Ile Thr Leu Gly Met
            260                 265                 270

Asp Glu Leu Leu Glu His His His
        275                 280

<210> SEQ ID NO 31
<211> LENGTH: 849
<212> TYPE: DNA
<213> ORGANISM: Artificial Sequence
<220> FEATURE:
<223> OTHER INFORMATION: Synthetic primer

<400> SEQUENCE: 31
atgatcaaaa tagccacacg taaatattta ggcaaacaaa atgtctatgg cattggagtt    60
gagcgcgacc ataattttgc actcaaaaat ggcttcatag cttctaatct gttcaatgtg   120
agcaagggcg aggagctgtt caccggggtg gtgcccatcc tggtcgagct ggacggcgac   180
gtaaacggcc acaagttcag cgtgtccggc gagggcgagg gcgatgccac ctacggcaag   240
ctgaccctga agttcatctg caccaccggc aagctgcccg tgcctggcc caccctcgtg   300 accaccctga cctacggcgt gcagtgcttc agccgctacc ccgaccacat gaagcagcac   360
gacttcttca agtccgccat gcccgaaggc tacgtccagg agcgcaccat cttcttcaag   420
gacgacggca actacaagac ccgcgccgag gtgaagttcg agggcgacac cctggtgaac   480
cgcatcgagc tgaagggcat cgacttcaag gaggacggca acatcctggg cacaagctg    540 gagtacaact acaacagcca caacgtctat atcatggccg acaagcagaa gaacggcatc   600
aaggtgaact tcaagatccg ccacaacatc gaggacggca gcgtgcagct cgccgaccac   660
taccagcaga cacccccat cggcgacggc ccgtgctgc tgcccgacaa ccactacctg     720
agcacccagt ccgccctgag caaagacccc aacgagaagc gcgatcacat ggtcctgctg   780
gagttcgtga ccgccgccgg gatcactctc ggcatggacg agttactcga gcaccaccac   840
caccaccac                                                            849

<210> SEQ ID NO 32
<211> LENGTH: 283
<212> TYPE: PRT
<213> ORGANISM: Artificial Sequence
<220> FEATURE:
<223> OTHER INFORMATION: Synthetic peptide

<400> SEQUENCE: 32

Met Ile Lys Ile Ala Thr Arg Lys Tyr Leu Gly Lys Gln Asn Val Tyr
1               5                   10                  15

Gly Ile Gly Val Glu Arg Asp His Asn Phe Ala Leu Lys Asn Gly Phe
            20                  25                  30
```

Ile Ala Ser Asn Leu Phe Asn Val Ser Lys Gly Glu Glu Leu Phe Thr
             35                  40                  45

Gly Val Val Pro Ile Leu Val Glu Leu Asp Gly Asp Val Asn Gly His
 50                  55                  60

Lys Phe Ser Val Ser Gly Glu Gly Glu Gly Asp Ala Thr Tyr Gly Lys
 65                  70                  75                  80

Leu Thr Leu Lys Phe Ile Cys Thr Thr Gly Lys Leu Pro Val Pro Trp
                 85                  90                  95

Pro Thr Leu Val Thr Thr Leu Thr Tyr Gly Val Gln Cys Phe Ser Arg
                100                 105                 110

Tyr Pro Asp His Met Lys Gln His Asp Phe Phe Lys Ser Ala Met Pro
            115                 120                 125

Glu Gly Tyr Val Gln Glu Arg Thr Ile Phe Phe Lys Asp Asp Gly Asn
        130                 135                 140

Tyr Lys Thr Arg Ala Glu Val Lys Phe Glu Gly Asp Thr Leu Val Asn
145                 150                 155                 160

Arg Ile Glu Leu Lys Gly Ile Asp Phe Lys Glu Asp Gly Asn Ile Leu
                165                 170                 175

Gly His Lys Leu Glu Tyr Asn Tyr Asn Ser His Asn Val Tyr Ile Met
            180                 185                 190

Ala Asp Lys Gln Lys Asn Gly Ile Lys Val Asn Phe Lys Ile Arg His
        195                 200                 205

Asn Ile Glu Asp Gly Ser Val Gln Leu Ala Asp His Tyr Gln Gln Asn
    210                 215                 220

Thr Pro Ile Gly Asp Gly Pro Val Leu Leu Pro Asp Asn His Tyr Leu
225                 230                 235                 240

Ser Thr Gln Ser Ala Leu Ser Lys Asp Pro Asn Glu Lys Arg Asp His
                245                 250                 255

Met Val Leu Leu Glu Phe Val Thr Ala Ala Gly Ile Thr Leu Gly Met
            260                 265                 270

Asp Glu Leu Leu Glu His His His His His
275                 280

<210> SEQ ID NO 33
<211> LENGTH: 849
<212> TYPE: DNA
<213> ORGANISM: Artificial Sequence
<220> FEATURE:
<223> OTHER INFORMATION: Synthetic primer

<400> SEQUENCE: 33
atgatcaaaa tagccacacg taaatattta ggcaaacaaa atgtctatgg cattggagtt      60
gagcgcgacc ataattttgc actcaaaaat ggcttcatag cttctaatcc gttcaatgtg     120
agcaagggcg aggagctgtt caccggggtg gtgcccatcc tggtcgagct ggacggcgac     180
gtaaacggcc acaagttcag cgtgtccggc gagggcgagg gcgatgccac ctacggcaag     240
ctgaccctga agttcatctg caccaccggc aagctgcccg tgccctggcc caccctcgtg     300
accaccctga cctacggcgt gcagtgcttc agccgctacc ccgaccacat gaagcagcac     360
gacttcttca gtccgccat gcccgaaggc tacgtccagg agcgcaccat cttcttcaag     420
gacgacggca actacaagac ccgcgccgag gtgaagttcg agggcgacac cctggtgaac     480
cgcatcgagc tgaagggcat cgacttcaag gaggacggca acatcctggg cacaagctg      540 gagtacaact acaacagcca caacgtctat atcatggccg acaagcagaa gaacggcatc     600
aaggtgaact tcaagatccg ccacaacatc gaggacggca gcgtgcagct cgccgaccac     660

```
taccagcaga acacccccat cggcgacggc cccgtgctgc tgcccgacaa ccactacctg    720
agcacccagt ccgccctgag caaagacccc aacgagaagc gcgatcacat ggtcctgctg    780
gagttcgtga ccgccgccgg gatcactctc ggcatggacg agttactcga gcaccaccac    840
caccaccac                                                             849
```

<210> SEQ ID NO 34
<211> LENGTH: 283
<212> TYPE: PRT
<213> ORGANISM: Artificial Sequence
<220> FEATURE:
<223> OTHER INFORMATION: Synthetic peptide

<400> SEQUENCE: 34

```
Met Ile Lys Ile Ala Thr Arg Lys Tyr Leu Gly Lys Gln Asn Val Tyr
1               5                   10                  15

Gly Ile Gly Val Glu Arg Asp His Asn Phe Ala Leu Lys Asn Gly Phe
            20                  25                  30

Ile Ala Ser Asn Pro Phe Asn Val Ser Lys Gly Glu Glu Leu Phe Thr
        35                  40                  45

Gly Val Val Pro Ile Leu Val Glu Leu Asp Gly Asp Val Asn Gly His
    50                  55                  60

Lys Phe Ser Val Ser Gly Glu Gly Glu Gly Asp Ala Thr Tyr Gly Lys
65                  70                  75                  80

Leu Thr Leu Lys Phe Ile Cys Thr Thr Gly Lys Leu Pro Val Pro Trp
                85                  90                  95

Pro Thr Leu Val Thr Thr Leu Thr Tyr Gly Val Gln Cys Phe Ser Arg
            100                 105                 110

Tyr Pro Asp His Met Lys Gln His Asp Phe Phe Lys Ser Ala Met Pro
        115                 120                 125

Glu Gly Tyr Val Gln Glu Arg Thr Ile Phe Phe Lys Asp Asp Gly Asn
    130                 135                 140

Tyr Lys Thr Arg Ala Glu Val Lys Phe Glu Gly Asp Thr Leu Val Asn
145                 150                 155                 160

Arg Ile Glu Leu Lys Gly Ile Asp Phe Lys Glu Asp Gly Asn Ile Leu
                165                 170                 175

Gly His Lys Leu Glu Tyr Asn Tyr Asn Ser His Asn Val Tyr Ile Met
            180                 185                 190

Ala Asp Lys Gln Lys Asn Gly Ile Lys Val Asn Phe Lys Ile Arg His
        195                 200                 205

Asn Ile Glu Asp Gly Ser Val Gln Leu Ala Asp His Tyr Gln Gln Asn
    210                 215                 220

Thr Pro Ile Gly Asp Gly Pro Val Leu Leu Pro Asp Asn His Tyr Leu
225                 230                 235                 240

Ser Thr Gln Ser Ala Leu Ser Lys Asp Pro Asn Glu Lys Arg Asp His
                245                 250                 255

Met Val Leu Leu Glu Phe Val Thr Ala Ala Gly Ile Thr Leu Gly Met
            260                 265                 270

Asp Glu Leu Leu Glu His His His His His
        275                 280
```

<210> SEQ ID NO 35
<211> LENGTH: 849
<212> TYPE: DNA
<213> ORGANISM: Artificial Sequence
<220> FEATURE:

<223> OTHER INFORMATION: Synthetic primer

<400> SEQUENCE: 35

| | |
|---|---:|
| atgatcaaaa tagccacacg taaatattta ggcaaacaaa atgtctatgg cattggagtt | 60 |
| gagcgcgacc ataattttgc actcaaaaat ggcttcatag cttctaatcg tttcaatgtg | 120 |
| agcaagggcg aggagctgtt caccggggtg gtgcccatcc tggtcgagct ggacggcgac | 180 |
| gtaaacggcc acaagttcag cgtgtccggc gagggcgagg gcgatgccac ctacggcaag | 240 |
| ctgaccctga agttcatctg caccaccggc aagctgcccg tgcctggcc cacccctgtg | 300 |
| accaccctga cctacggcgt gcagtgcttc agccgctacc ccgaccacat gaagcagcac | 360 |
| gacttcttca gtccgccat gcccgaaggc tacgtccagg agcgcaccat cttcttcaag | 420 |
| gacgacggca actacaagac ccgcgccgag gtgaagttcg agggcgacac cctggtgaac | 480 |
| cgcatcgagc tgaagggcat cgacttcaag gaggacggca acatcctggg cacaagctg | 540 |
| gagtacaact acaacagcca caacgtctat atcatggccg acaagcagaa gaacggcatc | 600 |
| aaggtgaact tcaagatccg ccacaacatc gaggacggca gcgtgcagct cgccgaccac | 660 |
| taccagcaga caccccccat cggcgacggc cccgtgctgc tgcccgacaa ccactacctg | 720 |
| agcacccagt ccgccctgag caaagacccc aacgagaagc gcgatcacat ggtcctgctg | 780 |
| gagttcgtga ccgccgccgg gatcactctc ggcatggacg agttactcga gcaccaccac | 840 |
| caccaccac | 849 |

<210> SEQ ID NO 36
<211> LENGTH: 283
<212> TYPE: PRT
<213> ORGANISM: Artificial Sequence
<220> FEATURE:
<223> OTHER INFORMATION: Synthetic peptide

<400> SEQUENCE: 36

Met Ile Lys Ile Ala Thr Arg Lys Tyr Leu Gly Lys Gln Asn Val Tyr
1               5                   10                  15

Gly Ile Gly Val Glu Arg Asp His Asn Phe Ala Leu Lys Asn Gly Phe
            20                  25                  30

Ile Ala Ser Asn Arg Phe Asn Val Ser Lys Gly Glu Glu Leu Phe Thr
        35                  40                  45

Gly Val Val Pro Ile Leu Val Glu Leu Asp Gly Asp Val Asn Gly His
    50                  55                  60

Lys Phe Ser Val Ser Gly Glu Gly Gly Asp Ala Thr Tyr Gly Lys
65                  70                  75                  80

Leu Thr Leu Lys Phe Ile Cys Thr Thr Gly Lys Leu Pro Val Pro Trp
                85                  90                  95

Pro Thr Leu Val Thr Thr Leu Thr Tyr Gly Val Gln Cys Phe Ser Arg
            100                 105                 110

Tyr Pro Asp His Met Lys Gln His Asp Phe Phe Lys Ser Ala Met Pro
        115                 120                 125

Glu Gly Tyr Val Gln Glu Arg Thr Ile Phe Phe Lys Asp Asp Gly Asn
    130                 135                 140

Tyr Lys Thr Arg Ala Glu Val Lys Phe Glu Gly Asp Thr Leu Val Asn
145                 150                 155                 160

Arg Ile Glu Leu Lys Gly Ile Asp Phe Lys Glu Asp Gly Asn Ile Leu
                165                 170                 175

Gly His Lys Leu Glu Tyr Asn Tyr Asn Ser His Asn Val Tyr Ile Met
            180                 185                 190

```
Ala Asp Lys Gln Lys Asn Gly Ile Lys Val Asn Phe Lys Ile Arg His
        195                 200                 205

Asn Ile Glu Asp Gly Ser Val Gln Leu Ala Asp His Tyr Gln Gln Asn
    210                 215                 220

Thr Pro Ile Gly Asp Gly Pro Val Leu Leu Pro Asp Asn His Tyr Leu
225                 230                 235                 240

Ser Thr Gln Ser Ala Leu Ser Lys Asp Pro Asn Glu Lys Arg Asp His
            245                 250                 255

Met Val Leu Leu Glu Phe Val Thr Ala Ala Gly Ile Thr Leu Gly Met
                260                 265                 270

Asp Glu Leu Leu Glu His His His His His His
            275                 280

<210> SEQ ID NO 37
<211> LENGTH: 36
<212> TYPE: PRT
<213> ORGANISM: Artificial Sequence
<220> FEATURE:
<223> OTHER INFORMATION: Synthetic peptide

<400> SEQUENCE: 37

Met Ile Lys Ile Ala Thr Arg Lys Tyr Leu Gly Lys Gln Asn Val Tyr
1               5                   10                  15

Gly Ile Gly Val Glu Arg Asp His Asn Phe Ala Leu Lys Asn Gly Phe
            20                  25                  30

Ile Ala Ser Asn
            35

<210> SEQ ID NO 38
<211> LENGTH: 579
<212> TYPE: PRT
<213> ORGANISM: Artificial Sequence
<220> FEATURE:
<223> OTHER INFORMATION: Synthetic peptide

<400> SEQUENCE: 38

Met Gly His Gly Val Gly Val Pro Gly Val Gly Val Pro Gly Gly Gly
1               5                   10                  15

Val Pro Gly Ala Gly Val Pro Gly Val Gly Val Pro Gly Val Gly Val
            20                  25                  30

Pro Gly Val Gly Val Pro Gly Gly Val Pro Gly Ala Gly Val Pro
            35                  40                  45

Gly Gly Gly Val Pro Gly Val Gly Val Pro Gly Val Gly Val Pro Gly
        50                  55                  60

Gly Gly Val Pro Gly Ala Gly Val Pro Gly Val Gly Val Pro Gly Val
65                  70                  75                  80

Gly Val Pro Gly Val Gly Val Pro Gly Gly Gly Val Pro Gly Ala Gly
                85                  90                  95

Val Pro Gly Gly Gly Val Pro Gly Val Gly Val Pro Gly Val Gly Val
            100                 105                 110

Pro Gly Gly Gly Val Pro Gly Ala Gly Val Pro Gly Val Gly Val Pro
            115                 120                 125

Gly Val Gly Val Pro Gly Gly Gly Val Pro Gly Gly Gly Val Pro Gly
        130                 135                 140

Ala Gly Val Pro Gly Gly Gly Val Pro Gly Val Gly Val Pro Gly Val
145                 150                 155                 160

Gly Val Pro Gly Gly Gly Val Pro Gly Ala Gly Val Pro Gly Val Gly
```

```
                    165                 170                 175
Val Pro Gly Val Gly Val Pro Gly Val Gly Val Pro Gly Gly Val
                180                 185                 190
Pro Gly Ala Gly Val Pro Gly Gly Val Pro Gly Val Gly Val Pro
                195                 200                 205
Gly Val Gly Val Pro Gly Gly Val Pro Gly Ala Gly Val Pro Gly
                210                 215                 220
Val Gly Val Pro Gly Val Gly Val Pro Gly Val Gly Val Pro Gly Gly
225                 230                 235                 240
Gly Val Pro Gly Ala Gly Val Pro Gly Gly Val Pro Gly Val Gly
                245                 250                 255
Val Pro Gly Val Gly Val Pro Gly Gly Val Pro Gly Ala Gly Val
                260                 265                 270
Pro Gly Val Gly Val Pro Gly Val Gly Val Pro Gly Val Gly Val Pro
                275                 280                 285
Gly Gly Gly Val Pro Gly Ala Gly Val Pro Gly Gly Gly Val Pro Gly
                290                 295                 300
Val Gly Val Pro Gly Val Gly Val Pro Gly Gly Gly Val Pro Gly Ala
305                 310                 315                 320
Gly Val Pro Gly Val Gly Val Pro Gly Val Gly Val Pro Gly Val Gly
                325                 330                 335
Val Pro Gly Gly Gly Val Pro Gly Ala Gly Val Pro Gly Gly Gly Val
                340                 345                 350
Pro Gly Val Gly Val Pro Gly Val Gly Val Pro Gly Gly Gly Val Pro
                355                 360                 365
Gly Ala Gly Val Pro Gly Val Gly Val Pro Gly Val Gly Val Pro Gly
                370                 375                 380
Val Gly Val Pro Gly Gly Gly Val Pro Gly Ala Gly Val Pro Gly Gly
385                 390                 395                 400
Gly Val Pro Gly Val Gly Val Pro Gly Val Gly Val Pro Gly Gly Gly
                405                 410                 415
Val Pro Gly Ala Gly Val Pro Gly Val Gly Val Pro Gly Val Gly Val
                420                 425                 430
Pro Gly Val Gly Val Pro Gly Gly Gly Val Pro Gly Ala Gly Val Pro
                435                 440                 445
Gly Gly Gly Val Pro Gly Val Gly Val Pro Gly Val Gly Val Pro Gly
                450                 455                 460
Gly Gly Val Pro Gly Ala Gly Val Pro Gly Val Gly Val Pro Gly Val
465                 470                 475                 480
Gly Val Pro Gly Val Gly Val Pro Gly Gly Gly Val Pro Gly Ala Gly
                485                 490                 495
Val Pro Gly Gly Gly Val Pro Gly Val Gly Val Pro Gly Val Gly Val
                500                 505                 510
Pro Gly Gly Gly Val Pro Gly Ala Gly Val Pro Gly Val Gly Val Pro
                515                 520                 525
Gly Val Gly Val Pro Gly Val Gly Val Pro Gly Gly Gly Val Pro Gly
                530                 535                 540
Ala Gly Val Pro Gly Gly Gly Val Pro Gly Gly Leu Val Ser Ser Asn
545                 550                 555                 560
Asn Asn Asn Asn Asn Asn Asn Leu Gly Ile Glu Gly Arg Ile
                565                 570                 575
Ser Glu Phe
```

<210> SEQ ID NO 39
<211> LENGTH: 102
<212> TYPE: PRT
<213> ORGANISM: Artificial Sequence
<220> FEATURE:
<223> OTHER INFORMATION: Synthetic peptide

<400> SEQUENCE: 39

```
Ala Leu Ser Tyr Glu Thr Glu Ile Leu Thr Val Glu Tyr Gly Leu Leu
1               5                   10                  15

Pro Ile Gly Lys Ile Val Glu Lys Arg Ile Glu Cys Thr Val Tyr Ser
            20                  25                  30

Val Asp Asn Asn Gly Asn Ile Tyr Thr Gln Pro Val Ala Gln Trp His
        35                  40                  45

Asp Arg Gly Glu Gln Glu Val Phe Glu Tyr Cys Leu Glu Asp Gly Ser
    50                  55                  60

Leu Ile Arg Ala Thr Lys Asp His Lys Phe Met Thr Val Asp Gly Gln
65                  70                  75                  80

Met Leu Pro Ile Asp Glu Ile Phe Glu Arg Glu Leu Asp Leu Met Arg
                85                  90                  95

Val Asp Asn Leu Pro Asn
            100
```

<210> SEQ ID NO 40
<211> LENGTH: 108
<212> TYPE: DNA
<213> ORGANISM: Artificial Sequence
<220> FEATURE:
<223> OTHER INFORMATION: Synthetic primer

<400> SEQUENCE: 40

| | |
|---|---|
| atgatcaaaa tagccacacg taaatattta ggcaaacaaa atgtctatgg cattggagtt | 60 |
| gagcgcgacc ataattttgc actcaaaaat ggcttcatag cttctaat | 108 |

<210> SEQ ID NO 41
<211> LENGTH: 2103
<212> TYPE: DNA
<213> ORGANISM: Artificial Sequence
<220> FEATURE:
<223> OTHER INFORMATION: Synthetic primer

<400> SEQUENCE: 41

| | |
|---|---|
| atgggccacg gcgtgggtgt tccgggcgtg ggtgttccgg gtggcggtgt gccgggcgca | 60 |
| ggtgttcctg gtgtaggtgt gccgggtgtt ggtgtgccgg gtgttggtgt accaggtggc | 120 |
| ggtgttccgg gtgcaggcgt tccgggtggc ggtgtgccgg gcgtgggtgt tccgggcgtg | 180 |
| ggtgttccgg gtggcggtgt gccgggcgca ggtgttcctg gtgtaggtgt gccgggtgtt | 240 |
| ggtgtgccgg gtgttggtgt accaggtggc ggtgttccgg gtgcaggcgt tccgggtggc | 300 |
| ggtgtgccgg gcgtgggtgt tccgggcgtg ggtgttccgg gtggcggtgt gccgggcgca | 360 |
| ggtgttcctg gtgtaggtgt gccgggtgtt ggtgtgccgg gtgttggtgt accaggtggc | 420 |
| ggtgttccgg gtgcaggcgt tccgggtggc ggtgtgccgg gcgtgggtgt tccgggcgtg | 480 |
| ggtgttccgg gtggcggtgt gccgggcgca ggtgttcctg gtgtaggtgt gccgggtgtt | 540 |
| ggtgtgccgg gtgttggtgt accaggtggc ggtgttccgg gtgcaggcgt tccgggtggc | 600 |
| ggtgtgccgg gcgtgggtgt tccgggcgtg ggtgttccgg gtggcggtgt gccgggcgca | 660 |
| ggtgttcctg gtgtaggtgt gccgggtgtt ggtgtgccgg gtgttggtgt accaggtggc | 720 |

```
ggtgttccgg gtgcaggcgt tccgggtggc ggtgtgccgg gcgtgggtgt tccgggcgtg    780
ggtgttccgg gtggcggtgt gccgggcgca ggtgttcctg gtgtaggtgt gccgggtgtt    840
ggtgtgccgg gtgttggtgt accaggtggc ggtgttccgg gtgcaggcgt tccgggtggc    900
ggtgtgccgg gcgtgggtgt tccgggcgtg ggtgttccgg gtggcggtgt gccgggcgca    960
ggtgttcctg gtgtaggtgt gccgggtgtt ggtgtgccgg gtgttggtgt accaggtggc   1020
ggtgttccgg gtgcaggcgt tccgggtggc ggtgtgccgg gcgtgggtgt tccgggcgtg   1080
ggtgttccgg gtggcggtgt gccgggcgca ggtgttcctg gtgtaggtgt gccgggtgtt   1140
ggtgtgccgg gtgttggtgt accaggtggc ggtgttccgg gtgcaggcgt tccgggtggc   1200
ggtgtgccgg gcgtgggtgt tccgggcgtg ggtgttccgg gtggcggtgt gccgggcgca   1260
ggtgttcctg gtgtaggtgt gccgggtgtt ggtgtgccgg gtgttggtgt accaggtggc   1320
ggtgttccgg gtgcaggcgt tccgggtggc ggtgtgccgg gcgtgggtgt tccgggcgtg   1380
ggtgttccgg gtggcggtgt gccgggcgca ggtgttcctg gtgtaggtgt gccgggtgtt   1440
ggtgtgccgg gtgttggtgt accaggtggc ggtgttccgg gtgcaggcgt tccgggtggc   1500
ggtgtgccgg gcgtgggtgt tccgggcgtg ggtgttccgg gtggcggtgt gccgggcgca   1560
ggtgttcctg gtgtaggtgt gccgggtgtt ggtgtgccgg gtgttggtgt accaggtggc   1620
ggtgttccgg gtgcaggcgt tccgggtggc ggtgtgccgg gcgggctggt gagctcgaac   1680
aacaacaaca ataacaataa caacaacctc gggatcgagg aaggatttc agaattcgga    1740
ggcggaggga gcggaggcgg agggagcgct agctgtttaa gctatgaaac ggaaatattg   1800
acagtagaat atggattatt accgattggt aaaattgtag aaaagcgcat cgaatgtact   1860
gtttatagcg ttgataataa tggaaatatt tatacacaac ctgtagcaca atggcacgat   1920
cgcggagaac aagaggtgtt tgagtattgt ttggaagatg gttcattgat tcgggcaaca   1980
aaagaccata agtttatgac tgttgatggt caaatgttgc caattgatga aatatttgaa   2040
cgtgaattgg atttgatgcg ggttgataat ttgccgaatc tcgagcacca ccaccaccac   2100
cac                                                                 2103
```

<210> SEQ ID NO 42
<211> LENGTH: 701
<212> TYPE: PRT
<213> ORGANISM: Artificial Sequence
<220> FEATURE:
<223> OTHER INFORMATION: Synthetic peptide

<400> SEQUENCE: 42

```
Met Gly His Gly Val Gly Val Pro Gly Val Gly Val Pro Gly Gly Gly
1               5                  10                  15
Val Pro Gly Ala Gly Val Pro Gly Val Gly Val Pro Gly Val Gly Val
            20                  25                  30
Pro Gly Val Gly Val Pro Gly Gly Gly Val Pro Gly Ala Gly Val Pro
        35                  40                  45
Gly Gly Gly Val Pro Gly Val Gly Val Pro Gly Gly Gly Val Pro Gly
    50                  55                  60
Gly Gly Val Pro Gly Ala Gly Val Pro Gly Val Gly Val Pro Gly Val
65                  70                  75                  80
Gly Val Pro Gly Val Gly Val Pro Gly Gly Gly Val Pro Gly Ala Gly
                85                  90                  95
Val Pro Gly Gly Gly Val Pro Gly Val Gly Val Pro Gly Val Gly Val
            100                 105                 110
```

Pro Gly Gly Gly Val Pro Gly Ala Gly Val Pro Gly Val Pro
            115                 120                 125

Gly Val Gly Val Pro Gly Val Gly Val Pro Gly Gly Gly Val Pro Gly
            130                 135                 140

Ala Gly Val Pro Gly Gly Gly Val Pro Gly Val Gly Val Pro Gly Val
145                 150                 155                 160

Gly Val Pro Gly Gly Gly Val Pro Gly Ala Gly Val Pro Gly Val Gly
                165                 170                 175

Val Pro Gly Val Gly Val Pro Gly Val Gly Val Pro Gly Gly Gly Val
            180                 185                 190

Pro Gly Ala Gly Val Pro Gly Gly Gly Val Pro Gly Val Gly Val Pro
            195                 200                 205

Gly Val Gly Val Pro Gly Gly Gly Val Pro Gly Ala Gly Val Pro Gly
            210                 215                 220

Val Gly Val Pro Gly Val Gly Val Pro Gly Val Gly Val Pro Gly Gly
225                 230                 235                 240

Gly Val Pro Gly Ala Gly Val Pro Gly Gly Gly Val Pro Gly Val Gly
                245                 250                 255

Val Pro Gly Val Gly Val Pro Gly Gly Gly Val Pro Gly Ala Gly Val
            260                 265                 270

Pro Gly Val Gly Val Pro Gly Val Gly Val Pro Gly Val Gly Val Pro
            275                 280                 285

Gly Gly Gly Val Pro Gly Ala Gly Val Pro Gly Gly Gly Val Pro Gly
            290                 295                 300

Val Gly Val Pro Gly Val Gly Val Pro Gly Gly Gly Val Pro Gly Ala
305                 310                 315                 320

Gly Val Pro Gly Val Gly Val Pro Gly Val Gly Val Pro Gly Val Gly
                325                 330                 335

Val Pro Gly Gly Gly Val Pro Gly Ala Gly Val Pro Gly Gly Gly Val
            340                 345                 350

Pro Gly Val Gly Val Pro Gly Val Gly Val Pro Gly Gly Gly Val Pro
            355                 360                 365

Gly Ala Gly Val Pro Gly Val Gly Val Pro Gly Val Gly Val Pro Gly
            370                 375                 380

Val Gly Val Pro Gly Gly Gly Val Pro Gly Ala Gly Val Pro Gly Gly
385                 390                 395                 400

Gly Val Pro Gly Val Gly Val Pro Gly Val Gly Val Pro Gly Gly Gly
                405                 410                 415

Val Pro Gly Ala Gly Val Pro Gly Val Gly Val Pro Gly Val Gly Val
            420                 425                 430

Pro Gly Val Gly Val Pro Gly Gly Gly Val Pro Gly Ala Gly Val Pro
            435                 440                 445

Gly Gly Gly Val Pro Gly Val Gly Val Pro Gly Val Gly Val Pro Gly
            450                 455                 460

Gly Gly Val Pro Gly Ala Gly Val Pro Gly Val Gly Val Pro Gly Val
465                 470                 475                 480

Gly Val Pro Gly Val Gly Val Pro Gly Gly Gly Val Pro Gly Ala Gly
                485                 490                 495

Val Pro Gly Gly Gly Val Pro Gly Val Gly Val Pro Gly Val Gly Val
            500                 505                 510

Pro Gly Gly Gly Val Pro Gly Ala Gly Val Pro Gly Val Gly Val Pro
            515                 520                 525

Gly Val Gly Val Pro Gly Val Gly Val Pro Gly Gly Gly Val Pro Gly

Ala Gly Val Pro Gly Gly Val Pro Gly Gly Leu Val Ser Ser Asn
545                 550                 555                 560

Asn Asn Asn Asn Asn Asn Asn Asn Leu Gly Ile Glu Gly Arg Ile
            565                 570                 575

Ser Glu Phe Gly Gly Gly Ser Gly Gly Gly Ser Ala Ser Cys
            580                 585                 590

Leu Ser Tyr Glu Thr Glu Ile Leu Thr Val Glu Tyr Gly Leu Leu Pro
            595                 600                 605

Ile Gly Lys Ile Val Glu Lys Arg Ile Glu Cys Thr Val Tyr Ser Val
            610                 615                 620

Asp Asn Asn Gly Asn Ile Tyr Thr Gln Pro Val Ala Gln Trp His Asp
625                 630                 635                 640

Arg Gly Glu Gln Glu Val Phe Glu Tyr Cys Leu Glu Asp Gly Ser Leu
                645                 650                 655

Ile Arg Ala Thr Lys Asp His Lys Phe Met Thr Val Asp Gly Gln Met
                660                 665                 670

Leu Pro Ile Asp Glu Ile Phe Glu Arg Glu Leu Asp Leu Met Arg Val
                675                 680                 685

Asp Asn Leu Pro Asn Leu Glu His His His His His
690                 695                 700

<210> SEQ ID NO 43
<211> LENGTH: 43
<212> TYPE: DNA
<213> ORGANISM: Artificial Sequence
<220> FEATURE:
<223> OTHER INFORMATION: Synthetic primer

<400> SEQUENCE: 43
ttagaaggca tatgatcaaa atagccacac gtaaatattt agg            43

<210> SEQ ID NO 44
<211> LENGTH: 45
<212> TYPE: DNA
<213> ORGANISM: Artificial Sequence
<220> FEATURE:
<223> OTHER INFORMATION: Synthetic primer

<400> SEQUENCE: 44
cctcgccctt gctcacattg aaacaattag aagctatgaa gccat          45

<210> SEQ ID NO 45
<211> LENGTH: 37
<212> TYPE: DNA
<213> ORGANISM: Artificial Sequence
<220> FEATURE:
<223> OTHER INFORMATION: Synthetic primer

<400> SEQUENCE: 45
atagcttcta attgtttcaa tgtgagcaag ggcgagg                   37

<210> SEQ ID NO 46
<211> LENGTH: 32
<212> TYPE: DNA
<213> ORGANISM: Artificial Sequence
<220> FEATURE:
<223> OTHER INFORMATION: Synthetic primer

<400> SEQUENCE: 46
taaaatctcg agtaactcgt ccatgccgag ag                        32

<210> SEQ ID NO 47
<211> LENGTH: 30
<212> TYPE: DNA
<213> ORGANISM: Artificial Sequence
<220> FEATURE:
<223> OTHER INFORMATION: Synthetic primer

<400> SEQUENCE: 47
ggcaaacaaa atgtctatgg cattggagtt                                    30

<210> SEQ ID NO 48
<211> LENGTH: 30
<212> TYPE: DNA
<213> ORGANISM: Artificial Sequence
<220> FEATURE:
<223> OTHER INFORMATION: Synthetic primer

<400> SEQUENCE: 48
gtcgcgctca actccaatgc catagacatt                                    30

<210> SEQ ID NO 49
<211> LENGTH: 78
<212> TYPE: DNA
<213> ORGANISM: Artificial Sequence
<220> FEATURE:
<223> OTHER INFORMATION: Synthetic primer

<400> SEQUENCE: 49
cctggaagct tgtggaggcg gagggagcgg aggcggaggg agcgctagct gtttaagcta    60
tgaaacggaa atattgac                                                 78

<210> SEQ ID NO 50
<211> LENGTH: 33
<212> TYPE: DNA
<213> ORGANISM: Artificial Sequence
<220> FEATURE:
<223> OTHER INFORMATION: Synthetic primer

<400> SEQUENCE: 50
atatagctcg agattcggca aattatcaac ccg                                33

<210> SEQ ID NO 51
<211> LENGTH: 44
<212> TYPE: DNA
<213> ORGANISM: Artificial Sequence
<220> FEATURE:
<223> OTHER INFORMATION: Synthetic primer

<400> SEQUENCE: 51
taatttaaca tatgaaaatc gaagaaggta aactgacaaa tcct                    44

<210> SEQ ID NO 52
<211> LENGTH: 33
<212> TYPE: DNA
<213> ORGANISM: Artificial Sequence
<220> FEATURE:
<223> OTHER INFORMATION: Synthetic primer

<400> SEQUENCE: 52
aagattaaag cttcttgaag ctgccacaag gca                                33

<210> SEQ ID NO 53
<211> LENGTH: 42
<212> TYPE: DNA

```
<213> ORGANISM: Artificial Sequence
<220> FEATURE:
<223> OTHER INFORMATION: Synthetic primer

<400> SEQUENCE: 53
aattaagcta gcgccttaag ctatgaaacg gaaatattga ca                           42

<210> SEQ ID NO 54
<211> LENGTH: 30
<212> TYPE: DNA
<213> ORGANISM: Artificial Sequence
<220> FEATURE:
<223> OTHER INFORMATION: Synthetic primer

<400> SEQUENCE: 54
aatatgggaa ttcggaggcg gagggagcgg                                        30

<210> SEQ ID NO 55
<211> LENGTH: 30
<212> TYPE: DNA
<213> ORGANISM: Artificial Sequence
<220> FEATURE:
<223> OTHER INFORMATION: Synthetic primer

<400> SEQUENCE: 55
gtacattaag cttagcagcc ggatctcagt                                        30

<210> SEQ ID NO 56
<211> LENGTH: 39
<212> TYPE: DNA
<213> ORGANISM: Artificial Sequence
<220> FEATURE:
<223> OTHER INFORMATION: Synthetic primer

<400> SEQUENCE: 56
attcgcgcta gcattgaaac aattagaagc tatgaagcc                              39

<210> SEQ ID NO 57
<211> LENGTH: 29
<212> TYPE: DNA
<213> ORGANISM: Artificial Sequence
<220> FEATURE:
<223> OTHER INFORMATION: Synthetic primer

<400> SEQUENCE: 57
taaaatctcg agcaggaaca ggtggtggc                                         29

<210> SEQ ID NO 58
<211> LENGTH: 64
<212> TYPE: DNA
<213> ORGANISM: Artificial Sequence
<220> FEATURE:
<223> OTHER INFORMATION: Synthetic primer

<400> SEQUENCE: 58
ttcaataagc ttggaggcgg agggagcgga ggcggaggga gcgctagcgc ctcctccgag       60
gacg                                                                    64

<210> SEQ ID NO 59
<211> LENGTH: 38
<212> TYPE: DNA
<213> ORGANISM: Artificial Sequence
<220> FEATURE:
<223> OTHER INFORMATION: Synthetic primer

<400> SEQUENCE: 59
```
atttaacgct agcatgctgc cgaaactcgt tataactc                            38

<210> SEQ ID NO 60
<211> LENGTH: 30
<212> TYPE: DNA
<213> ORGANISM: Artificial Sequence
<220> FEATURE:
<223> OTHER INFORMATION: Synthetic primer

<400> SEQUENCE: 60
agtttagctc gaggtctgcg gcaggattgg                                     30

<210> SEQ ID NO 61
<211> LENGTH: 37
<212> TYPE: DNA
<213> ORGANISM: Artificial Sequence
<220> FEATURE:
<223> OTHER INFORMATION: Synthetic primer

<400> SEQUENCE: 61
atttcaatgc tagcatgacc atgattacgg attcact                             37

<210> SEQ ID NO 62
<211> LENGTH: 34
<212> TYPE: DNA
<213> ORGANISM: Artificial Sequence
<220> FEATURE:
<223> OTHER INFORMATION: Synthetic primer

<400> SEQUENCE: 62
tgataatctc gagttttga caccagacca actg                                 34

<210> SEQ ID NO 63
<211> LENGTH: 54
<212> TYPE: DNA
<213> ORGANISM: Artificial Sequence
<220> FEATURE:
<223> OTHER INFORMATION: Synthetic primer

<400> SEQUENCE: 63
gtttcaatgc tagcatggag aaaaaaatca ctggatatac caccgttgat atat          54

<210> SEQ ID NO 64
<211> LENGTH: 32
<212> TYPE: DNA
<213> ORGANISM: Artificial Sequence
<220> FEATURE:
<223> OTHER INFORMATION: Synthetic primer

<400> SEQUENCE: 64
taataattaa ctcgagcgcc ccgccctgcc ac                                  32

<210> SEQ ID NO 65
<211> LENGTH: 45
<212> TYPE: DNA
<213> ORGANISM: Artificial Sequence
<220> FEATURE:
<223> OTHER INFORMATION: Synthetic primer

<400> SEQUENCE: 65
gtttcaatgc tagcatgaaa atcgaagaag gtaaactggt aatct                    45

<210> SEQ ID NO 66
<211> LENGTH: 31
<212> TYPE: DNA

```
<213> ORGANISM: Artificial Sequence
<220> FEATURE:
<223> OTHER INFORMATION: Synthetic primer

<400> SEQUENCE: 66
aagttatact cgagtcccct tccctcgatc c                                31

<210> SEQ ID NO 67
<211> LENGTH: 138
<212> TYPE: PRT
<213> ORGANISM: Artificial Sequence
<220> FEATURE:
<223> OTHER INFORMATION: Synthetic peptide

<400> SEQUENCE: 67
```

Cys Leu Ser Tyr Glu Thr Glu Ile Leu Thr Val Glu Tyr Gly Leu Leu
1               5                   10                  15

Pro Ile Gly Lys Ile Val Glu Lys Arg Ile Glu Cys Thr Val Tyr Ser
            20                  25                  30

Val Asp Asn Asn Gly Asn Ile Tyr Thr Gln Pro Val Ala Gln Trp His
        35                  40                  45

Asp Arg Gly Glu Gln Glu Val Phe Glu Tyr Cys Leu Glu Asp Gly Ser
    50                  55                  60

Leu Ile Arg Ala Thr Lys Asp His Lys Phe Met Thr Val Asp Gly Gln
65                  70                  75                  80

Met Leu Pro Ile Asp Glu Ile Phe Glu Arg Glu Leu Asp Leu Met Arg
                85                  90                  95

Val Asp Asn Leu Pro Asn Met Ile Lys Ile Ala Thr Arg Lys Tyr Leu
            100                 105                 110

Gly Lys Gln Asn Val Tyr Asp Ile Gly Val Glu Arg Asp His Asn Phe
        115                 120                 125

Ala Leu Lys Asn Gly Phe Ile Ala Ser Asn
    130                 135

```
<210> SEQ ID NO 68
<211> LENGTH: 159
<212> TYPE: PRT
<213> ORGANISM: Artificial Sequence
<220> FEATURE:
<223> OTHER INFORMATION: Synthetic peptide

<400> SEQUENCE: 68
```

Cys Leu Ser Phe Gly Thr Glu Ile Leu Thr Val Glu Tyr Gly Pro Leu
1               5                   10                  15

Pro Ile Gly Lys Ile Val Ser Glu Glu Ile Asn Cys Ser Val Tyr Ser
            20                  25                  30

Val Asp Pro Glu Gly Arg Val Tyr Thr Gln Ala Ile Ala Gln Trp His
        35                  40                  45

Asp Arg Gly Glu Gln Glu Val Leu Glu Tyr Glu Leu Glu Asp Gly Ser
    50                  55                  60

Val Ile Arg Ala Thr Ser Asp His Arg Phe Leu Thr Thr Asp Tyr Gln
65                  70                  75                  80

Leu Leu Ala Ile Glu Glu Ile Phe Ala Arg Gln Leu Asp Leu Leu Thr
                85                  90                  95

Leu Glu Asn Ile Lys Gln Thr Glu Glu Ala Leu Asp Asn His Arg Leu
            100                 105                 110

Pro Phe Pro Leu Leu Asp Ala Gly Thr Ile Lys Met Val Lys Val Ile
        115                 120                 125

Gly Arg Arg Ser Leu Gly Val Gln Arg Ile Phe Asp Ile Gly Leu Pro
            130                 135                 140

Gln Asp His Asn Phe Leu Leu Ala Asn Gly Ala Ile Ala Ala Asn
145                 150                 155

<210> SEQ ID NO 69
<211> LENGTH: 168
<212> TYPE: PRT
<213> ORGANISM: Artificial Sequence
<220> FEATURE:
<223> OTHER INFORMATION: Synthetic peptide

<400> SEQUENCE: 69

Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Ala Ala Lys Asp Gly Thr Leu His Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Ile Val Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gln Pro
                85                  90                  95

Arg Arg Phe Asp Gly Phe Gly Asp Ser Ala Pro Ile Pro Ala Arg Val
            100                 105                 110

Gln Ala Leu Ala Asp Ala Leu Asp Lys Phe Leu His Asp Met Leu
        115                 120                 125

Ala Glu Glu Leu Arg Tyr Ser Val Ile Arg Glu Val Leu Pro Thr Arg
    130                 135                 140

Arg Ala Arg Thr Phe Asp Leu Glu Val Glu Leu His Thr Leu Val
145                 150                 155                 160

Ala Glu Gly Val Val Val His Asn
                165

<210> SEQ ID NO 70
<211> LENGTH: 137
<212> TYPE: PRT
<213> ORGANISM: Artificial Sequence
<220> FEATURE:
<223> OTHER INFORMATION: Synthetic peptide

<400> SEQUENCE: 70

Cys Leu Ser Tyr Glu Thr Glu Ile Leu Thr Val Glu Tyr Gly Leu Leu
1               5                   10                  15

Pro Ile Gly Lys Ile Val Glu Lys Arg Ile Glu Cys Thr Val Tyr Ser
            20                  25                  30

Val Asp Asn Asn Gly Asn Ile Tyr Thr Gln Pro Val Ala Gln Trp His
        35                  40                  45

Asp Arg Gly Glu Gln Glu Val Phe Glu Cys Leu Glu Asp Gly Ser Leu
    50                  55                  60

Ile Arg Ala Thr Lys Asp His Lys Phe Met Thr Val Ser Gly Gln Met
65                  70                  75                  80

Leu Pro Ile Asp Glu Ile Phe Glu Arg Glu Leu Asp Leu Met Arg Val
                85                  90                  95

Asp Asn Leu Pro Asn Met Ile Lys Ile Ala Thr Arg Lys Tyr Leu Gly
            100                 105                 110

Lys Gln Asn Val Tyr Asp Ile Gly Val Glu Arg Asp His Asn Phe Ala
            115                 120                 125

Leu Lys Asn Gly Phe Ile Ala Ser Asn
        130                 135

<210> SEQ ID NO 71
<211> LENGTH: 159
<212> TYPE: PRT
<213> ORGANISM: Artificial Sequence
<220> FEATURE:
<223> OTHER INFORMATION: Synthetic peptide

<400> SEQUENCE: 71

Cys Leu Ser Phe Gly Thr Glu Ile Leu Thr Val Glu Tyr Gly Pro Leu
1               5                   10                  15

Pro Ile Gly Lys Ile Val Ser Glu Glu Ile Asn Cys Ser Val Tyr Ser
            20                  25                  30

Val Asp Pro Glu Gly Arg Val Tyr Thr Gln Ala Ile Ala Gln Trp His
        35                  40                  45

Asp Arg Gly Glu Gln Glu Val Leu Glu Tyr Glu Leu Glu Asp Gly Ser
    50                  55                  60

Val Ile Arg Ala Thr Ser Asp His Arg Phe Leu Thr Thr Asp Tyr Gln
65                  70                  75                  80

Leu Leu Ala Ile Glu Glu Ile Phe Ala Arg Gln Leu Asp Leu Leu Thr
                85                  90                  95

Leu Glu Asn Ile Lys Gln Thr Glu Glu Ala Leu Asp Asn His Arg Leu
            100                 105                 110

Pro Phe Pro Leu Leu Asp Ala Gly Thr Ile Lys Met Val Lys Val Ile
        115                 120                 125

Gly Arg Arg Ser Leu Gly Val Gln Arg Ile Phe Asp Ile Gly Leu Pro
    130                 135                 140

Gln Asp His Asn Phe Leu Leu Ala Asn Gly Ala Ile Ala Ala Asn
145                 150                 155

<210> SEQ ID NO 72
<211> LENGTH: 146
<212> TYPE: PRT
<213> ORGANISM: Artificial Sequence
<220> FEATURE:
<223> OTHER INFORMATION: Synthetic peptide

<400> SEQUENCE: 72

Cys Leu Ser Tyr Asp Thr Glu Ile Trp Thr Val Glu Tyr Gly Ala Met
1               5                   10                  15

Pro Ile Gly Lys Ile Val Glu Glu Lys Ile Glu Cys Ser Val Tyr Thr
            20                  25                  30

Val Asp Glu Asn Gly Phe Val Tyr Thr Gln Pro Ile Ala Gln Trp His
        35                  40                  45

Pro Arg Gly Gln Gln Glu Ile Ile Glu Tyr Thr Leu Glu Asp Gly Arg
    50                  55                  60

Lys Ile Arg Ala Thr Lys Asp His Lys Met Met Thr Glu Ser Gly Glu
65                  70                  75                  80

Met Leu Pro Ile Glu Glu Ile Phe Gln Arg Glu Leu Asp Leu Lys Val
                85                  90                  95

Glu Thr Phe His Glu Met Ser Leu Leu Arg Arg Gly Ala Lys Met Val
            100                 105                 110

Lys Ile Ile Lys Arg Gln Ser Leu Gly Arg Gln Asn Val Tyr Asp Val

```
              115                 120                 125
Cys Val Glu Thr Asp His Asn Phe Val Leu Ala Asn Gly Cys Val Ala
    130                 135                 140

Ser Asn
145

<210> SEQ ID NO 73
<211> LENGTH: 137
<212> TYPE: PRT
<213> ORGANISM: Artificial Sequence
<220> FEATURE:
<223> OTHER INFORMATION: Synthetic peptide

<400> SEQUENCE: 73

Cys Leu Ser Ala Asp Thr Glu Ile Leu Thr Val Glu Tyr Gly Phe Leu
1               5                   10                  15

Pro Ile Gly Glu Ile Val Gly Lys Ala Ile Glu Cys Arg Val Tyr Ser
                20                  25                  30

Val Asp Gly Asn Gly Asn Ile Tyr Thr Gln Ser Ile Ala Gln Trp His
            35                  40                  45

Asn Arg Gly Glu Gln Glu Val Phe Glu Tyr Thr Leu Glu Asp Gly Ser
        50                  55                  60

Ile Ile Arg Ala Thr Lys Asp His Lys Phe Met Thr Thr Asp Gly Glu
65                  70                  75                  80

Met Leu Pro Ile Asp Glu Ile Phe Ala Arg Gln Leu Asp Leu Met Gln
                85                  90                  95

Val Gln Gly Leu His Met Val Lys Ile Thr Ala Arg Lys Phe Val Gly
            100                 105                 110

Arg Glu Asn Val Tyr Asp Ile Gly Val Glu His His His Asn Phe Ala
        115                 120                 125

Ile Lys Asn Gly Leu Ile Ala Ser Asn
    130                 135

<210> SEQ ID NO 74
<211> LENGTH: 138
<212> TYPE: PRT
<213> ORGANISM: Artificial Sequence
<220> FEATURE:
<223> OTHER INFORMATION: Synthetic peptide

<400> SEQUENCE: 74

Cys Leu Ser Tyr Asp Thr Glu Val Leu Thr Val Glu Tyr Gly Phe Val
1               5                   10                  15

Pro Ile Gly Glu Ile Val Glu Lys Gly Ile Glu Cys Ser Val Gly Ser
                20                  25                  30

Ile Asn Asn Asn Gly Ile Val Tyr Thr Gln Pro Ile Ala Gln Trp His
            35                  40                  45

His Arg Gly Lys Gln Glu Val Phe Glu Tyr Cys Leu Glu Asp Gly Ser
        50                  55                  60

Ile Ile Lys Ala Thr Lys Asp His Lys Phe Met Thr Gln Asp Gly Lys
65                  70                  75                  80

Met Leu Pro Ile Asp Glu Ile Phe Glu Gln Glu Leu Asp Leu Leu Gln
                85                  90                  95

Val Lys Gly Leu Pro Glu Met Ile Lys Ile Ala Ser Arg Lys Phe Leu
            100                 105                 110

Gly Val Glu Asn Val Tyr Asp Ile Gly Val Arg Arg Asp His Asn Phe
        115                 120                 125
```

```
Phe Ile Lys Asn Gly Leu Ile Ala Ser Asn
    130                 135
```

<210> SEQ ID NO 75
<211> LENGTH: 138
<212> TYPE: PRT
<213> ORGANISM: Artificial Sequence
<220> FEATURE:
<223> OTHER INFORMATION: Synthetic peptide

<400> SEQUENCE: 75

```
Cys Leu Ser Tyr Asp Thr Glu Val Leu Thr Val Glu Tyr Gly Phe Val
1               5                   10                  15

Pro Ile Gly Glu Ile Val Asp Lys Gly Ile Glu Cys Ser Val Phe Ser
            20                  25                  30

Ile Asp Ser Asn Gly Ile Val Tyr Thr Gln Pro Ile Ala Gln Trp His
        35                  40                  45

His Arg Gly Lys Gln Glu Val Phe Glu Tyr Cys Leu Glu Asp Gly Ser
    50                  55                  60

Ile Ile Lys Ala Thr Lys Asp His Lys Phe Met Thr Gln Asp Gly Lys
65                  70                  75                  80

Met Leu Pro Ile Asp Glu Ile Phe Glu Gln Gly Leu Asp Leu Leu Gln
                85                  90                  95

Val Lys Gly Leu Pro Glu Met Ile Lys Ile Ala Ser Arg Lys Phe Leu
            100                 105                 110

Gly Val Glu Asn Val Tyr Asp Ile Gly Val Gly Arg Asp His Asn Phe
        115                 120                 125

Phe Val Lys Asn Gly Leu Ile Ala Ser Asn
    130                 135
```

<210> SEQ ID NO 76
<211> LENGTH: 154
<212> TYPE: PRT
<213> ORGANISM: Artificial Sequence
<220> FEATURE:
<223> OTHER INFORMATION: Synthetic peptide

<400> SEQUENCE: 76

```
Cys Leu Ser Tyr Glu Thr Glu Val Leu Thr Leu Glu Tyr Gly Phe Val
1               5                   10                  15

Pro Ile Gly Glu Ile Val Asn Lys Gln Met Val Cys Thr Val Phe Ser
            20                  25                  30

Leu Asn Asp Ser Gly Asn Val Tyr Thr Gln Pro Ile Gly Gln Trp His
        35                  40                  45

Asp Arg Gly Val Gln Asp Leu Tyr Glu Tyr Cys Leu Asp Asp Gly Ser
    50                  55                  60

Thr Ile Arg Ala Thr Lys Asp His Lys Phe Met Thr Thr Gln Gly Glu
65                  70                  75                  80

Met Val Pro Ile Asp Glu Ile Phe His Gln Gly Trp Glu Leu Val Gln
                85                  90                  95

Val Ser Gly Ile Ser Lys Leu Val Gln Gln Arg Thr Leu Pro Phe Ile
            100                 105                 110

Ile Val Asp Arg Lys Leu Met Val Lys Ile Val Ser Arg Arg Tyr Leu
        115                 120                 125

Gly Lys Ala Asp Val Tyr Asp Ile Gly Val Ala Lys Asp His Asn Phe
    130                 135                 140

Ile Ile Lys Asn Gly Leu Val Ala Ser Asn
145                 150
```

<210> SEQ ID NO 77
<211> LENGTH: 135
<212> TYPE: PRT
<213> ORGANISM: Artificial Sequence
<220> FEATURE:
<223> OTHER INFORMATION: Synthetic peptide

<400> SEQUENCE: 77

Cys Leu Ser Tyr Asp Thr Glu Ile Leu Thr Val Glu Tyr Gly Pro Met
1               5                   10                  15

Pro Ile Gly Lys Ile Val Glu Glu Asn Ile Asn Cys Ser Val Tyr Thr
            20                  25                  30

Val Asn Lys Asn Gly Phe Val Tyr Thr Gln Ser Ile Ala Gln Trp His
        35                  40                  45

His Arg Gly Glu Gln Glu Val Phe Glu Tyr Tyr Leu Glu Asp Gly Glu
    50                  55                  60

Thr Ile Arg Ala Thr Lys Asp His Lys Phe Met Thr Thr Glu Gly Lys
65                  70                  75                  80

Met Leu Pro Ile Asp Glu Ile Phe Glu Asn Asn Leu Asp Leu Lys Lys
                85                  90                  95

Leu Thr Val Met Val Lys Ile Ile Glu Arg Arg Ser Leu Gly Lys Gln
            100                 105                 110

Asn Val Tyr Asp Ile Gly Val Glu Lys Asp His Asn Phe Leu Leu Ser
        115                 120                 125

Asn Asn Leu Ile Ala Ser Asn
    130                 135

<210> SEQ ID NO 78
<211> LENGTH: 135
<212> TYPE: PRT
<213> ORGANISM: Artificial Sequence
<220> FEATURE:
<223> OTHER INFORMATION: Synthetic peptide

<400> SEQUENCE: 78

Cys Leu Ser Tyr Asp Thr Glu Ile Leu Thr Val Glu Tyr Gly Ala Ile
1               5                   10                  15

Pro Ile Gly Lys Val Val Glu Glu Asn Ile Asp Cys Thr Val Tyr Thr
            20                  25                  30

Val Asp Lys Asn Gly Phe Val Tyr Thr Gln Asn Ile Ala Gln Trp His
        35                  40                  45

Leu Arg Gly Gln Gln Glu Val Phe Glu Tyr Tyr Leu Asp Asp Gly Ser
    50                  55                  60

Ile Leu Arg Ala Thr Lys Asp His Gln Phe Met Thr Leu Glu Gly Glu
65                  70                  75                  80

Met Leu Pro Ile His Glu Ile Phe Glu Arg Gly Leu Glu Leu Lys Lys
                85                  90                  95

Ile Lys Ile Met Val Lys Ile Val Ser Tyr Arg Ser Leu Gly Lys Gln
            100                 105                 110

Phe Val Tyr Asp Ile Gly Val Ala Gln Asp His Asn Phe Leu Leu Ala
        115                 120                 125

Asn Gly Ser Ile Ala Ser Asn
    130                 135

<210> SEQ ID NO 79
<211> LENGTH: 142
<212> TYPE: PRT

<213> ORGANISM: Artificial Sequence
<220> FEATURE:
<223> OTHER INFORMATION: Synthetic peptide

<400> SEQUENCE: 79

Cys Leu Ser Tyr Asp Thr Glu Ile Leu Thr Val Glu Tyr Gly Ala Met
1               5                   10                  15

Tyr Ile Gly Lys Ile Val Glu Glu Asn Ile Asn Cys Thr Val Tyr Thr
            20                  25                  30

Val Asp Lys Asn Gly Phe Val Tyr Thr Gln Thr Ile Ala Gln Trp His
        35                  40                  45

Asn Arg Gly Glu Gln Glu Ile Phe Glu Tyr Asp Leu Glu Asp Gly Ser
    50                  55                  60

Lys Ile Lys Ala Thr Lys Asp His Lys Phe Met Thr Ile Asp Gly Glu
65                  70                  75                  80

Met Leu Pro Ile Asp Glu Ile Phe Glu Lys Asn Leu Asp Leu Lys Gln
                85                  90                  95

Val Val Ser His Pro Asp Asp Tyr Leu Val Met Val Lys Ile Ile Gly
            100                 105                 110

Cys Arg Ser Leu Gly Thr Gln Lys Val Tyr Asp Ile Gly Val Glu Lys
        115                 120                 125

Asp His Asn Phe Leu Leu Ala Asn Gly Ser Ile Ala Ser Asn
    130                 135                 140

<210> SEQ ID NO 80
<211> LENGTH: 136
<212> TYPE: PRT
<213> ORGANISM: Artificial Sequence
<220> FEATURE:
<223> OTHER INFORMATION: Synthetic peptide

<400> SEQUENCE: 80

Cys Leu Gly Gly Glu Thr Leu Ile Leu Thr Glu Glu Tyr Gly Leu Leu
1               5                   10                  15

Pro Ile Ala Lys Ile Val Ser Glu Glu Ile Asn Cys Thr Val Tyr Thr
            20                  25                  30

Val Asp Gln Asn Gly Phe Val Tyr Ser Gln Pro Ile Ser Gln Trp His
        35                  40                  45

Glu Arg Gly Leu Gln Glu Val Phe Glu Tyr Thr Leu Glu Asn Gly Gln
    50                  55                  60

Thr Ile Gln Ala Thr Lys Asp His Lys Phe Met Thr Ser Asp Gly Glu
65                  70                  75                  80

Met Leu Ala Ile Asp Thr Ile Phe Glu Arg Gly Leu Asp Leu Lys Ser
                85                  90                  95

Ser Asp Phe Ser Met Val Lys Ile Ile Gly Arg Gln Ser Leu Gly Arg
            100                 105                 110

Lys Pro Val Tyr Asp Ile Gly Val Glu Lys Asp His Asn Phe Leu Leu
        115                 120                 125

Gly Asn Gly Leu Ile Ala Ser Asn
    130                 135

<210> SEQ ID NO 81
<211> LENGTH: 140
<212> TYPE: PRT
<213> ORGANISM: Artificial Sequence
<220> FEATURE:
<223> OTHER INFORMATION: Synthetic peptide

```
<400> SEQUENCE: 81

Cys Leu Ser Tyr Asp Thr Gln Ile Leu Thr Val Glu Tyr Gly Ala Val
1               5                   10                  15

Ala Ile Gly Glu Ile Val Glu Lys Gln Ile Glu Cys Thr Val Tyr Ser
            20                  25                  30

Val Asp Glu Asn Gly Tyr Val Tyr Thr Gln Pro Ile Ala Gln Trp His
        35                  40                  45

Asn Arg Gly Glu Gln Glu Val Phe Glu Tyr Leu Leu Glu Asp Gly Ala
    50                  55                  60

Thr Ile Arg Ala Thr Lys Asp His Lys Phe Met Thr Asp Glu Asp Gln
65                  70                  75                  80

Met Leu Pro Ile Asp Gln Ile Phe Glu Gln Gly Leu Glu Leu Lys Gln
                85                  90                  95

Val Glu Val Leu Gln Pro Val Phe Met Val Lys Ile Val Arg Arg Gln
            100                 105                 110

Ser Leu Gly Val Gln Asn Val Tyr Asp Ile Gly Val Glu Lys Asp His
            115                 120                 125

Asn Phe Cys Leu Ala Ser Gly Glu Ile Ala Ser Asn
    130                 135                 140

<210> SEQ ID NO 82
<211> LENGTH: 148
<212> TYPE: PRT
<213> ORGANISM: Artificial Sequence
<220> FEATURE:
<223> OTHER INFORMATION: Synthetic peptide

<400> SEQUENCE: 82

Cys Leu Ser Tyr Asn Thr Glu Val Leu Thr Val Glu Tyr Gly Pro Leu
1               5                   10                  15

Pro Ile Gly Lys Ile Val Asp Glu Gln Ile His Cys Arg Val Tyr Ser
            20                  25                  30

Val Asp Glu Asn Gly Phe Val Tyr Thr Gln Ala Ile Ala Gln Trp His
        35                  40                  45

Asp Arg Gly Tyr Gln Glu Ile Phe Ala Tyr Glu Leu Ala Asp Gly Ser
    50                  55                  60

Val Ile Arg Ala Thr Lys Asp His Gln Phe Met Thr Glu Asp Gly Gln
65                  70                  75                  80

Met Phe Pro Ile Asp Glu Ile Trp Glu Lys Gly Leu Asp Leu Lys Lys
                85                  90                  95

Leu Pro Thr Val Gln Asp Leu Pro Ala Ala Val Gly Tyr Thr Val Ser
            100                 105                 110

Met Val Lys Ile Val Arg Arg Gln Ser Leu Gly Val Gln Asn Val Tyr
            115                 120                 125

Asp Ile Gly Val Glu Lys Asp His Asn Phe Cys Leu Ala Ser Gly Glu
        130                 135                 140

Ile Ala Ser Asn
145

<210> SEQ ID NO 83
<211> LENGTH: 149
<212> TYPE: PRT
<213> ORGANISM: Artificial Sequence
<220> FEATURE:
<223> OTHER INFORMATION: Synthetic peptide

<400> SEQUENCE: 83
```

```
Cys Leu Ala Ala Asp Thr Glu Val Leu Thr Val Glu Tyr Gly Pro Ile
1               5                   10                  15

Ala Ile Gly Lys Leu Val Glu Glu Asn Ile Arg Cys Gln Val Tyr Cys
            20                  25                  30

Cys Asn Pro Asp Gly Tyr Ile Tyr Ser Gln Pro Ile Gly Gln Trp His
            35                  40                  45

Gln Arg Gly Glu Gln Glu Val Ile Glu Tyr Glu Leu Ser Asp Gly Arg
        50                  55                  60

Ile Ile Arg Ala Thr Ala Asp His Arg Phe Met Thr Glu Glu Gly Glu
65                  70                  75                  80

Met Leu Ser Leu Asp Glu Ile Phe Glu Arg Ser Leu Glu Leu Lys Gln
                85                  90                  95

Ile Pro Thr Pro Leu Leu Ala Ile Ala Gln Pro Ser Pro Leu Ala Thr
            100                 105                 110

Ala Met Val Lys Ile Val Arg Arg Ser Leu Gly Val Gln Pro Val
            115                 120                 125

Tyr Asp Leu Gly Val Ala Thr Val His Asn Phe Val Leu Ala Asn Gly
        130                 135                 140

Leu Val Ala Ser Asn
145

<210> SEQ ID NO 84
<211> LENGTH: 143
<212> TYPE: PRT
<213> ORGANISM: Artificial Sequence
<220> FEATURE:
<223> OTHER INFORMATION: Synthetic peptide

<400> SEQUENCE: 84

Cys Leu Ala Gly Gly Thr Pro Val Val Thr Val Glu Tyr Gly Val Leu
1               5                   10                  15

Pro Ile Gln Thr Ile Val Glu Gln Glu Leu Leu Cys His Val Tyr Ser
            20                  25                  30

Val Asp Ala Gln Gly Leu Ile Tyr Ala Gln Leu Ile Glu Gln Trp His
            35                  40                  45

Gln Arg Gly Asp Arg Leu Leu Tyr Glu Tyr Glu Leu Glu Asn Gly Gln
        50                  55                  60

Met Ile Arg Ala Thr Pro Asp His Arg Phe Leu Thr Thr Thr Gly Glu
65                  70                  75                  80

Leu Leu Pro Ile Asp Glu Ile Phe Thr Gln Asn Leu Asp Leu Ala Ala
                85                  90                  95

Trp Ala Val Pro Asp Ser Leu Pro Arg Thr Ala Met Val Lys Ile Ile
            100                 105                 110

Arg Arg Lys Phe Ile Gly His Ala Pro Thr Tyr Asp Ile Gly Leu Ser
        115                 120                 125

Gln Asp His Asn Phe Leu Leu Gly Gln Gly Leu Ile Ala Ala Asn
        130                 135                 140

<210> SEQ ID NO 85
<211> LENGTH: 152
<212> TYPE: PRT
<213> ORGANISM: Artificial Sequence
<220> FEATURE:
<223> OTHER INFORMATION: Synthetic peptide

<400> SEQUENCE: 85

Cys Leu Ser Gly Glu Thr Ala Val Met Thr Val Glu Tyr Gly Ala Val
1               5                   10                  15
```

```
Pro Ile Arg Arg Leu Val Gln Glu Arg Leu Ser Cys His Val Tyr Ser
         20                  25                  30

Leu Asp Gly Gln Gly His Leu Tyr Thr Gln Pro Ile Ala Gln Trp His
     35                  40                  45

Phe Gln Gly Phe Arg Pro Val Tyr Glu Tyr Gln Leu Glu Asp Gly Ser
 50                  55                  60

Thr Ile Cys Ala Thr Pro Asp His Arg Phe Met Thr Thr Arg Gly Gln
 65                  70                  75                  80

Met Leu Pro Ile Glu Gln Ile Phe Gln Glu Gly Leu Glu Leu Trp Gln
                 85                  90                  95

Val Ala Ile Ala Pro Arg Gln Ala Leu Leu Gln Gly Leu Lys Pro Ala
            100                 105                 110

Val Gln Met Ser Cys Met Lys Ile Val Gly Arg Arg Leu Met Gly Trp
            115                 120                 125

Gln Ala Val Tyr Asp Ile Gly Leu Ala Ala Asp His Asn Phe Val Leu
        130                 135                 140

Ala Asn Gly Ala Ile Ala Ala Asn
    145                 150

<210> SEQ ID NO 86
<211> LENGTH: 137
<212> TYPE: PRT
<213> ORGANISM: Artificial Sequence
<220> FEATURE:
<223> OTHER INFORMATION: Synthetic peptide

<400> SEQUENCE: 86

Cys Leu Thr Tyr Glu Thr Glu Ile Met Thr Val Glu Tyr Gly Pro Leu
1               5                   10                  15

Pro Ile Gly Lys Ile Val Glu Tyr Arg Ile Glu Cys Thr Val Tyr Thr
             20                  25                  30

Val Asp Lys Asn Gly Tyr Ile Tyr Thr Gln Pro Ile Ala Gln Trp His
         35                  40                  45

Asn Arg Gly Met Gln Glu Val Tyr Glu Tyr Ser Leu Glu Asp Gly Thr
 50                  55                  60

Val Ile Arg Ala Thr Pro Glu His Lys Phe Met Thr Glu Asp Gly Gln
 65                  70                  75                  80

Met Leu Pro Ile Asp Glu Ile Phe Glu Arg Asn Leu Asp Leu Lys Cys
                 85                  90                  95

Leu Gly Thr Leu Glu Met Val Lys Ile Val Ser Arg Lys Leu Ala Lys
            100                 105                 110

Thr Glu Asn Val Tyr Asp Ile Gly Val Thr Lys Asp His Asn Phe Val
            115                 120                 125

Leu Ala Asn Gly Leu Ile Ala Ser Asn
        130                 135

<210> SEQ ID NO 87
<211> LENGTH: 152
<212> TYPE: PRT
<213> ORGANISM: Artificial Sequence
<220> FEATURE:
<223> OTHER INFORMATION: Synthetic peptide

<400> SEQUENCE: 87

Cys Leu Ser Gly Glu Thr Ala Val Met Thr Val Glu Tyr Gly Ala Ile
1               5                   10                  15

Pro Ile Arg Arg Leu Val Gln Glu Arg Leu Ile Cys Gln Val Tyr Ser
```

-continued

```
                    20                  25                  30
Leu Asp Pro Gln Gly His Leu Tyr Thr Gln Pro Ile Ala Gln Trp His
            35                  40                  45
Phe Gln Gly Phe Arg Pro Val Tyr Ala Tyr Gln Leu Glu Asp Gly Ser
    50                  55                  60
Thr Ile Cys Ala Thr Pro Asp His Arg Phe Met Thr Thr Ser Gly Gln
65                  70                  75                  80
Met Leu Pro Ile Glu Gln Ile Phe Arg Glu Gly Leu Glu Leu Trp Gln
                85                  90                  95
Val Ala Ile Ala Pro Pro Gly Ala Leu Ala Gln Gly Leu Lys Pro Ala
            100                 105                 110
Val Gln Met Ser Cys Met Lys Ile Val Gly Arg Arg Leu Val Gly Trp
        115                 120                 125
Gln Ala Val Tyr Asp Ile Gly Leu Ala Gly Asp His Asn Phe Leu Leu
    130                 135                 140
Ala Asn Gly Ala Ile Ala Ala Asn
145                 150
```

INTEIN MEDIATED PURIFICATION OF PROTEIN

CROSS-REFERENCE TO RELATED APPLICATIONS

This application is a National Stage of International Application No. PCT/US2014/011076, filed Jan. 10, 2014, which claims the benefit of U.S. Provisional Application No. 61/751,735, filed Jan. 11, 2013. The contents of each of which are incorporated by reference in their entirety.

STATEMENT OF FEDERALLY FUNDED RESEARCH

This invention was made with U.S. Government support under by the FA9550-12-1-0330 and 1150478 awarded by U.S. Air Force/AF Office of Scientific Research; and National Science Foundation, respectively. The government has certain rights in this invention.

TECHNICAL FIELD OF THE INVENTION

The present invention relates in general to the field of protein purification and protein cleavage.

BACKGROUND OF THE INVENTION

Without limiting the scope of the invention, its background is described in connection with intein mediated purification of protein.

U.S. Patent Application 2006/0141570 (filed Nov. 16, 2005) discloses purification of recombinant proteins performed by expressing in a host cell a fusion protein comprising a product protein domain, an intein, and at least one aggregator protein domain, wherein the aggregator protein domain comprises a protein that is capable of specific association with granules of polyhydroxyalkanoate (PHA).

European patent application EP 1117693 B1 (filed Sep. 30, 1999) discloses an in vitro method for producing a semi-synthetic fusion protein, whereby a target protein fused to an intein is selectively cleaved in a first step with a thiol reagent, forming a carboxyl-terminal thioester of the target protein and releasing the target protein from the intein. In a subsequent step, a desired, synthetic, protein or peptide having an amino-terminal cysteine is ligated to the target protein. Standard thiol-reagents such as DTT, or thiol-reagents optimized for ligation such as the odorless MESNA, may be used in the first step. The method is said to permit direct ligation of a desired peptide to a thioester bond that had linked a target protein to an intein. An in vivo variation of the method is said to permit production of a cytotoxic protein: a truncated, inactive, form of the protein fused to an intein is introduced in vivo, this fusion product is then selectively cleaved, and a synthetic protein or peptide is subsequently ligated at a carboxyl-terminal thioester of the target protein in order to restore the native activity of the cytotoxic protein.

European patent application EP 1151117 A4 (filed Aug. 10, 2005) discloses a method for the ligation of expressed proteins, which utilizes inteins, for example the RIR1 intein from *Methanobacterium thermotrophicum*. Constructs of the Mth RIR1 intein in which either the C-terminal asparagine or N-terminal cysteine of the intein are replaced with alanine enable the facile isolation of a protein with a specified N-terminal, for example, cysteine for use in the fusion of two or more expressed proteins. The method involves the steps of generating a C-terminal thioester-tagged target protein and a second target protein having a specified N-terminal via inteins, such as the modified Mth RIR1 intein, and ligating these proteins. A similar method for producing a cyclic or polymerized protein is provided. Modified inteins engineered to cleave at their C-terminus or N-terminus, respectively, and DNA and plasmids encoding these modified inteins are also provided.

SUMMARY OF THE INVENTION

The present invention includes methods of purifying a protein of interest (POI) comprising contacting a first fusion protein comprising the POI fused to the C-terminus of an intein C-fragment with a second fusion protein comprising an intein N-fragment and a purification tag to form a complex between the first fusion protein and the second fusion protein, cleaving the POI from the intein C-fragment, wherein the protein is released from the complex; and isolating the POI. In certain aspects, the intein is a split intein, a naturally split intein DnaE from *Nostoc punctiforme*, and/or selected from the group consisting of Ssp from *Synechocystis* species, Aha from *Aphanothece halophytica*, Aov from *Aphanizomenon ovalisporum*, Asp from *Anabaena* species, Ava from *Anabaena variabilis*, Cra(CS505) from *Cylindrospermopsis raciborskii*, Csp(CCYO110) from *Cyanotilece* species, Csp(PCC8801) from *Cyanothece* species, Cwa from *Crocosphaera watsonii*, Maer(NIES843) from *Microcystis aeruginosa*, Mcht (PCC7420)-2 from *Microcoleus chthonoplastes*, Oli from *Oscillatoria limnetica*, Sel(PC7942) from *Synechococcus elongates*, Ssp [PCC7002) from *Synechococcus* species, Tel from *Thernlosynechococcus elongates*, Ter-3 from *Trichodesmium erythraeum*, and Tvu from *Thernlosynechococcus vulcanus*. In certain aspects, the intein C-fragment carries a mutation that significantly retards N-terminal cleavage, suppresses trans-splicing ability, and increases C-terminal cleavage rate and efficiency compared to a non-mutated intein C-fragment, the C-intein fragment carries an Asp118Gly mutation, within the C-intein fragment, and/or intein C-fragment comprises the amino acid sequence of SEQ ID NO: 37. In certain aspects, the purification tag is located at an intein split junction, which is at the C-terminus of the intein N-fragment, the intein N-fragment carries a mutation that abolishes N-terminal cleavage activity, and/or the intein N-fragment comprises the amino acid sequence of SEQ ID NO: 39. In certain aspects, the purification tag is an affinity tag selected from the group consisting of chitin-binding domain (CBD), 6× Histidine, maltose binding domain (MBP), glutathione S-transferase (GST), and combinations thereof. In certain aspects, the purification tag is an affinity tag selected from the group consisting of SEQ ID NO: 38, and/or the second fusion protein comprises the amino acid sequence selected from a group consisting of SEQ ID NO: 4, 10, 24, and combinations thereof. In certain aspects, the purification tag is elastin-like peptide (ELP), and/or the purification tag is a precipitation tag comprising the amino acid sequence of SEQ ID NO: 38. In certain aspects, the purification tag is a precipitation tag and the method further comprises: precipitating the complex, washing the complex, solubilizing the complex, and inducing intein cleavage; in certain aspects, precipitating the complex and washing the complex is conducted in the presence of one or more cleavage inhibitors. In certain aspects, the purification tag is an affinity tag and the method further comprises binding the complex to an affinity resin capable of binding the affinity tag; and washing the complex with a washing buffer before the cleavage step;

inducing intein cleavage. In certain aspects, binding the complex and washing the complex is conducted in the presence of one or more cleavage inhibitors. In certain aspects, inducing intein cleavage is conducted by reducing agents or chelating agents. In certain aspects, inducing intein cleavage comprises contacting the complex with one or more chelating agents selected from a group consisting of ethyleneglycolaminoethylestertetraacetic acid (EGTA) diethylenetriaminepentaacetic acid (DTPA) dipicolinic acid (DPA) nitrilotriacetic acid (NTA). In certain aspects, the methods further comprise incubating the complex with a first washing buffer before inducing cleavage, wherein the washing buffer inhibits cleavage and/or comprises a cleavage inhibitor selected from the group consisting of $Zn^{2+}$, $Cu^{2}$, $Mg^{2+}$, $Co^{2+}$, $Mn^{2+}$, and $Fe^{2+}$; and/or washing the complex with a first washing buffer before inducing cleavage, wherein the washing buffer comprises a cleavage inhibitor that inhibits the C-terminal cleavage reaction. In certain aspects, the C-terminal protein cleavage comprises inducing a thio-induced C-terminal cleavage; inducing a C-terminal protein cleavage comprising inducing a thio-induced C-terminal cleavage in the presence of a cleavage inducer selected from the group consisting of DTT, $Zn^{2+}$ chelating agents, trialkylphosphine (tris(2-carboxyethyl) phosphine (TCEP), 2-mercaptoethanol, cysteine, and combinations thereof; inducing a C-terminal protein cleavage comprising inducing intein cleavage by chelating a cleavage inhibitor using chelating agents. In certain aspects, the purification tag is an affinity tag and the method further comprises binding the complex to an affinity resin, wherein separating the POI from the complex comprises separating the POI from the affinity resin to which the complex is bound; and/or the purification tag is a precipitation tag, wherein the method further comprises precipitating the complex, wherein a precipitated complex is formed and wherein separating the POI from the complex comprises solubilizing the precipitated complex, wherein a solubilized complex is formed; and separating the POI from the solubilized complex. In certain aspects, the methods further comprise regenerating the second fusion protein by dissociating the intein C-fragment from the second fusion protein. In certain aspects, the POI is selected from a bioactive peptide, an enzyme, an enzyme inhibitor, an enzymatic catalytic site, a DNA-binding protein, an isolated protein domain, a ligand for receptors, a receptor, a growth factor, a cytokine, a structural protein, an antibody, an antibody fragment, an epitope, an epitope-binding region, an antigen, an allergen, and contiguous or overlapping fragments of a protein sequence of interest. In certain aspects, the purification tag is an affinity tag and the method further comprises binding the complex to an affinity resign before inducing the C-terminal protein cleavage; and regenerating the affinity resign by dissociating the intein C-fragment from the second fusion protein. In certain aspects, the methods further comprise regenerating the second fusion protein by dissociating the intein C-fragment from the second fusion protein and again contacting the regenerated second fusion protein with the first fusion protein. In certain aspects, the purification tag is an affinity tag and the second fusion protein is bound to an affinity resin selected from the group consisting of Chitin beads, Nickel resin, amylose resin, glutathione, and combinations thereof; the purification tag is a precipitation tag that mediates precipitation of the second fusion protein, and wherein the complex is precipitated.

The invention includes embodiments of methods of purifying a protein of interest (POI) comprising providing a first fusion protein comprising the POI and an intein C-fragment, wherein the POI is fused to the C-terminus of the intein C-fragment, wherein the intein is a naturally split intein DnaE, and the intein C-fragment carries a Asp118Gly mutation within the intein C-fragment; providing a second fusion protein comprising an intein N-fragment and a purification tag, wherein the purification tag is inserted at the intein split junction at the C-terminus of the intein N-fragment, wherein the intein N-fragment carries a mutation that abolishes N-terminal cleavage activity; contacting the first fusion protein with the second fusion protein in binding buffer, wherein the second fusion protein is attached to a resin that binds to the purification tag, wherein the purification tag is capable of specifically binding a purification resin, wherein a complex between the first fusion protein and the second fusion protein is formed, wherein the binding buffer inhibits a C-terminal protein cleavage of the first fusion protein between the POI and the intein C-fragment; inducing the C-terminal protein cleavage of the first fusion protein between the POI and the intein C-fragment whereby the POI is released; and separating the POI from the first fusion protein and the C-terminus of the intein C-fragment.

The invention also includes embodiments of methods of purifying a protein of interest (POI) comprising providing a first fusion protein comprising the POI and an intein C-fragment, wherein the POI is fused to the C-terminus of the intein C-fragment, wherein the intein is a naturally split intein DnaE, and the intein C-fragment carries a Asp118Gly mutation within the intein C-fragment; providing a second fusion protein comprising an intein N-fragment and a precipitation tag, wherein the precipitation tag is inserted at the intein split junction, which is the C-terminus of the intein N-fragment, wherein the intein N-fragment carries a mutation that abolishes N-terminal cleavage activity; contacting the first fusion protein with the second fusion protein in binding buffer, wherein a complex between the first fusion protein and the second fusion protein is formed, wherein the binding buffer inhibits a C-terminal protein cleavage of the first fusion protein between the POI and the intein C-fragment; precipitating the complex between the first fusion protein and the second fusion protein; solubilizing the complex in low salt buffer, inducing the C-terminal protein cleavage of the first fusion protein between the POI and the intein C-fragment whereby the POI is released; and separating the POI from the complex between the first fusion protein and the second fusion protein by a second round of precipitation.

The invention includes embodiments of fusion proteins comprising a protein of interest (POI) and an intein C-fragment, wherein the POI is fused to the C-terminus of the intein C-fragment, wherein the intein is a naturally split intein DnaE, and the intein C-fragment carries a Asp118Gly mutation within the intein C-fragment. In certain aspects, the fusion protein comprises SEQ ID NO: 37. In certain aspects, POI is selected from a bioactive peptide, an enzyme, an enzyme inhibitor, an enzymatic catalytic site, a DNA-binding protein, an isolated protein domain, a ligand for receptors, a receptor, a growth factor, a cytokine, an antibody, an antibody fragment, an epitope, an epitope-binding region, an antigen, an allergen, and contiguous or overlapping fragments of a protein sequence of interest.

The invention includes embodiments of fusion proteins comprising an intein N-fragment and a purification tag, wherein the purification tag is located at the intein split junction, which is the C-terminus of the intein N-fragment, wherein the intein N-fragment carries a mutation that abolishes N-terminal cleavage activity. In certain aspects, the fusion protein comprises SEQ ID NO: 10, 24, SEQ ID NO: 21, 22; SEQ ID NO: 4, SEQ ID NO: 23, or combinations thereof.

The invention includes embodiments of vectors comprising a first DNA element encoding a C-terminus of a intein C-fragment operably linked to a promoter, wherein the intein C-fragment carries a mutation that suppresses N-terminal cleavage and increases C-terminal cleavage compared to a non-mutated intein C-fragment; wherein the vector carries a cloning site that enables the insertion of a second DNA element encoding a protein of interest (POI) to the C-terminus of the intein C-fragment. In certain aspects, the intein is a naturally split intein DnaE from *Nostoc punctiforme*, and the C-intein fragment carries a Asp118Gly mutation within the C-intein fragment. In certain aspects, the first DNA element encodes the amino acid sequence of SEQ ID NO: 37; and or the first DNA element comprises the SEQ ID NO: 40. In certain aspects, the POI is selected from a bioactive peptide, an enzyme, an enzyme inhibitor, an enzymatic catalytic site, a DNA-binding protein, an isolated protein domain, a ligand for receptors, a receptor, a growth factor, a cytokine, an antibody, an antibody fragment, an epitope, an epitope-binding region, an antigen, an allergen, and contiguous or overlapping fragments of a protein sequence of interest.

The invention includes embodiments of vectors comprising DNA elements encoding a fusion protein comprising a intein N-fragment and a purification tag operably linked to a promoter, wherein the purification tag is located at the intein split junction, which is the C-terminus of the intein N-fragment, wherein the intein N-fragment carries a mutation that abolishes N-terminal cleavage activity. In certain aspects, the purification tag is an affinity tag; and/or the purification tag is a precipitation tag. In certain aspects, the DNA element comprises SEQ ID NO: 23 or SEQ ID NO: 41.

The invention includes embodiments of kits for isolating a protein of interest (POI) comprising a first vector comprising a first DNA element encoding a C-terminus of a intein C-fragment operably linked to a promoter, wherein the intein C-fragment carries a mutation that suppresses N-terminal cleavage and increases C-terminal cleavage compared to a non-mutated intein C-fragment, wherein the first vector carries a cloning site that enables the insertion of a second DNA element encoding a POI to the C-terminus of the intein C-fragment; a second vector comprising a second DNA element encoding a fusion protein comprising a intein N-fragment and a purification tag operably linked to a promoter, wherein the purification tag is located at the intein split junction, which is the C-terminus of the intein N-fragment, wherein the intein N-fragment carries a mutation that abolishes N-terminal cleavage activity; or a fusion protein comprising a intein N-fragment and a purification tag that is located at the intein split junction, which is the C-terminus of the intein N-fragment, wherein the intein N-fragment carries a mutation that abolishes N-terminal cleavage activity; instruction to insert a DNA element encoding the POI into the cloning site of the first vector; and instruction to isolate the POI.

The invention includes embodiments of methods of purifying a protein of interest (POI) comprising contacting a first fusion protein comprising the POI fused to the C-terminus of an intein C-fragment with a second fusion protein comprising an intein N-fragment and a purification tag to form a complex between the first fusion protein and the second fusion protein, wherein the intein C-fragment carries a mutation that significantly retards N-terminal cleavage, suppresses trans-splicing ability, and increases C-terminal cleavage rate and efficiency compared to a non-mutated intein C-fragment; cleaving the POI from the intein C-fragment, wherein the protein is released from the complex; and isolating the POI. In certain aspects, the intein is a naturally split intein DnaE, and the C-intein fragment carries a Asp118Gly mutation, within the C-intein fragment.

The invention includes embodiments of methods of purifying a protein of interest (POI) comprising providing a first fusion protein comprising the POI and an intein C-fragment, wherein the POI is fused to the C-terminus of the intein C-fragment, wherein the intein is a naturally split intein DnaE, and the intein C-fragment carries a Asp118Gly mutation within the intein C-fragment; providing a second fusion protein comprising an intein N-fragment and a purification tag, wherein the intein N-fragment carries a mutation that abolishes N-terminal cleavage activity; contacting the first fusion protein with the second fusion protein in binding buffer, wherein the second fusion protein is attached to a resin that binds to the purification tag, wherein the purification tag is capable of specifically binding a purification resin, wherein a complex between the first fusion protein and the second fusion protein is formed, wherein the binding buffer inhibits a C-terminal protein cleavage of the first fusion protein between the POI and the intein C-fragment; inducing the C-terminal protein cleavage of the first fusion protein between the POI and the intein C-fragment whereby the POI is released; and separating the POI from the first fusion protein and the C-terminus of the intein C-fragment.

The invention includes embodiments of fusion proteins comprising a protein of interest (POI) and an intein C-fragment, wherein the POI is fused to the C-terminus of the intein C-fragment, wherein the intein is a naturally split intein DnaE, and the intein C-fragment carries a Asp118Gly mutation within the intein C-fragment.

The invention includes embodiments of kits for isolating a protein of interest (POI) comprising a first vector comprising a first DNA element encoding a C-terminus of a intein C-fragment operably linked to a promoter, wherein the intein C-fragment carries a Asp118Gly mutation within the intein C-fragment, wherein the first vector carries a cloning site that enables the insertion of a second DNA element encoding a POI to the C-terminus of the intein C-fragment; a second vector comprising a second DNA element encoding a fusion protein comprising a intein N-fragment and a purification tag operably linked to a promoter; or a fusion protein comprising a intein N-fragment and a purification tag; instruction to insert a DNA element encoding the POI into the cloning site of the first vector; and instruction to isolate the POI.

The invention includes embodiments of methods of purifying a protein of interest (POI) comprising contacting a first fusion protein comprising the POI fused to the C-terminus of an intein C-fragment with a second fusion protein comprising an intein N-fragment and a purification tag to form a complex between the first fusion protein and the second fusion protein, wherein the purification tag is located at an intein split junction, which is at the C-terminus of the intein N-fragment; cleaving the POI from the intein C-fragment, wherein the protein is released from the complex; and isolating the POI.

BRIEF DESCRIPTION OF THE DRAWINGS

For a more complete understanding of the features and advantages of the present invention, reference is now made to the detailed description of the invention along with the accompanying figures and in which:

FIG. 1 shows a table regarding reported apparent half-lives of various continuous and split inteins. In the table, superscript a: is Half-life for SspDanE and split SspDnaB calculated from pseudo first order kobs reported in the reference; superscript b is: SspDnaE C-terminal cleavage rate after N-terminal cleavage; and superscript c: is Continuous intein; 2: Waugh, D. S. An overview of enzymatic reagents for the removal of affinity tags. Protein Expr. Purif. 80, 283-293 (2011). 3: Malakhov, M. P. et al. SUMO fusions and SUMO-specific protease for efficient expression and purification of proteins. J Struct. Funct. Genomics 5, 75-86 (2004). 4: Mathys, S. et al. Characterization of a self-splicing mini-intein and its conversion into autocatalytic N- and C-terminal cleavage elements: facile production of protein building blocks for protein ligation. Gene 231, 1-13 (1999). 5: Lew, B. M., Mills, K. V. & Paulus, H. Characteristics of protein splicing in trans mediated by a semisynthetic split intein. Biopolymers 51, 355-362 (1999). 7: Southworth, M. W., Amaya, K., Evans, T. C., Xu, M. Q. & Perler, F. B. Purification of proteins fused to either the amino or carboxy terminus of the Mycobacterium xenopi gyrase A intein. BioTechniques 27, 110-114, 116, 118-120 (1999); 8: Li, Y. F. Self-cleaving fusion tags for recombinant protein production. Biotechnology Letters 33, 869-881 (2011).

FIG. 3 contains a list of the various fusion protein constructs used. The constructs include the engineered intein pairs intended for characterization as well as the proteins of interest used for sample purification.

FIG. 5A illustrates the Intein trans-splicing mechanism. FIG. 5B illustrates products resulting from different intein reactions. Mutation of the last asparagine and the first cysteine to alanine render most inteins N- and C-terminal cleaving, respectively. FIG. 5C shows structural alignment of NpuDnaE intein (red, pdb: 2 keq) with mini-MtuRecA intein (yellow, pdb: 2 IMZ). Conserved catalytic residues for Npu DnaE and mini-MtuRecA inteins are highlighted in color green and orche, respectively.

FIG. 6 shows sequence alignment of DnaE inteins from Ssp and Npu, and mini-MtuRecA intein. ||: break point for IN and IC for DnaE intein. Active site residues as shown in FIG. 5C and FIG. 21 are highlighted in red. The Asn118 residue is highlighted in magenta. Numbers correspond to the NpuDnaE residue (SEQ ID NOS: 67-69).

FIGS. 7A, 7B, and 7C show catalytic activity of mutant C. Reaction between CBD-N (2) and C*-GFP (4) at 22° C. in the absence or presence of reducing agent DTT (FIG. 7A) or TCEP (FIG. 7B). 2N: dimer complex of CBD-N (2). It disappears in samples treated with higher concentration of β-mercaptoethanol and boiled for longer period. GFP and C* are the cleaved C-extein and C-intein, respectively. N is the cleaved N-intein. Cleaved N-extein CBD is not visible on the SDS-gel but can be detected on Western Blot for samples incubated with DTT (data not shown). "+" denotes unidentified bands. FIG. 7C shows a time course of the disappearance of C*-GFP due to C-terminal cleavage at different temperatures. The error bar represents the standard deviation from 3 independent experiments.

FIG. 9A shows a comparison of the current intein system or design for tag removal vs. the conventional system or design. FIG. 9B provides a representation of fusion proteins before and after intein association. The intein N-fragment (yellow) and C-fragment (brown) are adapted from the NMR structure of NpuDnaE (PDB code: 2 keq).

FIGS. 10A to 10D provide C-terminal cleavage kinetics characterization of the engineered intein system. FIGS. 10A and 10B show SDS-gel (12% acrylamide) of the reaction between NC1A-CBD (construct 1) and C*-PTDH (construct 3) (continuous line) performed at 22° C. and 6° C., respectively, in pH 8 buffer containing 50 mM DTT quantified using densitometry analysis. The cleaved C* is 4 kDa and is not visible from the gel. FIG. 10C provide C-terminal cleavage kinetics of the wild-type intein C-PTDH using NC1A-CBD at 22° C. in pH 8 buffer containing 50 mM DTT quantified using densitometry analysis. FIG. 10D depicts a time course of the disappearance of C/C*-PTDH due to C-terminal cleavage at different temperatures. Time course for the first 5 minutes is shown in the inset. The error bars represent the standard deviation from 2 independent studies.

FIG. 11A shows a SDS-gel of the reaction between NC1A-CBD (construct 12) and C*-PTDH (construct 6) performed under different buffer conditions at 22° C. '+' denotes impurities. FIG. 11B depicts a calculated percentage of C-terminal cleavage under different conditions. The error bars represent the standard deviation from 2 independent experiments.

FIG. 13 is a schematic representation of chitin-mediated chromatography purification method. Lysate of C*-POI is passed through column prebound with NC1A-CBD in the presence of 0.5 mM ZnCl2. After washing, intein C-terminal cleavage reaction is induced by the addition of DTT and purified POI can be collected in the flow-through. The column is then regenerated by washing in pH 11.4 buffer to dissociate the intein complex.

FIG. 17A shows SDS-PAGE (10% acrylamide) analysis of samples collected during the purification of PTDH via reversible precipitation of ELP. Lane 1, pre-purified ELP-N (5); lane 2, soluble lysate containing C*-PTDH (3); lane 3, mixture of samples from lanes 1 and 2; lane 4, supernatant after the precipitation of the ELP complex; lane 5 and 6, mixture of ELP-N and C*-PTDH at t=0 and 3 h of intein reaction at 22° C., respectively; lanes 7, ELP precipitant after 3 h intein reaction; lanes 8 and 9, supernatant containing purified PTDH after ammonium sulfate precipitation after 3 and 20 h intein reaction, respectively. An equivalent amount of protein was loaded into each lane. Black arrow indicates the uncleaved C*-PTDH. FIG. 17B shows images taken over the course of DsRed purification via reversible precipitation of ELP. FIG. 17C shows SDS-PAGE (12% acrylamide) analysis of samples collected during the purification of GFP via chitin column. Lane 1 and 2, soluble lysate containing CBD-N (2) and C*-GFP (3), respectively; lane 3, sample taken from chitin beads after binding of CBD-N (2); lane 4, sample taken from chitin beads immediately after binding of C*-GFP (4); lane 5, sample after 3 hours of intein reaction; lane 6, sample taken from chitin beads after elution of GFP; lane 7, elution containing purified GFP. An equivalent amount of protein was loaded into each lane, except for lanes 1 and 2.

FIG. 19 provides protein purification and quantification via ELP-precipitation. $^a$: Intein reaction time at 22° C.; $^b$: Purification yields were determined from 25 mg of wet E. coli pellet. $^c$: Percent recovery was estimated using densitometry analysis of SDS-PAGE. $^d$: Protein purified with 3 h intein reaction time is used. One β-Galactosidase unit is defined as the amount of protein needed to hydrolyze 1.0 µmole of ONPG per minute at 22° C. DTT interferes with the absorbance of the products of PTDH and CAT reaction, preventing accurate activity measurement of these proteins. Activity of MBP was analyzed qualitatively only. $^e$: ND, Not determined. $^f$: Numbers in parenthesis represent percent recovery based on activity assay.

FIG. 20 shows ELP pull-down efficiency and purification yield calculated based on activity assay on samples loaded onto SDS-PAGE gels in FIG. 21. a: Pull-down efficiency= (Lane 2 activity−Lane 4 activity)/Lane 2 activity×100%. b: Yield (3 h)=Lane 8 activity/Lane 2 activity×100%. c: Yield (20 h)=Lane 9 activity/Lane 2 activity×100%.

FIGS. 21A and 21B depict residues that participate in a charge relay needed for C-terminal cleavage. FIG. 21A is a schematic of the first step of charge relay responsible for C-terminal asparagine cyclization. Corresponding residues in SspDnaE (orange) and NpuDnaE (black) are indicated. FIG. 21B shows a structural alignment of charge relay residues in SspDnaE (orange, pdb: 1zd7) and NpuDnaE (elemental colors, pdb: 2 keq). Asn137 forms H-bond with Asp117 in NpuDnaE, rendering it less suited to participation in the charge relay.

FIG. 23 lists suitable DnaE Inteins as well as the genus, species and strain from which they can be derived.

DETAILED DESCRIPTION OF THE INVENTION

Figure 2A:
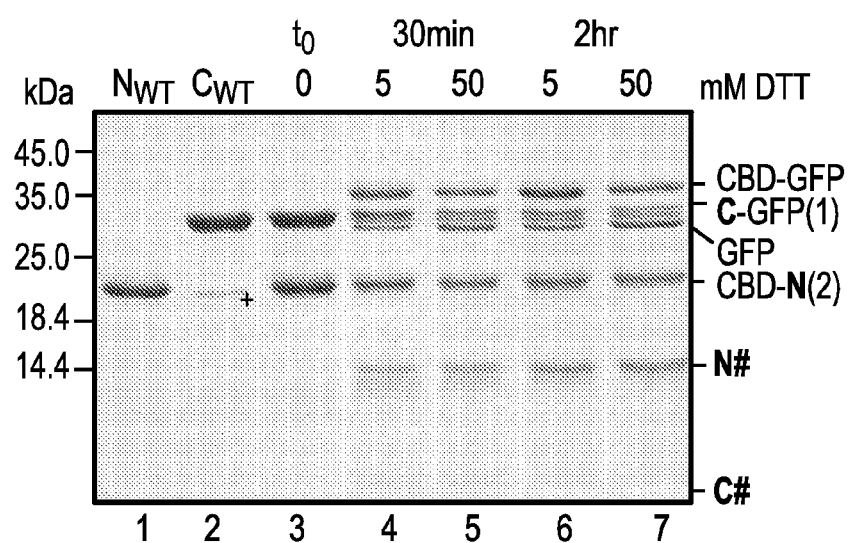
FIGS. 2A and 2B show reaction between C-GFP (1) and CBD-NpuN (2) (FIG. 2A) or CBD-NC1A (4) (FIG. 2B) at 22° C. in the absence or presence of 5 or 50 mM DTT (12% acrylamide). CBD-GFP is the trans-spliced product and GFP is the cleaved C-extein. "+" denotes impurities.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an," and "the" are not intended to refer to only a singular entity but include the general class of which a specific example may be used for illustration. The terminology herein is used to describe specific embodiments of the invention, but their usage does not delimit the invention, except as outlined in the claims.

The term "gene" is used to refer to a functional protein, polypeptide or peptide-encoding unit. As will be understood by those in the art, this functional term includes both genomic sequences, cDNA sequences, or fragments or combinations thereof, as well as gene products, including those that may have been altered by the hand of man. Purified genes, nucleic acids, protein and the like are used to refer to these entities when identified and separated from at least one contaminating nucleic acid or protein with which it is ordinarily associated.

As used herein, the term "vector" is used in reference to nucleic acid molecules that transfer DNA segment(s) from one cell to another. The vector may be further defined as one designed to propagate specific sequences, or as an expression vector that includes a promoter operatively linked to the specific sequence, or one designed to cause such a promoter to be introduced. The vector may exist in a state independent of the host cell chromosome, or may be integrated into the host cell chromosome.

The term "host cell" refers to cells that have been engineered to contain nucleic acid segments or altered segments, whether archeal, prokaryotic, or eukaryotic. Thus, engineered, or recombinant cells, are distinguishable from naturally occurring cells that do not contain recombinantly introduced genes through the hand of man.

The term "altered", or "alterations" or "modified" with reference to nucleic acid or polypeptide sequences is meant to include changes such as insertions, deletions, substitutions, fusions with related or unrelated sequences, such as might occur by the hand of man, or those that may occur naturally such as polymorphisms, alleles and other structural types. Alterations encompass genomic DNA and RNA sequences that may differ with respect to their hybridization properties using a given hybridization probe. Alterations of polynucleotide sequences, or fragments thereof, include those that increase, decrease, or have no effect on functionality. Alterations of polypeptides refer to those that have been changed by recombinant DNA engineering, chemical, or biochemical modifications, such as amino acid derivatives or conjugates, or post-translational modifications.

The term "control sequences" refers to DNA sequences necessary for the expression of an operably linked coding sequence in a particular host organism. The control sequences that are suitable for prokaryotes, for example, include a promoter, optionally an operator sequence, a ribosome binding site, and transcriptional terminators. Highly regulated inducible promoters that suppress Fab' polypeptide synthesis at levels below growth-inhibitory amounts while the cell culture is growing and maturing, for example, during the log phase may be used.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it effects the transcription of the sequence; or a ribosome binding site is operably linked to e coding sequence if it is positioned so as to facilitate translation. Generally, "operably linked" means that the DNA sequences being linked are contiguous and, in the case of a secretory leader, contiguous and in same reading frame. Enhancers do not have to be contiguous. Linking is accomplished by ligation at convenient restriction sites. If such sites do not exist, then synthetic oligonucleotide adaptors or linkers are used in accord with conventional practice.

An "exogenous" element is defined herein to mean a nucleic acid sequence that is foreign to the cell, or homologous to the cell but in a position within the host cell nucleic acid in which the element is ordinarily not found.

As used herein, the expressions "cell" and "cell culture" are used interchangeably end all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Different designations are will be clear from the contextually clear.

"Plasmids" are designated by a lower case p preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al. (Nucleic Acids Res. 1981. 9:6103-6114), and Goeddel et al. (Nucleic Acids Res. 1980. 8:4057).

"Preparation" of DNA from cells means isolating the plasmid DNA from a culture of the host cells. Methods used commonly for DNA preparation are the large and small-scale plasmid preparations described in sections 1.25-1.33 of Sambrook et al., (Molecular Cloning: A Laboratory Manual New York: Cold Spring Harbor Laboratory Press, 1989). DNA preparations are purified by methods well known in the art (see section 1.40 of Sambrook et al., supra).

As used herein, the term "protein-protein complex" or "protein complex" refers to an association of more than one protein. The proteins of the complex may be associated by a variety of means, or by any combination of means, including but not limited to functional, stereochemical, conformational, biochemical, or electrostatic association. It is intended that the term encompass associations of any number of proteins.

As used herein the terms "protein", "polypeptide" or "peptide" refer to compounds comprising amino acids joined via peptide bonds and are used interchangeably.

The term "protein of interest" as used here refers to a protein, the function and/or expression of which is desired to be isolated or purified using the methods and constructs of the present invention. The present invention may be useful in regard to the isolation and/or purification of any protein expressed by any gene from any organism, whether of a prokaryotic or eukaryotic organism.

The terms "a sequence essentially as set forth in SEQ ID NO. (#)", "a sequence similar to", "nucleotide sequence" and similar terms, with respect to nucleotides, refers to sequences that substantially correspond to any portion of the sequence identified herein as SEQ ID NO.: 1. These terms refer to synthetic as well as naturally-derived molecules and includes sequences that possess biologically, immunologically, experimentally, or otherwise functionally equivalent activity, for instance with respect to hybridization by nucleic acid segments, or the ability to encode all or portions of activities. Naturally, these terms are meant to include information in such a sequence as specified by its linear order.

The term "homology" refers to the extent to which two nucleic acids are complementary. There may be partial or complete homology. A partially complementary sequence is one that at least partially inhibits a completely complementary sequence from hybridizing to a target nucleic acid and is referred to using the functional term "substantially homologous." The degree or extent of hybridization may be examined using a hybridization or other assay (such as a competitive PCR assay) and is meant, as will be known to those of skill in the art, to include specific interaction even at low stringency.

The inhibition of hybridization of the completely complementary sequence to the target sequence may also be examined using a hybridization assay involving a solid support (e.g., Southern or Northern blot, solution hybridization and the like) under conditions of low stringency. Low stringency conditions may be used to identify the binding of two sequences to one another while still being specific (i.e., selective). The absence of non-specific binding may be tested by the use of a second target that lacks even a partial degree of complementarity (e.g., less than about 30% identity). In the absence of non-specific binding, the probe will not hybridize to the second non-complementary target and the original interaction will be found to be selective. Low stringency conditions are generally conditions equivalent to binding or hybridization at 42 degrees Centigrade in a solution consisting of 5×SSPE (43.8 g/l NaCl, 6.9 g/l NaH2PO4-H2O and 1.85 g/l EDTA, pH 7.4), 0.1% SDS, 5×Denhardt's reagent (50×Denhardt's contains per 500 ml: 5 g Ficoll (Type 400, Pharmacia), 5 g BSA (Fraction V; Sigma) and 100 micrograms/ml denatured salmon sperm DNA); followed by washing in a solution comprising 5×SSPE, 0.1% SDS at 42 degrees Centigrade when a probe of about 500 nucleotides in length is employed. The art knows that numerous equivalent conditions may be employed to achieve low stringency conditions. Factors that affect the level of stringency include: the length and nature (DNA, RNA, base composition) of the probe and nature of the target (DNA, RNA, base composition, present in solution or immobilized, etc.) and the concentration of the salts and other components (e.g., formamide, dextran sulfate, polyethylene glycol). Likewise, the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, inclusion of formamide, etc.).

The present inventors have developed an ultra-rapid method (SIRP) that allows the use of an engineered split intein to purify tagless proteins in a short amount of time. In certain embodiments, this technology provides a powerful new tool for the purification of tagless proteins in bench-scale applications. Certain embodiments employ low cost of chitin beads. Other embodiments employ low-cost CBD-binding amorphous cellulosic matrices as affinity supports for CBD. This makes the application of this intein-mediated approach as an affinity-based step for large-scale protein purification attractive. Other embodiments employ precipitation of Elastin-Like-Polypeptide (ELP).

Figure 24A:
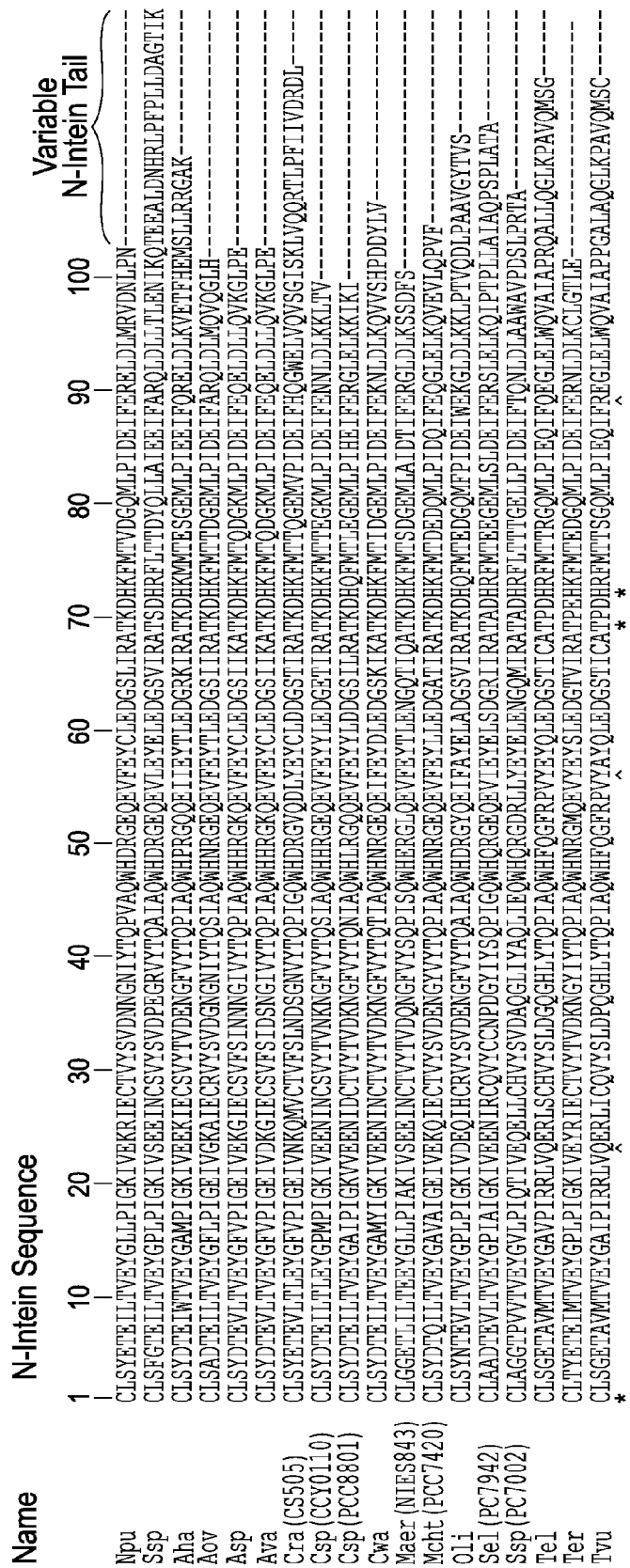
FIG. 24 provided the N-Intein as well as the C-Intein amino acid sequence (SEQ ID NOS. 70-87).

Some embodiments include inteins listed and shown in FIG. 23 and FIG. 24.

The inventors recognize that rapid and efficient tag removal is a significant problem in recombinant protein purification. Using an engineered C-terminal cleaving naturally split DnaE intein from *Nostoc punctiforme*, the inventors developed a split intein mediated ultra-rapid purification of tagless protein (SIRP) that enables the purification of tagless recombinant protein from *E. coli* lysate in less than 1 hour.

The inventors recognize that affinity tags have simplified the purification of recombinant proteins and are invaluable to modern biotechnology. However, the additional time and the high cost associated with proteases needed for tag removal have greatly hampered the usefulness of affinity tags in large-scale industrial processes, as no simple and low-cost method exists to date for affinity tag removal. Most proteases used for tag removal suffer from either low specificity or activity, and they leave certain amino acids in the target protein after cleavage. The recently discovered SUMO-protease exhibits both high specificity and efficiency (>90% completion within 20 minutes at 22° C.). However, the cost to cleave 1 g of recombinant protein using SUMO-protease (Life Technologies) is $673,000, prohibiting its use in most applications.

The inventors recognize that protease-free protein purification processes using inteins engineered to undergo N-/C-terminal cleavage reaction in acidic (pH 6) or reducing environments have been developed. Inteins are proteins that catalyze a splicing reaction that joins the associated N- and C-exteins via a peptide bond. Inteins can be engineered to perform a single cleavage reaction at their N- or C-terminus in acidic (pH 6) or reducing environments and these engineered inteins can be exploited for stimulus-responsive tag removal in protein purification applications. However, the engineered inteins used in these protein purification applications have invariably proved inefficient, requiring at least overnight incubation to achieve significant cleavage/tag-removal (FIG. 1). Also, these systems suffer premature cleavage and release of the target protein in vivo. Thus, unless a slow-acting intein is used, target protein expression conditions often need to be optimized to minimize in vivo intein cleavage. In some cases, even after optimization of expression conditions, premature protein cleavage still significantly impacts target protein yields. The present inventors created an intein-mediated system for the purification of tag-free recombinant protein that performs the cleavage/tag-removal reaction in a much shorter time without the possibility of intein-induced premature in vivo cleavage, thus making this method economical and amenable to widespread use.

In certain embodiments, the present inventors recognize a solution to prevent in vivo target protein cleavage using split-inteins whose catalytic residues are split between two peptide chains: the N-terminal intein (IN) and the C-terminal intein (IC). Split-inteins are only active when the two fragments are associated. Two protein purification systems using artificially split DnaB intein from *Synethocystis* sp (Ssp) have been developed. In one, the artificially split S1 DnaB intein consisting of an 11-aa N-intein (IN) and a 144-aa C-intein (IC). The target protein is fused to IC and tag-removal is achieved by the addition of the IN peptide. Since there is no N-extein present, wild-type catalytic residues are maintained. To achieve sufficient cleavage, a 40 to 1 molar ratio of IN to IC fused target protein is needed. Despite the small size of IN, peptide synthesis is costly, prohibiting the application of this system in large-scale processes. A similar affinity-based purification system using the same SspDnaB intein with a different split junction was also developed. In this system, mutations of the appropriate catalytic residue at the N- and C-terminal are employed to achieve C- and N-terminal cleavage, respectively. However, despite the relatively rapid reaction rate of wild-type Ssp-DnaB (FIG. 1), the mutant intein suffers reduced kinetics and requires extended incubation time (16 h) at room temperature to achieve sufficient C-terminal cleavage. The long incubation times limit the usefulness of this system.

Figure 2B:
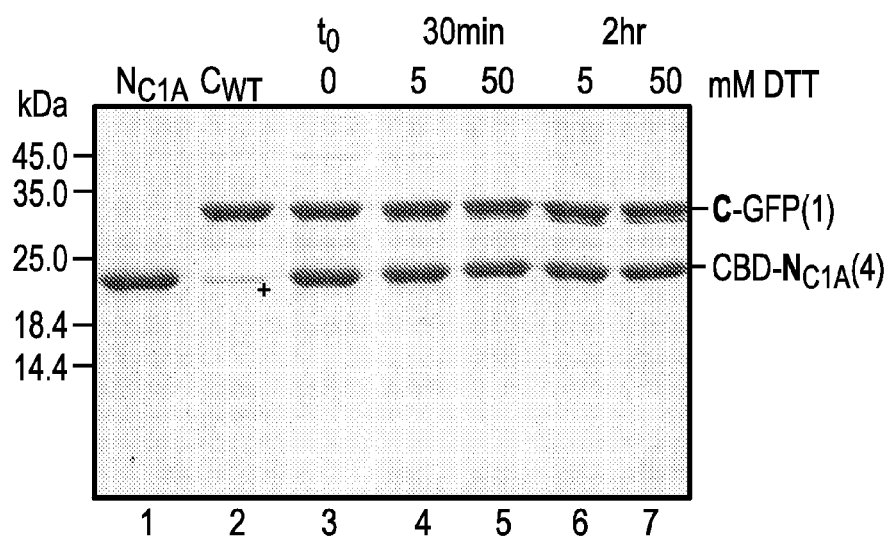

In certain embodiments, the present inventors recognize two additional limitations in the use of artificially split-inteins: they (1) are less active than their continuous counterparts due in part to a lower affinity between the split fragments, and (2) have a high tendency to form aggregates when expressed alone. The present inventors recognize that naturally split inteins such as DnaE from Ssp and Npu are highly active, soluble and exhibit very high affinity between the two split fragments. Neither of the two naturally split DnaE inteins have been used for protein purification. The highly exposed hydrophobic surface on IN of DnaE (102 and 123 aa for DnaE from Npu and Ssp, respectively) tends to interfere with the folding of N-extein, causing some fusion proteins to misfold and form insoluble aggregates and limiting the use of the N-fragment as a general purification tag. The present inventors recognize that despite its small size (36 aa for both Npu and Ssp) and no apparent interference with target protein solubility, the C-fragment of DnaE is also not suitable as a purification tag due to the tightly coupled C- and N-terminal cleavage reactions. In naturally split DnaE inteins, the C-terminal cleavage can only happen after the N-terminal cleavage, and mutation of the first Cys to Ala, which normally prevents N-terminal cleavage without interfering C-terminal cleavage activity, also abolishes the C-terminal cleavage (FIG. 2B).

For certain embodiments, the present inventors engineered NpuDnaE (termed Npu*) to undergo C-terminal cleavage without N-terminal cleavage by introducing a single mutation, Asp118, based on the sequence alignment to mini-MtuRecA intein. Npu* achieves ~80% C-terminal cleavage yield within 3 h of reaction at 22° C. In comparison, to achieve a similar extent of C-terminal cleavage, it takes ~16 h at 23° C. for the IMPACT system (New England Biolab) employing SceVma1 and SspDnaB intein (IMPACT Manual). Using Npu*, the present inventors further developed two protein purification methods and purified multiple target proteins to electrophoretic purity at high yields (up to 84 mg per liter of E. coli culture) within a short time (<4 hours), demonstrating the usefulness of these technologies and their potential for large-scale industrial protein purification.

The present inventors disclose the engineering of a DnaE intein able to catalyze rapid C-terminal cleavage in the absence of N-terminal cleavage. In certain embodiments, a single mutation in DnaE intein from *Nostoc punctiforme* PCC73102 (NpuDnaE), Asp118Gly, was introduced based on sequence alignment with a previously engineered C-terminal cleaving intein mini-MtuRecA. This mutation was able to suppress trans-splicing activity, retard N-terminal cleavage and significantly elevate C-terminal cleavage efficiency. Molecular modeling suggests that in NpuDnaE Asp118 forms a hydrogen bond with the penultimate Asn, preventing its spontaneous cyclization prior to N-terminal cleavage. Mutation of Asp118 to Gly abolishes this restriction leading to subsequent C-terminal cleavage in the absence of N-terminal cleavage. The Gly118 NpuDnaE mutant exhibits rapid thio-dependent (or thio-induced) C-terminal cleavage kinetics with 80% completion within 3 hours at room temperature. In various embodiments, the present inventors used this newly engineered intein to develop both column-free and chromatography-based protein purification methods utilizing the elastin-like-peptide and chitin-binding protein as removable purification tags, respectively. In certain embodiments, rapid target protein purification to electrophoretic purity at yields up to 84 mg per liter of E. coli culture.

Figure 4:
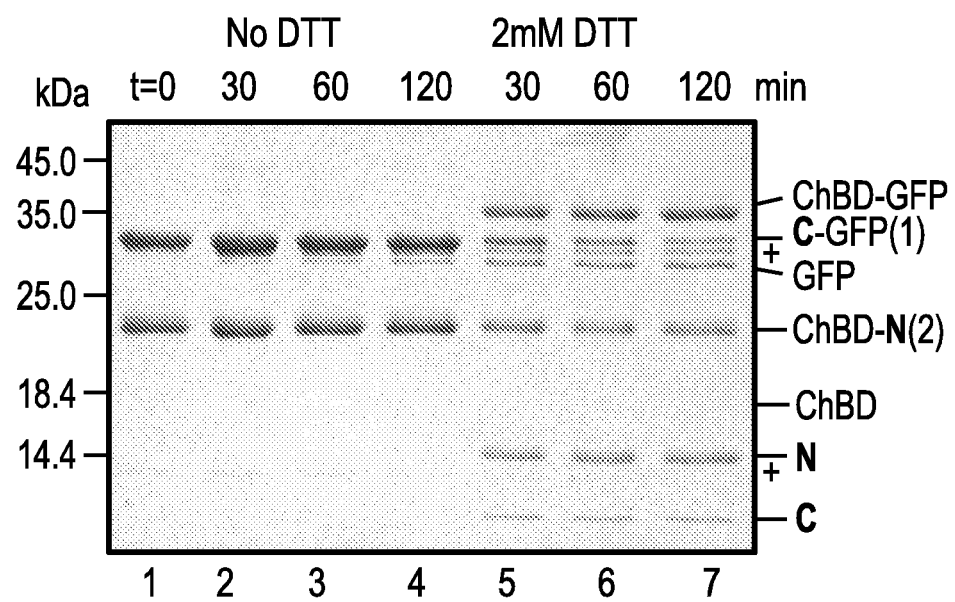
FIG. 4 demonstrates that the trans-splicing activity of wild type NpuDnaE intein is thio-dependent. Reaction between CBD-N (2) and C-GFP (1) at 22° C. in the absence or presence of 2 mM DTT visualized on SDS-gel (12% acrylamide). CBD-GFP is the trans-spliced product. GFP is the cleaved C-extein. C, N are the cleaved inteins. Trace amounts of the cleaved N-extein CBD are not visible from the SDS-gel due their low concentration, but are detectable by Western Blot (data not shown). "+" denotes unidentified bands.

In certain embodiments, and for the analysis of intein in vitro activity, various fusion proteins containing the IN or IC of NpuDnaE (N or C) were generated as illustrated in FIG. 3. For application as protein purification tag, it is important that the intein activity is regulated by an external stimulus. Although in theory, intein reaction does not require any thiol agents, there are a number of unpaired cysteine residues in NpuDnaE intein that could form intermolecular disulfide bonds and may prevent the intein reaction via redox trap formation. The present inventors determined whether the NpuDnaE activity is thio-dependent. Purified CBD-N (construct 2) was mixed with C-GFP (construct 1) at equimolar concentrations in the absence or presence of 2 mM DTT. The trans-spliced product CBD-GFP was only present in reaction containing DTT, confirming that split NpuDnaE intein is thio-dependent (FIG. 4). The trans-splicing reaction is near completion after 30 min. Trace amounts of cleaved N and C-extein are also visible, and are slightly more pronounced in reactions carried out at 50 mM DTT concentration (FIG. 2A). DTT can launch nucleophilic attack at the thio-ester bond of the linear or branched intermediate (FIG. 5A, step 1 and 2, respectively), resulting in N-terminal cleavage. The present inventor recognize that, on SspDnaE intein, the presence of 50 mM DTT was found to almost completely block protein trans-splicing and shunt the reaction to N-terminal cleavage and subsequent C-terminal cleavage. The limited amount of N-terminal cleavage seen in NpuDnaE intein, even at 50 mM DTT, may be due to the extremely rapid trans-splicing kinetics, given that the conversion of linear/branched intermediates to the trans-spliced product effectively competes with the nucleophilic attack by DTT.

In certain embodiments, mutant N with the first Cys replaced with Ala, CBD-NC1A (construct 4) showed no trans-splicing activity and negligible C-terminal cleavage activity even in 50 mM DTT (FIG. 2B, consistent with previous findings that the C-terminal cleavage reaction is tightly coupled to N-terminal cleavage in DnaE inteins. The present inventors recognize that this unique property prevents the use of the wild-type DnaE intein in C-terminal protein purification applications.

Figure 5A:
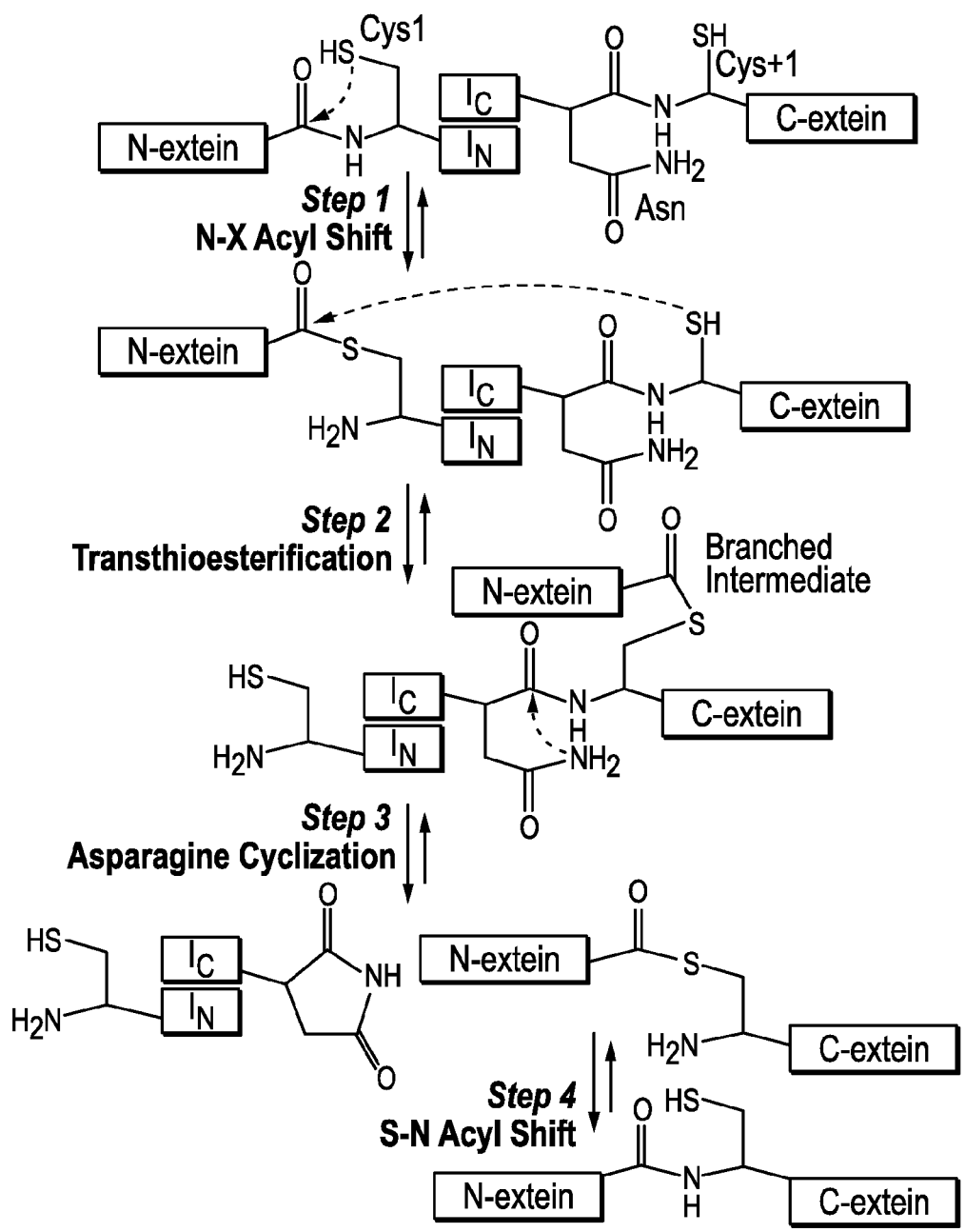
FIGS. 5A, 5B, and 5C depict the mechanism.

Rational design of C-terminal cleaving Npu DnaE: With a few exceptions, most intein splicing reactions comprise four highly coordinated nucleophilic replacements (FIG. 5A). The first step involves an N—X acyl shift (X: C or S) in which the first residue of the intein, a cysteine (Cys 1) or serine, attacks the proceeding peptide carbonyl, forming a linear (thio) ester. In the second step, the first residue of the C-extein, a cystein (Cys+1), serine, or threonine, attacks the (thio)ester carbonyl, cleaving the N-extein and forming a branched intermediate with two N-termini, one belonging to the intein and the other to the N-extein. In this state, the exteins are joined together but are still attached to the intein C-terminal. This branched intermediate is then cleaved from the intein by a transamidation reaction involving the last asparagine residue of the intein (step 3). In the final step, the free exteins undergo a spontaneous X—N acyl shift, which reverts the (thio)ester to a peptide bond and forms the spliced protein product.

Figure 5B:
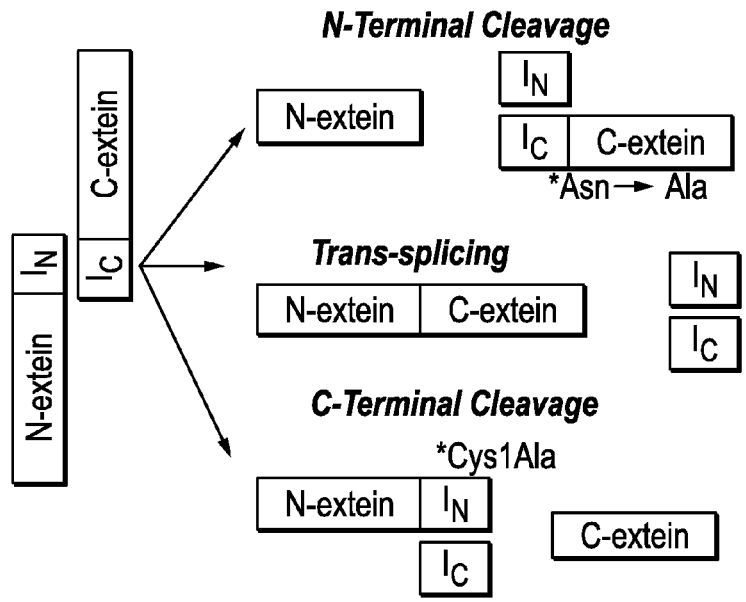
Figure 5C:
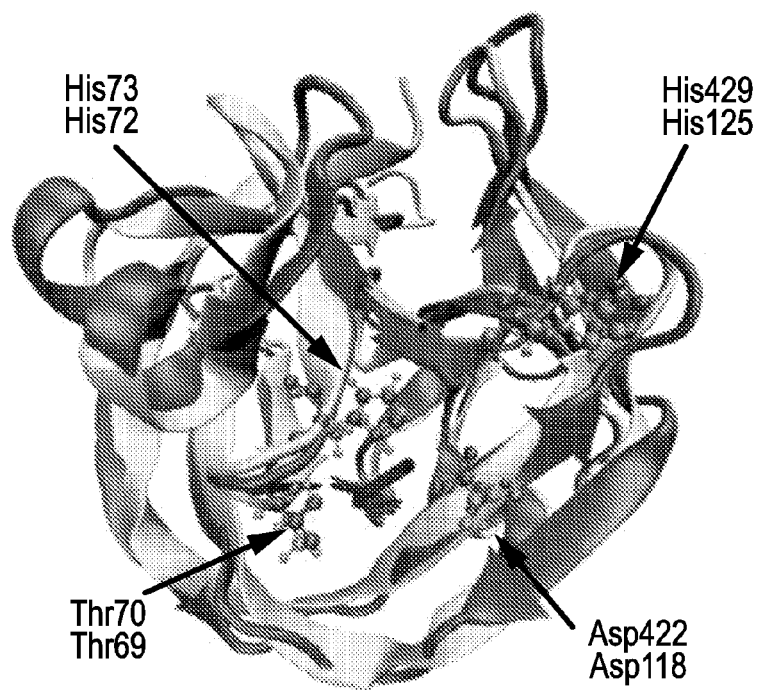

In most inteins, the reactions at N- and C-termini are independent, such that the mutation of a catalytic residue that abolishes the reaction at one terminus results in a cleavage reaction at the other terminus. (FIGS. 1, and 5B) However, due to the tight coupling of N- and C-terminal cleavage reaction, the conventional method cannot be used to engineer a C-terminal cleaving DnaE intein. A C-terminal cleaving intein, mini-MtuRecA, was engineered using directed evolution. A single mutation, D422G, was found to be responsible for the elevated C-terminal cleavage activity and suppressed N-terminal cleavage. Alignment of NpuDnaE and mini-MtuRecA inteins revealed high homology on the sequence level (FIG. 6) and even higher homology on the structural level (FIG. 5C). Most of the catalytic residues, including Asp422 (Asp118 in NpuDnaE) are conserved between NpuDnaE and mini-MtuRecA intein (FIG. 6). The present inventors recognized that mutation D118G may confer C-terminal cleavage activity to the NpuDnaE intein.

Figure 8:
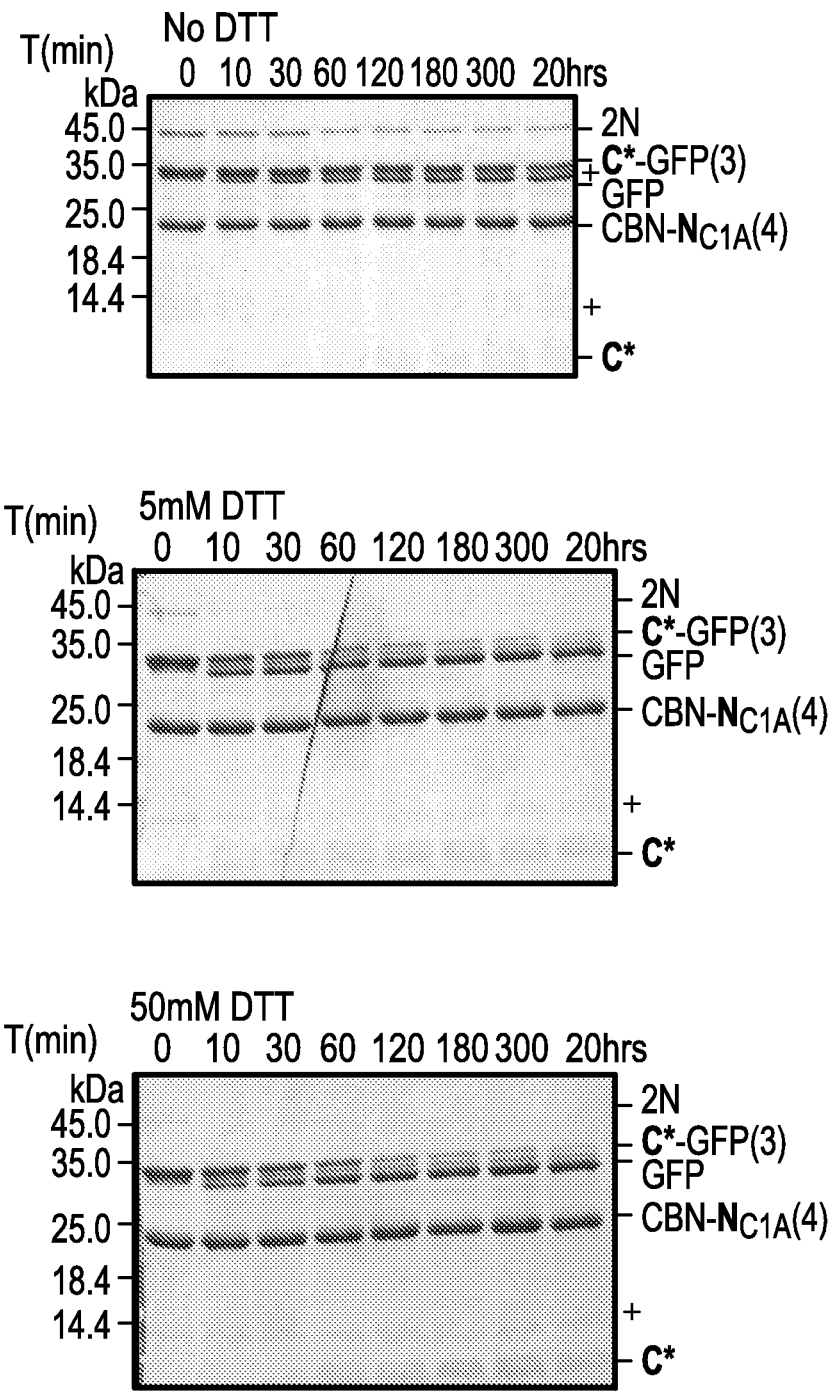
FIG. 8 shows catalytic activity of C*-GFP with CBD-NC1A. Reaction of C*-GFP (3) with CBD-NpuNC1A (4) at 22° C. in the absence or presence of DTT. GFP and NpuC* are the cleaved C-extein and C-intein, respectively. "+" denotes impurities.

Activity of Npu DnaE intein with Asp118Gly mutation: To test the effect of the D118G mutation, the amino acid substitution was introduced into C-GFP via site directed mutagenesis to form C*-GFP (construct 3). Similar to wild type NpuDnaE, the activity of mutant Npu* is also thio-dependent. The D118G mutation completely abolished the trans-splicing reaction and induced rapid C-terminal cleavage under reducing conditions (FIG. 7A). No spontaneous C-terminal cleavage was observed with C*-GFP incubated alone or with DTT at room temperature even after 20 h, confirming the C-terminal cleavage activity is N dependent. Little free N-extein was observed when the reaction was carried out at low DTT concentration, and only very limited amount of free N-extein was observed in reaction at high DTT concentration (50 mM), suggesting that that D118G mutation essentially abolished the first N—X acyl shift and induced C-terminal cleavage reaction independent of N-terminal cleavage. To further confirm that Npu* is able to undergo C-terminal cleavage in the absence of N-terminal cleavage, the present inventors carried out the reaction in the presence of trialkylphosphine (tris(2-carboxyethyl)phosphine, TCEP) that is capable of disrupting disulfide but not thio-ester bonds. TCEP also induced C-terminal cleavage reaction with no N-terminal cleavage at all (FIG. 7B), indicating that Npu* has uncoupled N- and C-terminal cleavage activity. The present inventors also determined the activity of C*-GFP when mixed with CBD-NC1A (construct 4). A similar rate of C-terminal cleavage was observed under reducing conditions. However, rapid C-terminal cleavage was also observed even in the absence of DTT, making it unsuitable for use as a controllable protein purification tag (FIG. 8). It is possible that, due to very close proximity, Cys1 and Cys+1 form disulfide bond immediately upon association of the two intein fragments, preventing further intein reaction and allowing control of the onset of C-terminal cleavage by reducing agents. The present inventors also determined the C-terminal cleavage kinetics of Npu* at different temperatures (FIG. 7C). The highest cleavage rate was obtained at 37° C. where ~80% cleavage was achieved in just 1 hour. To achieve the same 80% cleavage, 3 and 4.5 hours were needed for samples incubated at room temperature (22° C.) and 16° C., respectively. Over 85% C-terminal cleavage was obtained at 4° C. after 20 h. This cleavage rate is significantly higher than that of SspDnaB and SceVma1 inteins used currently in the IMPACT system (New England Biolab), which require about 16 h incubation at 23° C. to achieve a similar cleavage efficiency. It's possible that a higher cleavage rate may be achieved when an excess of N is present. Taken together, these results demonstrate the usefulness of Npu* as a self-cleaving tag for protein purification.

Abbreviations: ELP, Elastin-Like-Peptide; CBD chitin binding domain; POI, protein of interest; Mtu, *Mycobacterium tuberculosis*; Npu, *Nostoc punctiforme*; IN/IC, split intein N-/C-fragment; N/C, NpuDnaE N-/C-fragment; IPTG, Isopropyl β-D-1-thiogalactopyranoside; SDS, sodium dodecyl sulfate.

To obtain the C-terminal cleavage kinetics and efficiency used in SIRP, the present inventors re-positioned the protein purification tag at the intein split junction (C-terminus of the intein N-fragment), and the target protein was fused to the C-terminus of the C-fragment. This system exhibits extraordinarily rapid thio-induced C-terminal cleavage with about 50% completion within 30 seconds at both 22° C. and 6° C. This is the fastest C-terminal cleavage activity reported to date for inteins. Although the reaction kinetics appears to slow down after the first minute, >85% cleavage completion is achieved within 30 minutes at 22° C., or within 3 h at 6° C. The ultra-rapid cleavage kinetics is made possible by the positioning of the purification tag at the intein split junction, thus avoiding potential steric hindrance of the critical interaction between the N- and C-extein. The C-terminal cleavage efficiency of the engineered split intein was not affected by the identity of the first residue of the C-extein (proline was found to be an exception), enabling SIRP to completely remove the purification tag and purify proteins with the native N termini. The C-terminal cleavage reaction can be effectively inhibited by divalent $Zn^{2+}$ under non-reducing conditions. Importantly, the association of the intein N- and C-fragments is reversible, enabling the column-bound intein N-fragment bait protein to be regenerated for multiple usages and further reducing the cost of protein purification. SIRP technology should provide a useful tool for the purification of tagless proteins and peptides.

Figure 9A:
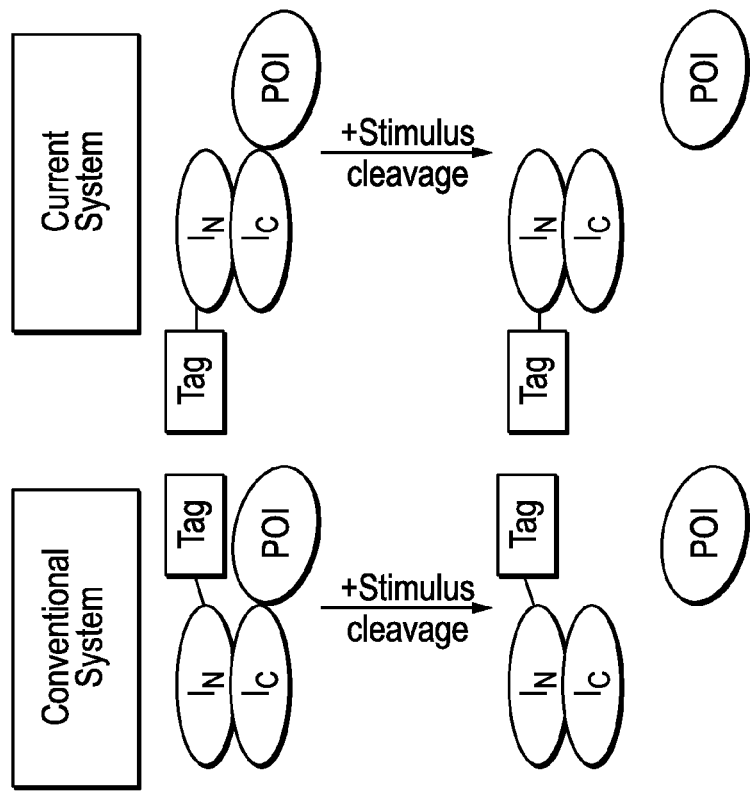
FIGS. 9A and 9B schematics depict an engineered intein pair.
Figure 9B:
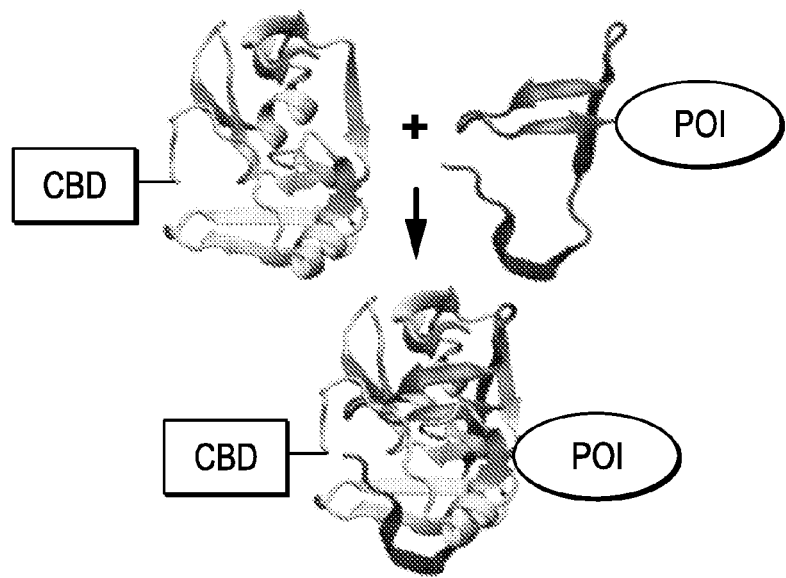

The naturally split DnaE from *Nostoc punctiforme* (NpuDnaE) has very high trans-splicing activity and, since the constituent fragments are expressed in separate hosts, premature in vivo intein cleavage does not occur. The present inventors have engineered NpuDnaE to perform thio-induced C-terminal cleavage by introducing a point mutation, Asp118Gly, into the C-intein fragment (C) to create mutant C*. In certain embodiment, the first residue of the N-intein fragment (N) was mutated to Ala (NC1A) to completely abolish any N-terminal cleavage activity and an affinity tag, chitin binding domain (CBD), was appended to the C-terminus of NC1A to create construct NC1A-CBD (construct 12). This construct contains a single Met as the N-extein and stands in contrast to conventional intein systems used for protein purification in which the affinity tag serves as the N-extein and can interfere with cleavage activity via steric interference with the C-extein (FIG. 9A). The protein of interest (POI) was attached to the C-terminus of C*.

The present inventors generated various fusion proteins containing the engineered intein pairs as listed in FIG. 3. To determine the C-terminal cleavage kinetics, C*-PTDH (Construct 6), comprising C* fused to a globular protein phosphite dehydrogenase (PTDH), was mixed with NC1A-CBD (Construct 12) at 1:1 molar ratio in the presence of 50 mM DTT. ~50% of PTDH was cleaved from C*-PTDH within 30 seconds at both 22° C. and 6° C. (FIGS. 10, A and B). Since 30 seconds is the earliest time point that could be measure accurately, it is possible that even shorter time is needed to achieve this much cleavage. In comparison, the fastest reported C-terminal-cleaving intein, gp41-1C1A, has a $t_{1/2}$ of 5 min at 37° C. Although the reaction kinetics slowed down after the first minute, over 85% C-terminal cleavage is achieved within 30 min and 3 hour at 22° C. and 6° C., respectively (FIG. 10D). This rapid cleavage rate is likely due to 1) the high activity of wild-type NpuDnaE, 2) mutation Asp118Gly in the intein C-fragment, and 3) elimination of N-extein that could potentially interfere with POI. Interestingly, unlike CBD-NC1A (construct 4) that is unable to cleave the wild-type C, NC1A-CBD can also induce significant C-terminal cleavage of wild-type C upon association, with ~30% cleavage in 3 h at 22° C. (FIG. 10D, 2B). These data provide further evidence that the tight restriction of C-terminal cleavage until N-terminal cleavage seen in NpuDnaE intein is at least in part due to the presence of the N-extein, as also observed with the SspDnaE intein.

Figure 11A:
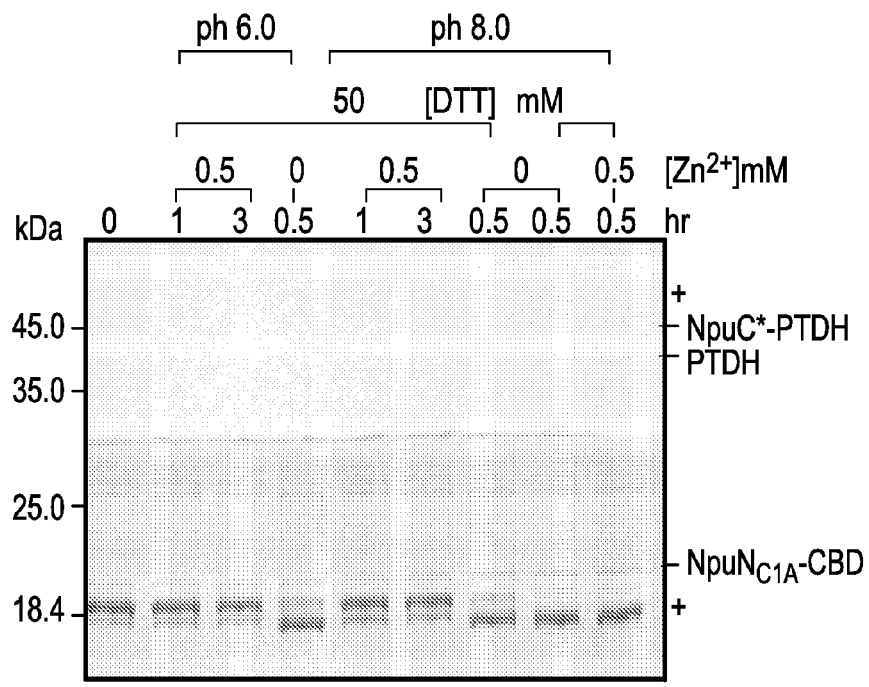
FIGS. 11A and 11B depict C-terminal cleavage kinetics under different conditions.
Figure 11B:
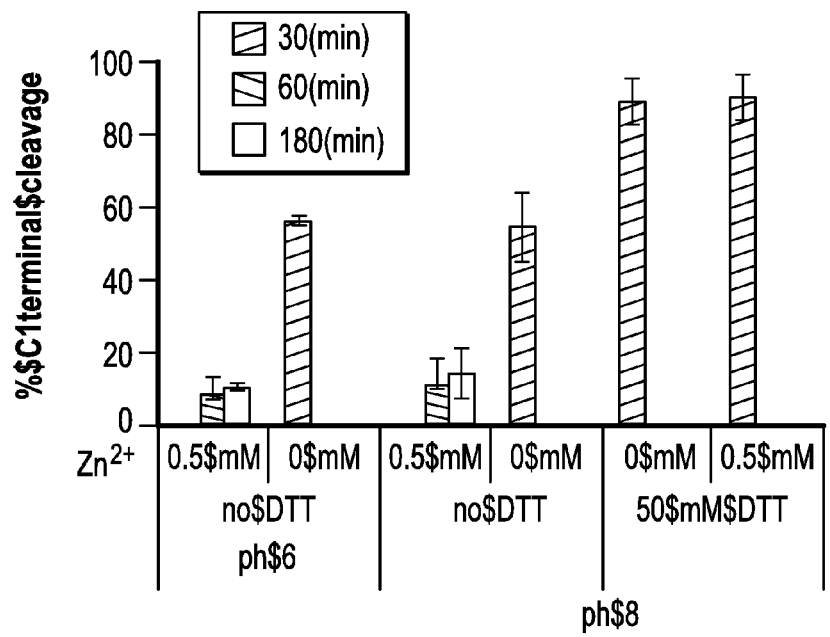

NC1A-CBD also induced rapid C-terminal cleavage of C*-PTDH under non-reducing conditions, albeit at a much slower rate than under reducing conditions (FIG. 11B, 0 mM Zn2+). Over 50% C*-PTDH is cleaved within 30 minutes at both neutral and acidic pH even in the absence of DTT. This basal level cleavage is likely due to the absence of Cys1, which could form a disulfide bond with Cys+1 and inhibit the intein reaction. The present inventors tested the ability of $Zn^{2+}$ to inhibit the C-terminal cleavage reaction of the engineered NpuDnaE construct. As shown in FIG. 11A, $ZnCl_2$ (0.5 mM) can effectively inhibit the C-terminal cleavage reaction under non-reducing conditions but has little inhibitory effect in the presence of DTT. The inhibition is stronger at pH 6 with only ~10% intein cleavage after 3 h incubation at 22° C. These results demonstrate that $Zn^{2+}$ and DTT can be used as effective switches to turn off and on, respectively, C-terminal cleavage. Higher $Zn^{2+}$ concentration can more efficiently inhibit the C-terminal cleavage reaction and helps preventing loss of product during extended washing steps. The present inventors recognize that, $Zn^{2+}$ ions at a concentration ≥1 mM can cause precipitation of some cellular proteins and thus should not be used directly in the cell lysate. According to the crystal structure of SspDnaE, $Zn^{2+}$ is coordinated by Asp140, His48 (equivalent of Asp118, His48 in NpuDnaE) and Cys+116. However, Asp118 is mutated to Gly in C* to confer C-terminal cleavage activity in the absence of N-terminal cleavage. Thus, the inventors recognize that there is another site(s) on NpuDnaE for $Zn^{2+}$ binding. The inventors also recognize that other ions/molecules constitute cleavage inhibitors and could be able to inhibit the C-terminal cleavage more effectively than $Zn^{2+}$ under non-reducing conditions.

Figure 12:
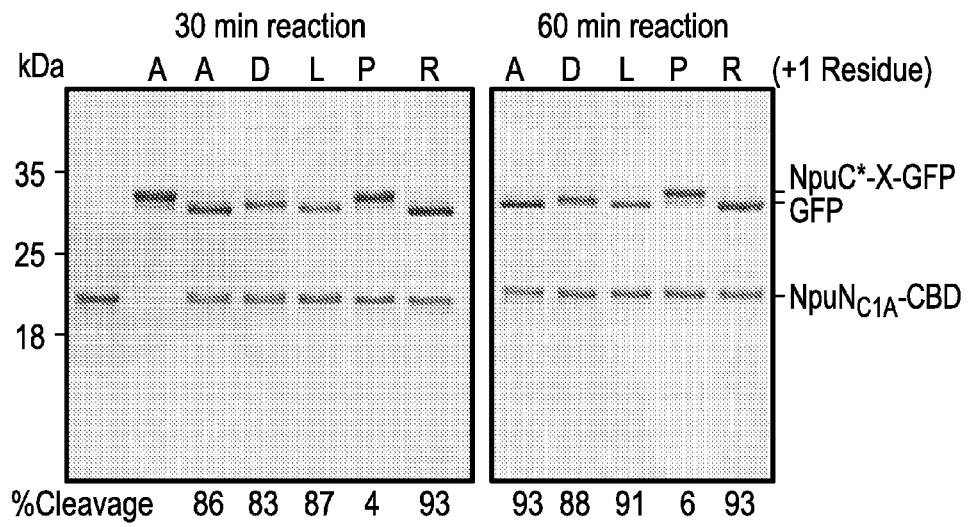
FIG. 12 shows the effects of +1 residue on C-terminal cleavage. SDS gel of reactions of NC1A-CBD and C*-X-GFP at pH8 and 22° C. The calculated percentage C-terminal cleavage of C*-X-GFP is shown under the respective lane. The capital letters on top represent the amino acid substitution at the +1 position. The standard deviations for all the cleavage reaction from 2 independent experiments are less than 7%.

In certain embodiments, it is desirable to completely remove all non-native amino acids from the target protein. For intein trans-splicing reactions, a cysteine is required at the +1 position to complete the transesterification and S/O—N acyl shift reactions. But Cys+1 is not needed for the asparagine cyclization reaction responsible for C-terminal cleavage. The present inventors designed various C*-X-GFP fusion proteins (FIG. 3, constructs 14-18) in which the first residue (X) of the C-extein was replaced with 5 different amino acids, Ala, Leu, Asp, Arg and Pro, representing amino acids with small, large, hydrophobic, polar, positively and negatively charged side chains. Except for Pro+1, all other substitutions yielded complete C-terminal cleavage after 30 minutes at room temperature (FIG. 12), a cleavage profile comparable to that observed with the original C* construct which contains a Cys at the +1 position (FIG. 10).

Figure 13:
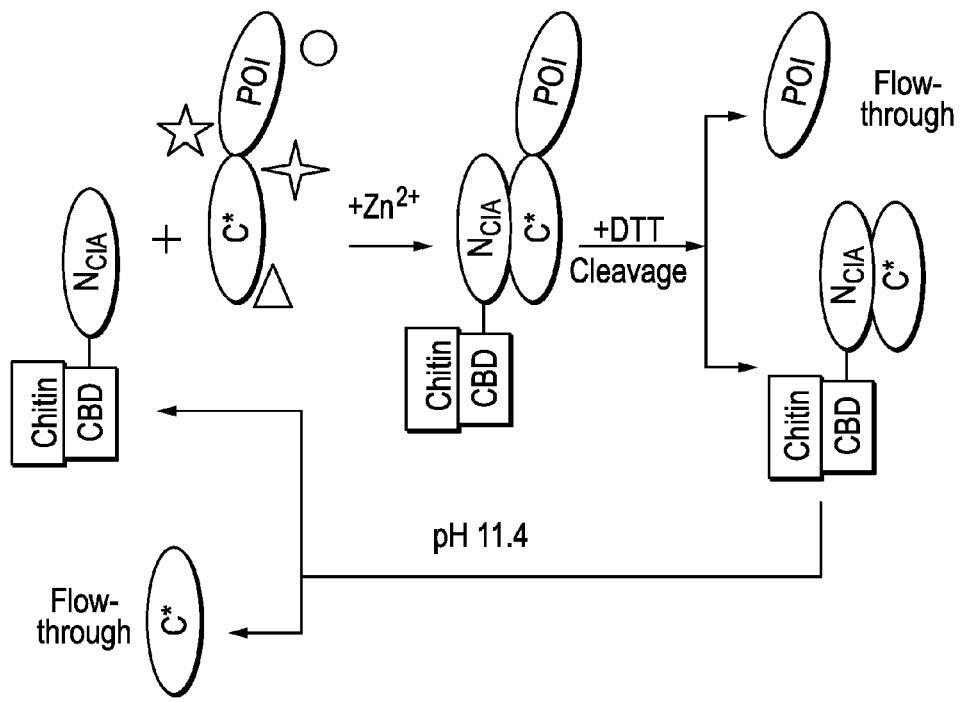
FIG. 13 depicts protein purification using the developed method referred to as SIRP (Split intein mediated ultra-rapid purification of tagless proteins).
Figure 14A:
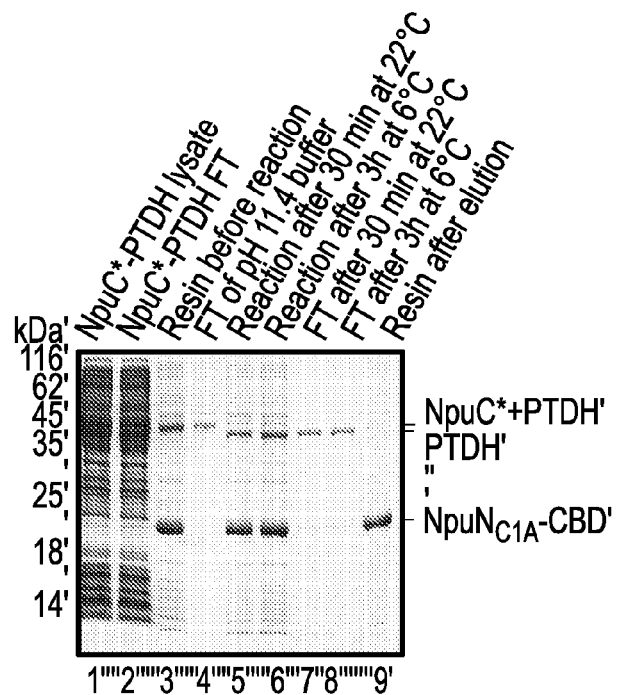
FIGS. 14A and 14B depict purification of PTDH (FIG. 14A) and GFP (FIG. 14B) using NC1A-CBD-chitin resin under SIRP method. SDS-PAGE analysis of the purification of PTDH (left) and GFP (right). Lane 1, soluble fractions of lysate containing C*-PTDH/GFP; lane 2, flow through of soluble lysates; lane 3, chitin resin after loading lysate and washing with buffer containing 0.5 mM $ZnCl_2$; lane 4, elution of C*-PTDH/GFP in pH 11.4 buffer; lane 5, chitin resin in cleavage buffer incubated at 22° C. for 30 min; lane 6, chitin resin in cleavage buffer incubated at 6° C. for 3 h; lane 7, flow-through after incubation in cleavage buffer at 22° C. for 30 min; lane 8, flow-through after incubation at 6° C. for 3 h; lane 9, chitin resin after elution of target protein.
Figure 14B:
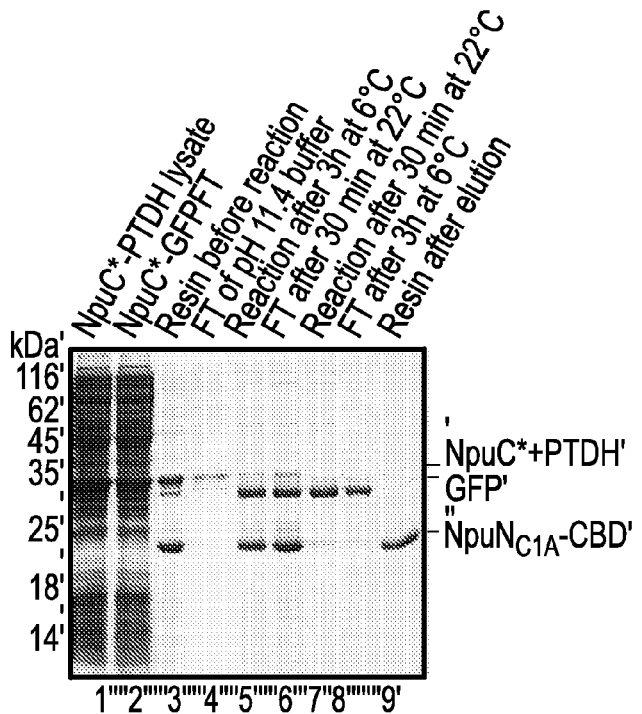

Certain embodiments comprise chitin binding domain (CBD), and in order to demonstrate the utility of the engineered intein pairs, the present inventors designed a protein purification approach based on the chitin binding domain (CBD) (FIG. 13) and purified two proteins via chitin affinity chromatography (FIGS. 14A and 14B). As much as 14 mg and 18 mg of highly pure PTDH and GFP were obtained per mL of chitin resin, respectively. The molar ratios of bound C*-PTDH and C*-GFP to NC1A-CBD, as determined from SDS-PAGE analysis, are 0.35 and 0.92, respectively. The difference in binding capacity is likely due to the larger size of PTDH, which is a dimer, compared to the globular single-domain GFP. The intein C-terminal cleavage efficiencies for both proteins when immobilized on the affinity resin are comparable to that observed in solution with >80% cleavage in 30 min at 22° C. and in 3 h at 6° C. (FIG. 14, lane 5, 6). A small amount of cleaved GFP is present in the C*-GFP sample (FIG. 14B, lane 3). This is mainly due to the proteolytic cleavage during cell lysis, and non-specific interaction of GFP with chitin resin. The association of C* and NC1A is reversible as pH 11.4 buffer selectively elutes uncleaved C*-PTDH/GFP from chitin-bound NC1A-CBD (FIG. 14, lane 4), demonstrating that the high affinity between C* and NC1A is largely dictated by electrostatic interactions.

Figure 15:
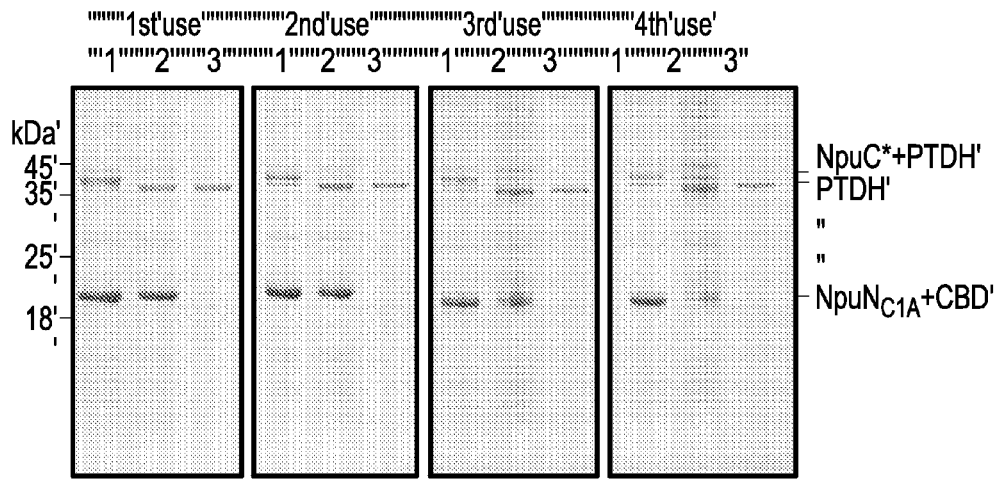
FIG. 15 shows that chitin-bound NC1A-CBD can be regenerated after purification. SDS-gel of samples collected during the purification of PTDH using regenerated column, lane 1, chitin resin before cleavage; lane 2, chitin resin in cleavage buffer incubated at 22° C. for 30 min; lane 3, flow through containing purified PTDH. The cleaved C* is 4 kDa and is not visible from the gel.

In certain embodiments, the fusion proteins comprising NC1A are recycled. To demonstrate the recyclability of chitin-bound NC1A-CBD, the present inventors repeated the purification of PTDH using the same chitin column 4 times (FIG. 15). After elution of cleaved PTDH and before the addition of fresh lysate containing C*-PTDH, the chitin resin was thoroughly washed with pH 11.4 buffer to remove cleaved C* from NC1A-CBD on the column. The yields of purified PTDH are comparable for all 4 cycles, confirming the ability of the NC1A-CBD-chitin affinity matrix to be regenerated for multiple usage cycles. It appears that cleaved C* may dissociate more readily from NC1A-CBD in pH 11.4 buffer than the full-length C*-PTDH.

The present inventors recognize that the use of DTT as a cleavage inducer for protein elution is not desirable in certain applications, e.g., for proteins that rely on surface-exposed disulfide bonds for their tertiary and quaternary structure. The present inventors recognize that EDTA can be used as an inducer of C-terminal cleavage, given that it can chelate the $Zn^{2+}$ ions that suppress basal cleavage and release the POI (FIG. 11B, 0 mM DTT and $Zn^2$).

Example 1

Figure 16:
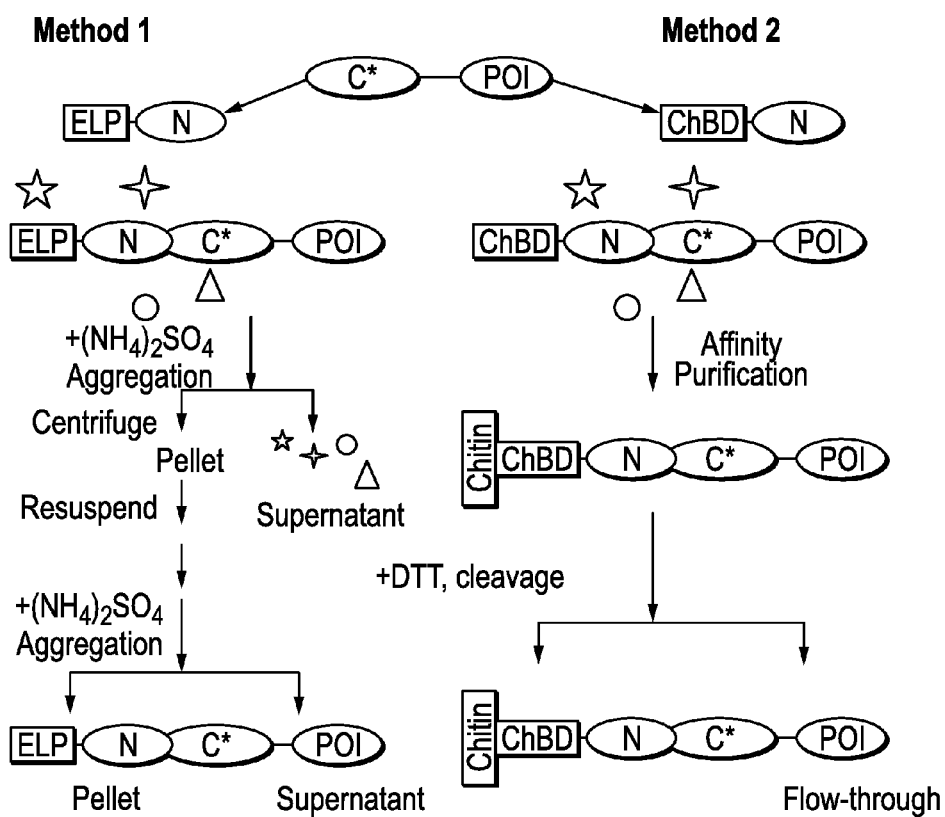
FIG. 16 provides a schematic representation of two embodiments of protein purification methods. Method 1: column-free approach. Method 2: chromatography-based approach. The symbols represent E. coli cellular proteins present in the lysate.

Protein purification via reversible precipitation and chitin resin: To demonstrate the utility of Npu* in protein purification, the present inventors developed various embodiments of protein purification methods (FIG. 16). Certain embodiments comprise methods that combine the reversible precipitation of the elastin-like-peptide (ELP) with the controllable C-terminal cleavage of Npu* (FIG. 16, Method 1). N was joined to the C-terminus of the elastin-like polypeptide (ELP) via a flexible linker ELP-N (construct 5), and mutant C* was fused to the N-terminus of various sample target proteins C*-POI (construct 3, 6-10). Under non-reducing conditions, N and C* non-covalently interact with each other without cleavage, physically associating the POI with the ELP. Addition of ammonium sulfate triggers phase separation of the ELP, resulting in the aggregation of the ELP and the associated POI. After removal of cellular proteins in the supernatant, this precipitant is then solubilized in low-salt reducing buffer, reversing the phase transition and inducing C-terminal cleavage of the intein. Upon cleavage, the POI is released from the ELP-intein complex, which is selectively removed by a second round of ammonium sulfate precipitation and centrifugation, giving rise to POI of high purity in solution.

Figure 17A:
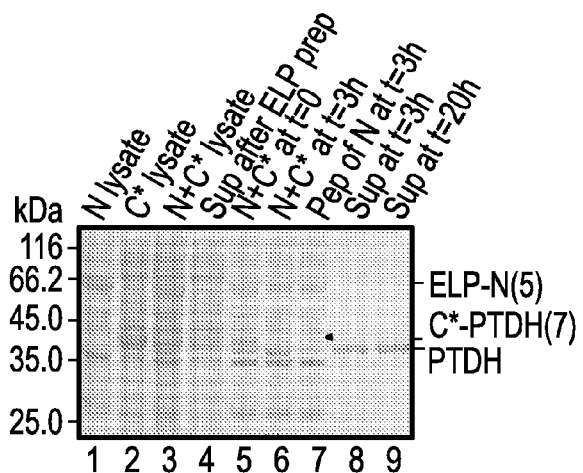
FIGS. 17A, 17B, and 17C depict purification of PTDH, DsRed and GFP using engineered Npu* intein.
Figure 17B:
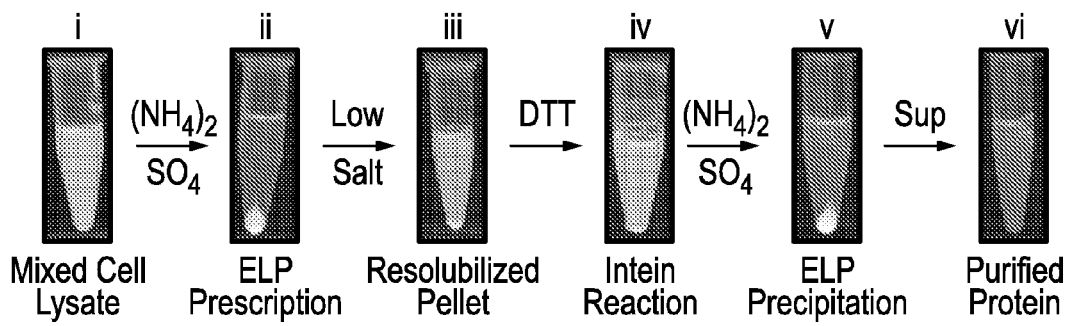

Sample purification of a globular protein phosphite dehydrogenase (PTDH) is shown in FIG. 17A. The yields were 49.8 and 59.3 mg of purified PTDH per liter of E. coli culture with intein self-cleavage reaction times of 3 h and 20 h, respectively, at 22° C. The purification of 5 additional proteins of various sizes and multimeric states (constructs 3, 7-10) are shown in FIGS. 18A-18E. The purification process for DsRed (construct 7) can be conveniently monitored by visual inspection (FIG. 17B). The target protein purification yields and the percentage recovery from soluble lysate are summarized in FIG. 19. High purities were obtained for all the proteins tested. Not surprisingly, the ELP pull-down efficiency and intein cleavage kinetics are influenced by the target protein (FIG. 20). Both monomeric and multimeric proteins can be efficiently purified by this method. In most cases, the intein self-cleavage reaction is essentially complete in 4 hours, keeping the time to complete the entire procedure on par with conventional chromatographic protein purification processes.

Example 2

Figure 17C:
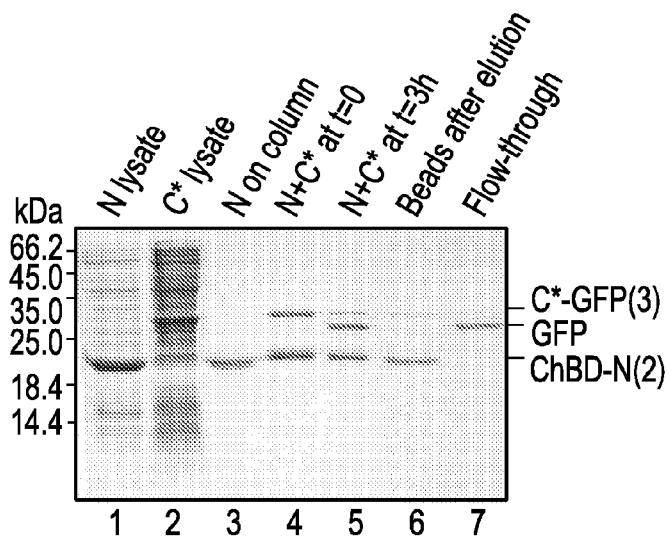
Figures 18A, 18B:
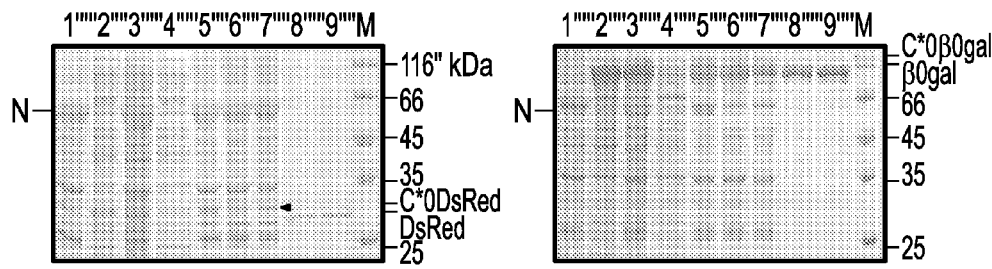
FIGS. 18A-18E show additional sample purifications of recombinant proteins using reversible precipitation of ELP and self-cleaving C*. Lane 1, pre-purified ELP-N; lane 2, soluble lysate containing C*-POI; lane 3, mixture of samples from lanes 1 and 2; lane 4, supernatant after the precipitation of the ELP complex; lane 5 and 6, ELP-N and C*-POI mixture at the beginning and after 3 h of intein reaction, respectively; lanes 7, ELP precipitant after 3 h intein cleavage reaction; lanes 8 and 9, supernatant containing purified POI after ammonium sulfate precipitation with 3 and 20 h intein cleavage reaction times, respectively. An equivalent amount of protein was loaded into each lane. Black arrow indicates the uncleaved C*-POI (A) DsRed, (B) β-galactosidase (β-gal), (C) chloramphenical acetyl transferase (CAT), (D) maltose binding protein (MBP), (E) green fluorescent protein (GFP).
Figures 18C, 18D:
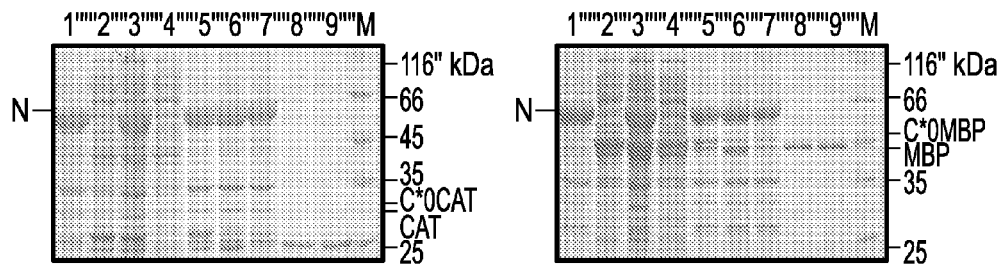
Figure 18E:
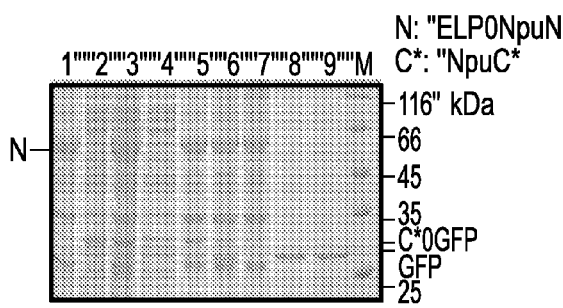

Since chromatography-based methods remain the mainstay for recombinant protein purification, the present inventors also developed embodiments employing affinity based purification methods to further expand the utility of the engineered intein. In this method, the ELP is replaced with the chitin binding domain (CBD) and purification is achieved through binding to the chitin beads (FIG. 16, method 2). Sample purification of GFP is shown in FIG. 17C. The yield of purified GFP was ~2 mg from a 100 µl chitin column. The binding capacity of chitin beads appears to be much higher than that reported for maltose binding protein (0.2 mg/100 µL chitin beads, New England Biolabs website). The exact reason is unknown but may due in part to the much smaller size of N compared to the maltose binding protein.

Certain embodiments comprise an engineered a split NpuDnaE intein that is able to undergo rapid C-terminal cleavage reaction without N-terminal cleavage. Split NpuDnaE intein is one of the most active inteins identified to date (FIG. 1). However, despite the rapid reaction kinetics and high solubility of NpuDnaE, the dependence of C-terminal asparagine cyclization on the acyl shift at the N-terminus prevents the use of DnaE intein in many applications such as protein purification. The multi-step catalytic pathway leading to intein trans-splicing is highly coordinated, but the precise mechanism involved in this series of reactions remains unclear. Intein N-/C-terminal cleavage can result from either an increase in the rate of cleavage at that splice junction or a decrease in the reaction rate of another step. The present inventors recognize that a single mutation in mini-MtuRecA intein, D422G, that is able to abolish the trans-splicing activity and significantly elevate the C-terminal cleavage activity. Asp422 lies in the conserved Block F region (also termed the C2 motif) within the intein active site and is 75% conserved among all inteins from different species, including split NpuDnaE and SspDnaE inteins (FIG. 6). This Block F aspartate has previously been shown to be essential for both the first and second steps of intein reaction (FIG. 5A). The crystal structures of multiple inteins, including the SspDnaE, show that this aspartate forms hydrogen bond with the oxyanion of the N-terminal Cys1, likely positioning this residue for the first step N—X acyl shift. In addition, quantum mechanics simulations and structural studies from other inteins suggest that this aspartate also deprotonates the thiol group of Cys+1, enabling it to launch nucleophilic attack to form branched intermediate. Mutation of this Asp422 in mini-MtuRecA significantly retards the N-terminal cleavage reaction and the formation of branched intermediate. NMR structure of NpuDnaE intein showed that Asp118 (equivalent of Asp422 in mini-MtuRecA) is within hydrogen bond distance with the oxyanion of the first residue, although the NMR structure contains an Ala at this position. Npu* with the corresponding aspartate changed to Gly exhibited very limited N-terminal cleavage even at 50 mM DTT (FIG. 7A), suggesting that this mutation likely also blocks the first step N—X acyl shift and formation of branched intermediate.

Figure 22:
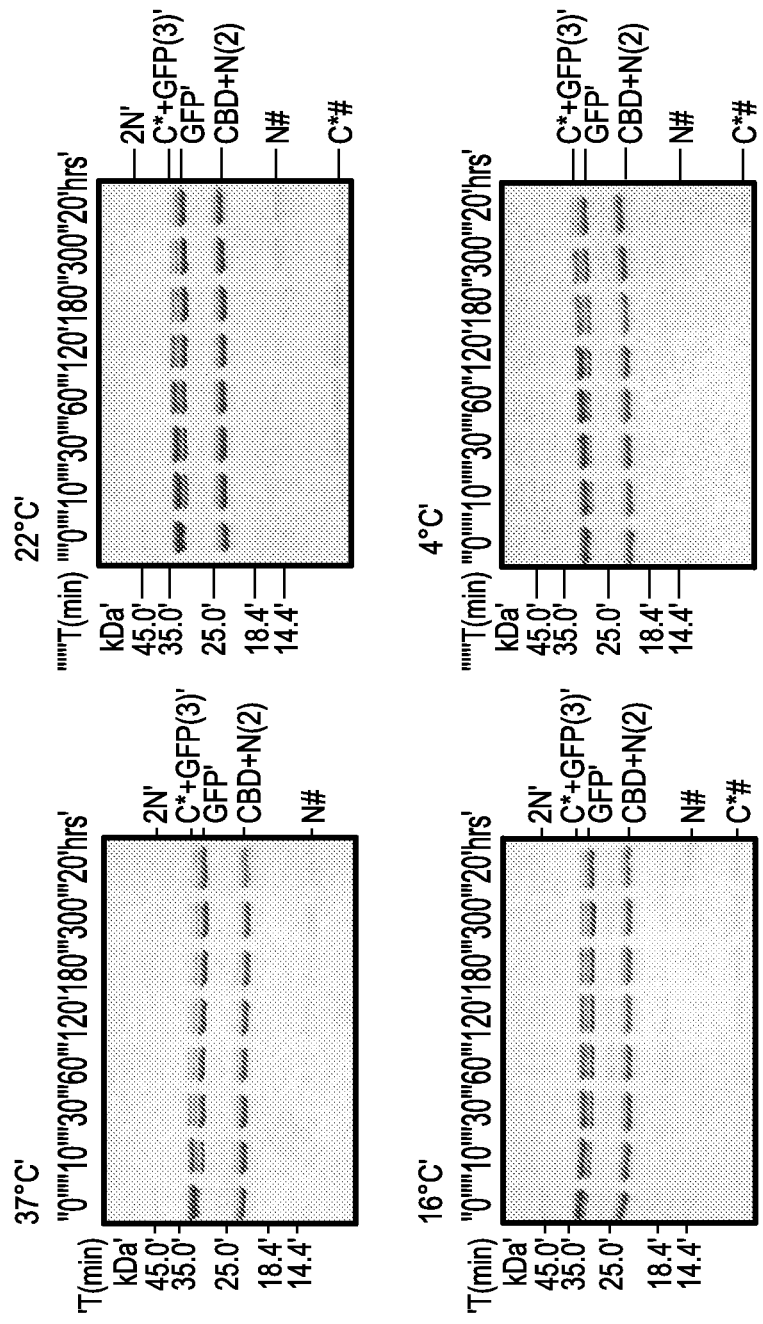
FIG. 22 shows reaction of C*-GFP (3) with CBD-NpuN (1) was incubated in 5 mM DTT at different temperatures. The reaction was stopped by mixing samples with SDS-sample buffer and boiled for 5 minutes.

In mini-MtuRecA intein, the C- and N-terminal cleavage reactions are not coupled, thus retardation of the first and second steps of intein reaction can account for the elevated C-terminal cleavage product. However, in DnaE intein, the C- and N-terminal cleavage reactions are highly coupled. Inhibition of the first two steps do not lead to elevated C-terminal cleavage product directly, as mutant DnaE inteins with CA exhibited little to no C-terminal cleavage. To understand how D118G induces C-terminal cleavage in NpuDnaE intein, the present inventors compared the solution structure of NpuDnaE with the crystal structure of its closest homolog SspDnaE. In SspDnaE intein, C-terminal asparagine cyclization is mediated by a charge relay process involving His147, Asn159, Arg73 and a water molecule near the C-terminal splicing junction (FIG. 21A). The water molecule is within hydrogen bonding distance to the Nδ atoms of Asn159 and His147 and the backbone nitrogen of Leu143, and transfers a proton from Asn159 to His147 (FIG. 21A). The deprotonated Asn159 Nδ initiates nucleophilic attack to its carbonyl carbon atom, resulting in breakage of the C-terminal intein-extein bond. The same mechanism is involved in the asparagine cyclization in SspDnaB and mini-MtuRecA, which contain a water molecule in the similar position. The NMR structure of NpuDnaE shows that Asp118 can form a hydrogen bond with the Nδ of Asn137, rendering it unfavorable for charge relay and thus inhibiting C-terminal cleavage (FIG. 21B). Formation of a branched intermediate, which was shown to require protonation of Asp118 by the hydrogen from the thiol group in Cys+1 in some studies, may break the H-bond interaction of Asn137 with Asp118, allowing Asn137 to participate in charge relay leading to C-terminal cleavage. Formation of a branched intermediate results in a subtle change of the intein structure that accelerates the C-terminal asparagine cyclization reaction. Mutation of Asp118 to the much smaller Gly eliminates the H-bond interaction and enables Asn137 to freely participate in charge relay without the need of structural changes, leading to decoupled C-terminal cleavage. Thus, in addition to inhibiting the first two steps of intein reaction, D118G may also accelerate the asparagine cyclization in Npu*, leading to rapid C-terminal cleavage. FIG. 22 shows reaction of C*-GFP (3) with CBD-NpuN (1) was incubated in 5 mM DTT at different temperatures. The reaction was stopped by mixing samples with SDS-sample buffer and boiled for 5 minutes.

The cleavage kinetics of Npu* is slightly slower than that of the wild-type intein trans-splicing reaction (FIG. 1). This may be due to the imperfect positioning of Asn137 in the absence of Asp118 side chain. Nevertheless, approximately 80% C-terminal cleavage can be achieved within 3 hours at room temperature, making this mutant intein valuable for tag-removal in protein purification. Using Npu*, the present inventors developed one column-free and one chromatography-based protein purification methods by replacing the N-extein with ELP and CBD, respectively, and demonstrated rapid purification (<4 hours) of various target proteins of various sizes and multimeric states to high purity and with high yield (FIGS. 19, 17A, and 18A-18E). However, since reducing agent is employed to trigger intein cleavage, the methods were not tested in the purification of proteins containing naturally occurring disulfide bonds. In the first method, the use of ELP eliminates the need for a costly column and should facilitate its use in large-scale industrial protein purification. In the second method, it is conceivable that other purification tags, such as his-tag, can be used in place of CBD to mediate affinity purification.

For certain embodiments, target protein contains the tripeptide CFN at the N-terminus after purification (FIG. 3). The AS present in constructs 6-10 corresponds to NheI site and was introduced to facilitate the cloning. The Cys+1 is important to render the intein inactive under non-reducing conditions, likely through disulfide-bond formation with Cys1. The function of the Phe+2 and Asn+3 are unknown, but these residues likely do not play a significant role in Npu* C-terminal cleaving activity, as previously reported for the trans-splicing activity in wild-type NpuDnaE. The C-terminal cleavage efficiency depends not only on the immediate extein residues but also on the target protein (FIG. 20). This variability may due to steric hindrance by different target proteins on the association of C* with N, affecting both the affinity between these two fragments as well as the intein catalytic efficiency.

In certain embodiments, the present inventors engineered an NpuDnaE intein via rational design. This intein exhibits rapid C-terminal cleavage kinetics independent of N-terminal cleavage. The present inventors demonstrated the application of this engineered intein for protein purification. Comparing the mutant NpuDnaE intein-based purification methods to the other purification methods mediated by artificially split DnaB intein, the presently disclosed methods eliminate the dependence of small peptide and achieve a much more rapid cleavage rate. Thus, the presently disclosed methods are useful in large-scale protein purification applications.

Example 3

Sample purification via SIRP (FIG. 14): A disposable column containing 150 μL chitin resin was loaded with soluble lysate containing NC1A-CBD in Buffer A (0.5 M NaCl, 10 mM Tris-HCl, pH 8.0) and washed 4 times with 10 column volumes (CV) of Buffer B (0.5 M NaCl, 50 mM NaPOi, pH 6.0). All loading and washing steps were performed in batch phase. The last wash was supplemented with 0.5 mM $ZnCl_2$. The same concentration of $ZnCl_2$ was added to the soluble lysate of C*-PTDH/GFP in Buffer B immediately before the lysate was loaded onto the same chitin resin. The column was subsequently washed with 10 CV of Buffer B with $ZnCl_2$ (0.5 mM) and finally incubated in 4 CV of Buffer A containing 50 mM DTT at room temperature for 30 min or at 6° C. for 3 h. Purified PTDH and GFP were collected in the flow-through. Trace amount NC1A-CBD in the flow-through can be removed by passing through a fresh chitin column. For regeneration of the NC1A-CBD-chitin affinity matrix, the used resin was thoroughly washed with Buffer C (1.5 M NaCl, 50 mM $Na_2HPO_4$/NaOH, pH 11.4, 0.5 mM $ZnCl_2$) to release bound C*. The regenerated column can be stored in storage buffer (0.5 M NaCl, 10 mM Tris-HCl, 1 mM EDTA, 0.15% NaN3, pH 8.0) at 4° C. for about a week without significant loss of activity.

Chemicals and strains: All chemicals were reagent grade and purchased from Sigma-Aldrich (St. Louis, Mo.) or VWR International (Radnor, Pa.), unless otherwise stated. E. coli DH5α (Invitrogen, Grand Island, N.Y.) was used for recombinant DNA cloning and manipulation. E. coli BLR (DE3) (Novagen, Madison, Wis.) was used for the expression of recombinant protein. ONPG was purchased from Research Products International Corp. (Mount Prospect, Ill.). Chitin beads were purchased from New England Biolabs (Ipswich, Mass.).

Plasmid construction: A schematic depiction of the amino acid sequences of certain embodiments, constructs and their numbering are shown in FIG. 3.

To generate C-GFP (construct 1), the NpuC gene was amplified from plasmid KanR-IntRBS-NpuNC-CFN9 using primers NpuC_F_NdeI and OXP-NC-G-Rev, joined to the N-terminal of GFP pet26-GFP with primers OXP-GFP-NC-FWD and XhoI_GFP_R by overlap extension PCR and cloned into pET-26b(+)(Novagen, Madison, Wis.) between NdeI and XhoI sites. Mutation D118G was introduced via site directed mutagenesis to generate C*-GFP (3) with the primers NpuCD17G-F and NpuCD17G-R.

To generate CBD-N (2), NpuN was also amplified from plasmid KanR-IntRBS-NpuNC-CFN9 using primers HindIII-Link-Npu F and NpuN_R_XhoI, joined to the chitin binding domain (CBD), amplified from pTWIN1 (New England BioLabs) with primers NdeI-CBD-F and HindIII-CBD-R via overlap extension PCR, and inserted into the pET-26b(+)(Novagen, Madison, Wis.) between NdeI and XhoI sites. CBD-NpuNC1A (4) was generated by site directed mutagenesis using primers NheI-C1A-F and NpuN-_R_XhoI.

ELP-N (5) was constructed by inserting NpuN (aa 1-102) into plasmid pET-EI:MBP10 between the EcoRI and HindIII sites. NpuN was amplified first using primers HindIII-Link-Npu F and HindIII-6H-NupN-R, then amplified again with primers EcoRI-Linker-NpuN F and HindIII-6H-NupN-R to include the restriction sites and flexible linker.

C*-DsRed (7) was cloned into pET-26b(+)(Novagen, Madison, Wis.) between NdeI and XhoI sites. NpuC* was amplified with primers NpuC_F_NdeI and NheI-NpuC CFN-R from C*-GFP. DsRed was amplified from pTY24 plasmid (NCRR, YRS, Seattle, Wash.) with primers HindII-L-DsRed-fwd and XhoI_DsRed_R. The product was linked to NpuC* by digestion with NheI enzyme resulting in a short linker peptide CFNAS. Aside from the canonical CFN sequence, the "AS" dipeptide corresponds to NheI restriction site and was included to facilitate subsequent cloning.

To clone C*-PTDH (6), the phosphate dehydrogenase "PTDH" was amplified from plasmid PTDH 12×A176R-pet15b11 with primers NheI-PTDH-F and XhoI-PTDH12x-R and inserted into NpuC*-DsRed (7) digested with NheI and XhoI. Plasmid constructs C*-β_Gal (8), C*-CAT (9) and C*-MBP (10) were synthesized in the same way by insertion between NheI and XhoI sites with the appropriate primers. The β-galactosidase gene was amplified from plasmid pET-E-I: β-galactosidase. Similarly, chloramphenicol acetyl transferase (CAT) and maltose binding protein (MBP) genes were amplified from plasmid pET-E-I:CAT and pET-E-MBP (gift from Prof. David Wood), respectively.

Protein expression and purification: E. coli BLR(DE3) was transformed with the appropriate expression plasmid and plated on an agar plate containing 5 μg/mL tetracycline and 100 μg/mL ampicillin (FIG. 3, construct 5) or 5 μg/mL tetracycline and 50 μg/mL kanamycin (all other constructs). The next day, a single colony was picked and grown in 5 mL of Luria-Bertani (LB) broth to OD600~0.6. The culture was transferred to 1 L LB broth containing the same antibiotics and grown at 37° C. until OD600~0.6. Protein expression was induced at 18° C. for 14 hours by the addition of Isopropyl β-D-1-thiogalactopyranoside (IPTG, 0.2 mM). After expression, cells were harvested by centrifugation at 6000×g at 4° C. for 15 minutes and stored at −80° C. until use.

For purification of CBD-N/NC1A (FIG. 3, construct 2, 4), cell pellets were resuspended in Buffer A (0.5 M NaCl, 10 mM Tris-HCl, pH 8.0) at 10 mL per gram of wet pellet, and disrupted by sonication (QSonica Misonix 200, Amp 10, 16-20 W, with 1 sec pulse 6 sec pause for 1 min) Soluble lysates were collected after centrifugation at 16,000×g for 20 minutes at 4° C. and passed through a 5-ml Ni-NTA column (GE Healthcare Life Sciences, Piscataway, N.J.), washed with wash buffer (0.5 M NaCl, 10 mM Tris-HCl, 45 mM Imidazole, pH 8) and eluted in Buffer A containing 150 mM imidazole.

Proteins C/C*-GFP (FIG. 3, Construct 1, 3) were purified in a similar way but with Buffer B (0.5M NaCl, 50 mM NaPOi, pH 6.0, 1x protease inhibitor cocktail (Roche Applied Science, Indianapolis, Ind.)) to minimize proteolytic degradation. Purified protein was buffer-exchanged into Buffer A and concentrated via 10 kDa ultra-filtration spin columns (Amicon Ultra, Millipore, Billerica, Mass.).

For sample purifications using Method 1 (FIG. 16), all cell pellets were resuspended in Buffer A. For sample purifications using Method 2, all cell pellets were resuspended in Column Buffer (1 M NaCl, 10 mM Tris-HCl, pH 8) to increase binding of target protein to chitin resin.

Intein reaction kinetics characterization: All intein characterization experiments were carried out using purified proteins diluted in Buffer A with the indicated amount of reducing agents at specified temperature. All reactions contained 20 µM of each intein fragment. Samples were taken at different time points after the initiation of the reaction, mixed with 2×SDS sample buffer (0.5 M Tris-HCl, pH 6.8, 20% Glycerol, 10% w/v SDS, 0.1% w/v bromo-phenol blue, 2% β-mercaptoethanol), incubated at 95° C. for 5 minutes and analyzed using 12% SDS-PAGE gels, unless otherwise specified. The gels were stained with Coomassie brilliant blue R250. For samples corresponding to 0 min time points, purified C/C*-GFP (construct 1 and 3) protein was first mixed with 2×SDS sample in the absence of β-mercaptoethanol, and incubated at 95° C. for 3 minutes. CBD-N/NC1A (FIG. 3, construct 2 and 4) and β-mercaptoethanol were then added to the mixture. The entire mixture was incubated at 95° C. for additional 3 minutes to inactivate the protein. Band intensities corresponding to reactants and products were quantified using Trace Quantity module in Quantity One software (BioRad, Hercules, Calif.).

Protein purification via reversible precipitation of elastin-like-peptide: In this embodiment, ELP-N (FIG. 3, construct 5) was pre-purified with one round of ammonium sulfate precipitation to facilitate the interpretation of SDS-PAGE gels, although this step was not found to improve the efficiency of protein purification. Clarified cell lysates of ELP-N and C*-POI (FIG. 3, construct 3, 6-10) were thoroughly mixed and incubated at room temperature for 10 min to allow association of C* and N (FIG. 17A, lane 3). Ammonium sulfate (0.4 M final concentration) was added to the mixture to induce precipitation of the ELP complex. The pellet containing the target protein non-covalently linked to ELP was resuspended in Buffer A (FIG. 17A, lane 5). The intein reaction was initiated by the addition of DTT (50 mM) and was carried out at room temperature for 3 or 20 hours. It is possible to use a much lower DTT concentration to induce C-terminal cleavage (FIG. 7). At the end of the reaction, ammonium sulfate (0.4 M) was added to the mixture to precipitate out the ELP-N/C* complex. This precipitant was removed by centrifugation. The supernatant contained the highly purified target protein (FIG. 17A, lane 8, 9).

Protein purification via chitin resin: A slurry of chitin beads was first incubated with lysate of CBD-N (FIG. 3, construct 2) at room temperature for 10 min, washed extensively with Column Buffer to remove all contaminating proteins (FIG. 17C, lane 3), and then loaded with lysate containing C*-GFP (FIG. 3, construct 3). After washing, DTT (5 mM) was added to the mixture to induce C-terminal cleavage. The reaction was essentially complete after 3 hours of reaction at room temperature (FIG. 17C, lane 5) and purified GFP was collected in the flow-through (FIG. 17C, lane 7). CBD-N, as well as trace amount of unreacted C*-GFP remained bound to the chitin beads (FIG. 17C, lane 6). Cleaved C*, although not visible on the gel due to its very small size (4 kDa), was presumed to remain on the column due to interaction with N.

Molecular modeling: the structures of mini-MtuRecA (pdb: 2 IMZ), NpuDnaE (pdb: 2 KEQ) and SspDnaE (pdb: 1ZD7) were visualized using Visual Molecular Dynamics (VMD), and aligned using the MultiSeq module in VMD. Hydrogen bond interactions were identified by VMD. The NMR structure of NpuDnaE contains 20 different solution structures. For clarity, only alignment of SspDnaE with structure #7 of NpuDnaE is shown in FIG. 5C.

Temperature dependent kinetics: To determine the half-life for the C-terminal cleavage reaction of C*-GFP at different temperatures, trend line was generated using Lab Fit software package (Campina Grande, Paraiba, Brazil) that best fit all the data points from FIG. 7C. Time corresponding to 50% cleavage was estimated based on the fit curve.

Estimated half-lifes for C*-GFP cleavage at different temperatures:

| Temperature | Half-life |
| --- | --- |
| 4 C. | 243 min |
| 16 C. | 70 min |
| 22 C. | 55 min |
| 37 C. | 16 min |

Purified protein content quantification: Target protein purification yield was quantified by measuring the concentration of purified sample using the Bradford method (Coomassie Plus Bradford Assay Reagent, Pierce Biotechnology, Rockford, Ill.). To estimate the percent recovery, soluble lysate and purified protein were loaded on the same SDS-PAGE stained with SimplyBlue SafeStain (Life Technology, Carlsbad, Calif.), and the band intensity corresponding to the target protein were measured using the Trace Quantity module in Quantity One software (BioRad, Hercules, Calif.).

Pre-purification of ELP-N: Ammonium sulfate (0.4 M) was added to the soluble lysate to induce ELP-N phase separation. The mixture was incubated at room temperature for ~3 min and centrifuged at 14,000×g for 10 min. The resulting pellet was resuspended in one third of the original volume of buffer A. A low intensity water-bath sonicator (Ultrasonic Cleaner, GB 928) was used (5 min) to aid the resuspension of ELP-N.

Sample protein activity assays: The activity of purified PTDH was confirmed by the NBT assay as described by Mayer et al. Since DTT interferes with the NBT reaction at high concentration, the DTT concentration in purified protein was reduced to ~5 µM by buffer exchange using a 30-kDa cut-off spin column (Amicon Ultra-15 Centrifugal Filter Unit, Millipore, Billerica, Mass.) before the assay.

The activity of MBP was confirmed by binding to amylose resin (New England Biolabs, Ipswich, Mass.). Amylose beads (25 µL) were incubated with purified protein (500 µL) at room temperature for 10 min, washed twice with 500 µL buffer A and resuspended in 500 µL of Buffer A. Ten µL of this suspension was mixed with 10 µL of 2×SDS loading buffer, boiled at 95° C. for three minutes and analyzed via SDS-PAGE. The MBP protein was visible in the amylose beads suspension but not in the wash buffer.

The proteins GFP and DsRed were assayed by fluorescence measurements against the non-fluorescent protein CAT. Purified GFP or DsRed were diluted 2-fold and transferred to a 96-well plate (150 µL/well). The fluorescence intensity was measured using a spectrofluorometer SpectraMax Gemini EM (Molecular Devices, Sunnyvale, Calif.) with excitation/emission wavelengths of 485/538 nm (GFP) or 544/590 nm (DsRed). The control protein CAT generated background values in both assays.

β-galactosidase activity was measured by the hydrolysis of o-Nitrophenyl β-D-galactopyranoside (ONPG) to o-nitrophenol, which absorbs at 420 nm. Purified β-galactosidase was diluted 1000-fold in Z-buffer (0.06 M Na2HPO4, 0.04 M NaH2PO4, 0.01 M KCl, 0.001 M MgSO4, and 0.27% 2-mercaptoethanol). Diluted protein (30 µL) was mixed with Z buffer (200 µL) and ONPG (70 µL, 4 mg/mL in 100 mM Potassium Phosphate buffer pH 7) and incubated at 22° C. for 15 or 30 minutes. At the end of the reaction, 500 µL stopping buffer (1 M Na2CO3) was added and the absorbance at 420 nm was measured in a Biomate 3 spectrophotometer (Thermo Electron Corporation).

To estimate the enzymatic units of β-galactosidase, the following formula was used:

$$\text{nmoles } ONPG \text{ hydrolized} = \frac{(OD_{420}) * (8 \times 10^5 \text{ nanoliters})}{\left(4500 \frac{nl}{nmoles \, cm}\right)(1 \text{ cm})}$$

$8 \times 10^5$ nanoliters is the volume of the reaction; 4500 M−1 cm−1 is the extinction coefficient of o-nitrophenol; and 1-cm is the length of the light path. One unit of β-galactosidase is defined as the amount of enzyme necessary to hydrolyze one micromole of ONPG at 22° C. per minute.

$$\text{Unit number} = \frac{\mu\text{moles } ONPG \text{ hydrolize}}{\text{time}}$$

$$\text{Specific Units} = \frac{\text{Unit number}}{\text{mg of enzyme used}}$$

To estimate the sample recovery of β-galactosidase, a similar activity assay was carried out in a 96-well plate by diluting the purified β-galactosidase 1000-fold in Z-buffer. Diluted protein (50 µL) was mixed with Z buffer (50 µL) and 10 µl of ONPG solution. Absorbance at 420 nm was measured after 20-minute incubation using a SpectraMax 340PC384 Absorbance Microplate Reader (Molecular Devices, Sunnyvale, Calif.).

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. As used herein, the phrase "consisting essentially of" limits the scope of a claim to the specified materials or steps and those that do not materially affect the basic and novel characteristic(s) of the claimed invention. As used herein, the phrase "consisting of" excludes any element, step, or ingredient not specified in the claim except for, e.g., impurities ordinarily associated with the element or limitation.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context. In certain embodiments, the present invention may also include methods and compositions in which the transition phrase "consisting essentially of" or "consisting of" may also be used.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

Listing of sequences used:

```
Construct 1
C-GFP:
                                           (SEQ ID NO: 1)
ATGATCAAAATAGCCACACGTAAATATTTAGGCAAACAAAATGTC

TATGACATTGGAGTTGAGCGCGACCATAATTTTGCACTCAAAAAT

GGCTTCATAGCTTCTAATTGTTTCAATGTGAGCAAGGGCGAGGAG

CTGTTCACCGGGGTGGTGCCCATCCTGGTCGAGCTGGACGGCGAC

GTAAACGGCCACAAGTTCAGCGTGTCCGGCGAGGGCGAGGGCGAT

GCCACCTACGGCAAGCTGACCCTGAAGTTCATCTGCACCACCGGC

AAGCTGCCCGTGCCCTGGCCCACCCTCGTGACCACCCTGACCTAC

GGCGTGCAGTGCTTCAGCCGCTACCCCGACCACATGAAGCAGCAC

GACTTCTTCAAGTCCGCCATGCCCGAAGGCTACGTCCAGGAGCGC

ACCATCTTCTTCAAGGACGACGGCAACTACAAGACCCGCGCCGAG

GTGAAGTTCGAGGGCGACACCCTGGTGAACCGCATCGAGCTGAAG

GGCATCGACTTCAAGGAGGACGGCAACATCCTGGGGCACAAGCTG

GAGTACAACTACAACAGCCACAACGTCTATATCATGGCCGACAAG

CAGAAGAACGGCATCAAGGTGAACTTCAAGATCCGCCACAACATC

GAGGACGGCAGCGTGCAGCTCGCCGACCACTACCAGCAGAACACC

CCCATCGGCGACGGCCCCGTGCTGCTGCCCGACAACCACTACCTG

AGCACCCAGTCCGCCCTGAGCAAAGACCCCAACGAGAAGCGCGAT

CACATGGTCCTGCTGGAGTTCGTGACCGCCGCCGGGATCACTCTC

GGCATGGACGAGTTACTCGAGCACCACCACCACCAC

C-GFP translated:
                                           (SEQ ID NO: 2)
MIKIATRKYLGKQNVYDIGVERDHNFALKNGFIASNCFNVSKGEE

LFTGVVPILVELDGDVNGHKFSVSGEGEGDATYGKLTLKFICTTG

KLPVPWPTLVTTLTYGVQCFSRYPDHMKQHDFFKSAMPEGYVQER

TIFFKDDGNYKTRAEVKFEGDTLVNRIELKGIDFKEDGNILGHKL

EYNYNSHNVYIMADKQKNGIKVNFKIRHNIEDGSVQLADHYQQNT

PIGDGPVLLPDNHYLSTQSALSKDPNEKRDHMVLLEFVTAAGITL

GMDELLEHHHHH

Construct 2
CBD-N
                                           (SEQ ID NO: 3)
ATGAAAATCGAAGAAGGTAAACTGACAAATCCTGGTGTATCCGCT

TGGCAGGTCAACACAGCTTATACTGCGGGACAATTGGTCACATAT

AACGGCAAGACGTATAAATGTTTGCAGCCCCACACCTCCTTGGCA

GGATGGGAACCATCCAACGTTCCTGCCTTGTGGCAGCTTCAAGAA

GCTTGTGGAGGCGGAGGGAGCGGAGGCGGAGGGAGCGCTAGCTGT

TTAAGCTATGAAACGGAAATATTGACAGTAGAATATGGATTATTA

CCGATTGGTAAAATTGTAGAAAAGCGCATCGAATGTACTGTTTAT

AGCGTTGATAATAATGGAAATATTTATACACAACCTGTAGCACAA

TGGCACGATCGCGGAGAACAAGAGGTGTTTGAGTATTGTTTGAA

GATGGTTCATTGATTCGGGCAACAAAAGACCATAAGTTTATGACT

GTTGATGGTCAAATGTTGCCAATTGATGAAATATTTGAACGTGAA

TTGGATTTGATGCGGGTTGATAATTTGCCGAATCTCGAGCACCAC

CACCACCACCAC

CBD-N translated:
                                           (SEQ ID NO: 4)
MKIEEGKLTNPGVSAWQVNTAYTAGQLVTYNGKTYKCLQPHTSLA

GWEPSNVPALWQLQEACGGGGSGGGGSASCLSYETEILTVEYGLL

PIGKIVEKRIECTVYSVDNNGNIYTQPVAQWHDRGEQEVFEYCLE

DGSLIRATKDHKFMTVDGQMLPIDEIFERELDLMRVDNLPNLEHH

HHHH

Construct 3
C*-GFP:
                                           (SEQ ID NO: 5)
ATGATCAAAATAGCCACACGTAAATATTTAGGCAAACAAAATGTC

TATGGCATTGGAGTTGAGCGCGACCATAATTTTGCACTCAAAAAT

GGCTTCATAGCTTCTAATTGTTTCAATGTGAGCAAGGGCGAGGAG

CTGTTCACCGGGGTGGTGCCCATCCTGGTCGAGCTGGACGGCGAC

GTAAACGGCCACAAGTTCAGCGTGTCCGGCGAGGGCGAGGGCGAT

GCCACCTACGGCAAGCTGACCCTGAAGTTCATCTGCACCACCGGC

AAGCTGCCCGTGCCCTGGCCCACCCTCGTGACCACCCTGACCTAC

GGCGTGCAGTGCTTCAGCCGCTACCCCGACCACATGAAGCAGCAC

GACTTCTTCAAGTCCGCCATGCCCGAAGGCTACGTCCAGGAGCGC

ACCATCTTCTTCAAGGACGACGGCAACTACAAGACCCGCGCCGAG

GTGAAGTTCGAGGGCGACACCCTGGTGAACCGCATCGAGCTGAAG

GGCATCGACTTCAAGGAGGACGGCAACATCCTGGGGCACAAGCTG

GAGTACAACTACAACAGCCACAACGTCTATATCATGGCCGACAAG

CAGAAGAACGGCATCAAGGTGAACTTCAAGATCCGCCACAACATC

GAGGACGGCAGCGTGCAGCTCGCCGACCACTACCAGCAGAACACC

CCCATCGGCGACGGCCCCGTGCTGCTGCCCGACAACCACTACCTG

AGCACCCAGTCCGCCCTGAGCAAAGACCCCAACGAGAAGCGCGAT

CACATGGTCCTGCTGGAGTTCGTGACCGCCGCCGGGATCACTCTC

GGCATGGACGAGTTACTCGAGCACCACCACCACCAC

C*-GFP translated:
                                           (SEQ ID NO: 6)
MIKIATRKYLGKQNVYGIGVERDHNFALKNGFIASNCFNVSKGEE

LFTGVVPILVELDGDVNGHKFSVSGEGEGDATYGKLTLKFICTTG

KLPVPWPTLVTTLTYGVQCFSRYPDHMKQHDFFKSAMPEGYVQER
```

-continued

TIFFKDDGNYKTRAEVKFEGDTLVNRIELKGIDFKEDGNILGHKL

EYNYNSHNVYIMADKQKNGIKVNFKIRHNIEDGSVQLADHYQQNT

PIGDGPVLLPDNHYLSTQSALSKDPNEKRDHMVLLEFVTAAGITL

GMDELLEHHHHHH

Construct 4
CBD-NC1A
(SEQ ID NO: 7)
ATGAAAATCGAAGAAGGTAAACTGACAAATCCTGGTGTATCCGCT

TGGCAGGTCAACACAGCTTATACTGCGGGACAATTGGTCACATAT

AACGGCAAGACGTATAAATGTTTGCAGCCCCACACCTCCTTGGCA

GGATGGGAACCATCCAACGTTCCTGCCTTGTGGCAGCTTCAAGAA

GCTTGTGGAGGCGGAGGGAGCGGAGGCGGAGGGAGCGCTAGCGCC

TTAAGCTATGAAACGGAAATATTGACAGTAGAATATGGATTATTA

CCGATTGGTAAAATTGTAGAAAAGCGCATCGAATGTACTGTTTAT

AGCGTTGATAATAATGGAAATATTTATACACAACCTGTAGCACAA

TGGCACGATCGCGGAGAACAAGAGGTGTTTGAGTATTGTTTGGAA

GATGGTTCATTGATTCGGGCAACAAAAGACCATAAGTTTATGACT

GTTGATGGTCAAATGTTGCCAATTGATGAAATATTTGAACGTGAA

TTGGATTTGATGCGGGTTGATAATTTGCCGAATCTCGAGCACCAC

CACCACCACCAC

CBD-NC1A translated:
(SEQ ID NO: 8)
MKIEEGKLTNPGVSAWQVNTAYTAGQLVTYNGKTYKCLQPHTSLA

GWEPSNVPALWQLQEACGGGGSGGGGSASALSYETEILTVEYGLL

PIGKIVEKRIECTVYSVDNNGNIYTQPVAQWHDRGEQEVFEYCLE

DGSLIRATKDHKFMTVDGQMLPIDEIFERELDLMRVDNLPNLEHH

HHHH

Construct 5
ELP-N
(SEQ ID NO: 9)
ATGGGCCACGGCGTGGGTGTTCCGGGCGTGGGTGTTCCGGGTGGC

GGTGTGCCGGGCGCAGGTGTTCCTGGTGTAGGTGTGCCGGGTGTT

GGTGTGCCGGGTGTTGGTGTACCAGGTGGCGGTGTTCCGGGTGCA

GGCGTTCCGGGTGGCGGTGTGCCGGGCGTGGGTGTTCCGGGCGTG

GGTGTTCCGGGTGGCGGTGTGCCGGGCGCAGGTGTTCCTGGTGTA

GGTGTGCCGGGTGTTGGTGTGCCGGGTGTTGGTGTACCAGGTGGC

GGTGTTCCGGGTGCAGGCGTTCCGGGTGGCGGTGTGCCGGGCGTG

GGTGTTCCGGGCGTGGGTGTTCCGGGTGGCGGTGTGCCGGGCGCA

GGTGTTCCTGGTGTAGGTGTGCCGGGTGTTGGTGTGCCGGGTGTT

GGTGTACCAGGTGGCGGTGTTCCGGGTGCAGGCGTTCCGGGTGGC

GGTGTGCCGGGCGTGGGTGTTCCGGGCGTGGGTGTTCCGGGTGGC

GGTGTGCCGGGCGCAGGTGTTCCTGGTGTAGGTGTGCCGGGTGTT

GGTGTGCCGGGTGTTGGTGTACCAGGTGGCGGTGTTCCGGGTGCA

GGCGTTCCGGGTGGCGGTGTGCCGGGCGTGGGTGTTCCGGGCGTG

GGTGTTCCGGGTGGCGGTGTGCCGGGCGCAGGTGTTCCTGGTGTA

GGTGTGCCGGGTGTTGGTGTGCCGGGTGTTGGTGTACCAGGTGGC

GGTGTTCCGGGTGCAGGCGTTCCGGGTGGCGGTGTGCCGGGCGTG

GGTGTTCCGGGCGTGGGTGTTCCGGGTGGCGGTGTGCCGGGCGCA

GGTGTTCCTGGTGTAGGTGTGCCGGGTGTTGGTGTGCCGGGTGTT

GGTGTACCAGGTGGCGGTGTTCCGGGTGCAGGCGTTCCGGGTGGC

GGTGTGCCGGGCGTGGGTGTTCCGGGCGTGGGTGTTCCGGGTGGC

GGTGTGCCGGGCGCAGGTGTTCCTGGTGTAGGTGTGCCGGGTGTT

GGTGTGCCGGGTGTTGGTGTACCAGGTGGCGGTGTTCCGGGTGCA

GGCGTTCCGGGTGGCGGTGTGCCGGGCGTGGGTGTTCCGGGCGTG

GGTGTTCCGGGTGGCGGTGTGCCGGGCGCAGGTGTTCCTGGTGTA

GGTGTGCCGGGTGTTGGTGTGCCGGGTGTTGGTGTACCAGGTGGC

GGTGTTCCGGGTGCAGGCGTTCCGGGTGGCGGTGTGCCGGGCGGG

CTGGTGAGCTCGAACAACAACAACAATAACAATAACAACAACCTC

GGGATCGAGGGAAGGATTTCAGAATTCGGAGGCGGAGGGAGCGGA

GGCGGAGGGAGCGCTAGCTGTTTAAGCTATGAAACGGAAATATTG

ACAGTAGAATATGGATTATTACCGATTGGTAAAATTGTAGAAAAG

CGCATCGAATGTACTGTTTATAGCGTTGATAATAATGGAAATATT

TATACACAACCTGTAGCACAATGGCACGATCGCGGAGAACAAGAG

GTGTTTGAGTATTGTTTGGAAGATGGTTCATTGATTCGGGCAACA

AAAGACCATAAGTTTATGACTGTTGATGGTCAAATGTTGCCAATT

GATGAAATATTTGAACGTGAATTGGATTTGATGCGGGTTGATAAT

TTGCCGAATCTCGAGCACCACCACCACCACCAC

ELP-N translated:
(SEQ ID NO: 10)
MGHGVGVPGVGVPGGGVPGAGVPGVGVPGVGVPGVGVPGGGVPGA

GVPGGGVPGVGVPGVGVPGGGVPGAGVPGVGVPGVGVPGVGVPGG

GVPGAGVPGGGVPGVGVPGVGVPGGGVPGAGVPGVGVPGVGVPGV

GVPGGGVPGAGVPGGGVPGVGVPGVGVPGGGVPGAGVPGVGVPGV

GVPGVGVPGGGVPGAGVPGGGVPGVGVPGVGVPGGGVPGAGVPGV

GVPGVGVPGVGVPGGGVPGAGVPGGGVPGVGVPGVGVPGGGVPGA

GVPGVGVPGVGVPGVGVPGGGVPGAGVPGGGVPGVGVPGVGVPGG

GVPGAGVPGVGVPGVGVPGVGVPGGGVPGAGVPGGGVPGVGVPGV

GVPGGGVPGAGVPGVGVPGVGVPGVGVPGGGVPGAGVPGGGVPGV

GVPGVGVPGGGVPGAGVPGVGVPGVGVPGVGVPGGGVPGAGVPGG

GVPGVGVPGVGVPGGGVPGAGVPGVGVPGVGVPGVGVPGGGVPGA

GVPGGGVPGVGVPGVGVPGGGVPGAGVPGVGVPGVGVPGVGVPGG

GVPGAGVPGGGVPGGLVSSNNNNNNNNNNLGIEGRISEFGGGGSG

GGGSASCLSYETEILTVEYGLLPIGKIVEKRIECTVYSVDNNGNI

YTQPVAQWHDRGEQEVFEYCLEDGSLIRATKDHKFMTVDGQMLPI

DEIFERELDLMRVDNLPNLEHHHHHH

Construct 6
C*-PTDH:
(SEQ ID NO: 11)
ATGATCAAAATAGCCACACGTAAATATTTAGGCAAACAAAATGTC

TATGGCATTGGAGTTGAGCGCGACCATAATTTTGCACTCAAAAAT

GGCTTCATAGCTTCTAATTGTTTCAATGCTAGCATGCTGCCGAAA

CTCGTTATAACTCACCGAGTACACGAAGAGATCCTGCAACTGCTG

GCGCCACATTGCGAGCTGATAACCAACCAGACCGACAGCACGCTG

ACGCGCGAGGAAATTCTGCGCCGCTGTCGCGATGCTCAGGCGATG

ATGGCGTTCATGCCCGATCGGGTCGATGCAGACTTTCTTCAAGCC

TGCCCTGAGCTGCGTGTAATCGGCTGCGCGCTCAAGGGCTTCGAC

AATTTCGATGTGGACGCCTGTACTGCCCGCGGGGTCTGGCTGACC

TTCGTGCCTGATCTGTTGACGGTCCCGACTGCCGAGCTGGCGATC

GGACTGGCGGTGGGGCTGGGGCGGCATCTGCGGGCAGCAGATGCG

TTCGTCCGCTCTGGCAAGTTCCGGGGCTGGCAACCACGGTTCTAC

GGCACGGGGCTGGATAACGCTACGGTCGGCTTCCTTGGCATGGGC

GCCATCGGACTGGCCATGGCTGATCGCTTGCAGGGATGGGGCGCG

ACCCTGCAGTACCACGCGCGGAAGGCTCTGGATACACAAACCGAG

CAACGGCTCGGCCTGCGCCAGGTGGCGTGCAGCGAACTCTTCGCC

AGCTCGGACTTCATCCTGCTGGCGCTTCCCTTGAATGCCGATACC

CTGCATCTGGTCAACGCCGAGCTGCTTGCCCTCGTACGGCCGGGC

GCTCTGCTTGTAAACCCCTGTCGTGGCTCGGTAGTGGATGAAGCC

GCCGTGCTCGCGGCGCTTGAGCGAGGCCAGCTCGGCGGGTATGCG

GCGGATGTATTCGAAATGGAAGACTGGGCTCGCGCGGACCGGCCG

CAGCAGATCGATCCTGCGCTGCTCGCGCATCCGAATACGCTGTTC

ACTCCGCACATAGGGTCGGCAGTGCGCGCGGTGCGCCTGGAGATT

GAACGTTGTGCAGCGCAGAACATCCTCCAGGCATTGGCAGGTGAG

CGCCCAATCAACGCTGTGAACCGTCTGCCCAAGGCCAATCCTGCC

GCAGACCTCGAGCACCACCACCACCACCAC

C*-PTDH Translated:
(SEQ ID NO: 12)
MIKIATRKYLGKQNVYGIGVERDHNFALKNGFIASNCFNASMLPK

LVITHRVHEEILQLLAPHCELITNQTDSTLTREEILRRCRDAQAM

MAFMPDRVDADFLQACPELRVIGCALKGFDNFDVDACTARGVWLT

FVPDLLTVPTAELAIGLAVGLGRHLRAADAFVRSGKFRGWQPRFY

GTGLDNATVGFLGMGAIGLAMADRLQGWGATLQYHARKALDTQTE

QRLGLRQVACSELFASSDFILLALPLNADTLHLVNAELLALVRPG

ALLVNPCRGSVVDEAAVLAALERGQLGGYAADVFEMEDWARADRP

QQIDPALLAHPNTLFTPHIGSAVRAVRLEIERCAAQNILQALAGE

RPINAVNRLPKANPAADLEHHHHHH

Construct 7
C*-DsRed
(SEQ ID NO: 13)
ATGATCAAAATAGCCACACGTAAATATTTAGGCAAACAAAATGTC

TATGGCATTGGAGTTGAGCGCGACCATAATTTTGCACTCAAAAAT

GGCTTCATAGCTTCTAATTGTTTCAATGCTAGCGCCTCCTCCGAG

GACGTCATCAAGGAGTTCATGCGCTTCAAGGTGCGCATGGAGGGC

TCCGTGAACGGCCACGAGTTCGAGATCGAGGGCGAGGGCGAGGGC

CGCCCCTACGAGGGCACCCAGACCGCCAAGCTGAAGGTGACCAAG

GGCGGCCCCCTGCCCTTCGCCTGGGACATCCTGTCCCCCCAGTTC

CAGTACGGCTCCAAGGTGTACGTGAAGCACCCCGCCGACATCCCC

GACTACAAGAAGCTGTCCTTCCCCGAGGGCTTCAAGTGGGAGCGC

GTGATGAACTTCGAGGACGGCGGCGTGGTGACCGTGACCCAGGAC

TCCTCCCTGCAGGACGGCTCCTTCATCTACAAGGTGAAGTTCATC

GGCGTGAACTTCCCCTCCGACGGCCCCGTAATGCAGAAGAAGACT

ATGGGCTGGGAGGCCTCCACCGAGCGCCTGTACCCCCGCGACGGC

GTGCTGAAGGGCGAGATCCACAAGGCCCTGAAGCTGAAGGACGGC

GGCCACTACCTGGTGGAGTTCAAGTCCATCTACATGGCCAAGAAG

CCCGTGCAGCTGCCCGGCTACTACTACGTGGACTCCAAGCTGGAC

ATCACCTCCCACAACGAGGACTACACCATCGTGGAGCAGTACGAG

CGCGCCGAGGGCCGCCACCACCTGTTCCTGCTCGAGCACCACCAC

CACCACCAC

C*-DsRed translated:
(SEQ ID NO: 14)
MIKIATRKYLGKQNVYGIGVERDHNFALKNGFIASNCFNASASSE

DVIKEFMRFKVRMEGSVNGHEFEIEGEGEGRPYEGTQTAKLKVTK

GGPLPFAWDILSPQFQYGSKVYVKHPADIPDYKKLSFPEGFKWER

VMNFEDGGVVTVTQDSSLQDGSFIYKVKFIGVNFPSDGPVMQKKT

MGWEASTERLYPRDGVLKGEIHKALKLKDGGHYLVEFKSIYMAKK

PVQLPGYYYVDSKLDITSHNEDYTIVEQYERAEGRHHLFLLEHHH

HHH

Construct 8
C*-β-Gal
(SEQ ID NO: 15)
ATGATCAAAATAGCCACACGTAAATATTTAGGCAAACAAAATGTC

TATGGCATTGGAGTTGAGCGCGACCATAATTTTGCACTCAAAAAT

GGCTTCATAGCTTCTAATTGTTTCAATGCTAGCATGACCATGATT

ACGGATTCACTCGCCGTCGTTTTACAACGTCGTGACTGGGAAAAC

```
CCTGGCGTTACCCAACTTAATCGCCTTGCAGCACATCCCCCTTTC
GCCAGCTGGCGTAATAGCGAAGAGGCCCGCACCGATCGCCCTTCC
CAACAGTTGCGCAGCCTGAATGGCGAATGGCGCTTTGCCTGGTTT
CCGGCACCAGAAGCGGTGCCGGAAAGCTGGCTGGAGTGCGATCTT
CCTGAGGCCGATACTGTCGTCGTCCCCTCAAACTGGCAGATGCAC
GGTTACGATGCGCCCATCTACACCAACGTGACCTATCCCATTACG
GTCAATCCGCCGTTTGTTCCCACGGAGAATCCGACGGGTTGTTAC
TCGCTCACATTTAATGTTGATGAAAGCTGGCTACAGGAAGGCCAG
ACGCGAATTATTTTTGATGGCGTTAACTCGGCGTTTCATCTGTGG
TGCAACGGGCGCTGGGTCGGTTACGGCCAGGACAGTCGTTTGCCG
TCTGAATTTGACCTGAGCGCATTTTTACGCGCCGGAGAAAACCGC
CTCGCGGTGATGGTGCTGCGCTGGAGTGACGGCAGTTATCTGGAA
GATCAGGATATGTGGCGGATGAGCGGCATTTTCCGTGACGTCTCG
TTGCTGCATAAACCGACTACACAAATCAGCGATTTCCATGTTGCC
ACTCGCTTTAATGATGATTTCAGCCGCGCTGTACTGGAGGCTGAA
GTTCAGATGTGCGGCGAGTTGCGTGACTACCTACGGGTAACAGTT
TCTTTATGGCAGGGTGAAACGCAGGTCGCCAGCGGCACCGCGCCT
TTCGGCGGTGAAATTATCGATGAGCGTGGTGGTTATGCCGATCGC
GTCACACTACGTCTGAACGTCGAAAACCCGAAACTGTGGAGCGCC
GAAATCCCGAATCTCTATCGTGCGGTGGTTGAACTGCACACCGCC
GACGGCACGCTGATTGAAGCAGAAGCCTGCGATGTCGGTTTCCGC
GAGGTGCGGATTGAAAATGGTCTGCTGCTGCTGAACGGCAAGCCG
TTGCTGATTCGAGGCGTTAACCGTCACGAGCATCATCCTCTGCAT
GGTCAGGTCATGGATGAGCAGACGATGGTGCAGGATATCCTGCTG
ATGAAGCAGAACAACTTTAACGCCGTGCGCTGTTCGCATTATCCG
AACCATCCGCTGTGGTACACGCTGTGCGACCGCTACGGCCTGTAT
GTGGTGGATGAAGCCAATATTGAAACCCACGGCATGGTGCCAATG
AATCGTCTGACCGATGATCCGCGCTGGCTACCGGCGATGAGCGAA
CGCGTAACGCGAATGGTGCAGCGCGATCGTAATCACCCGAGTGTG
ATCATCTGGTCGCTGGGGAATGAATCAGGCCACGGCGCTAATCAC
GACGCGCTGTATCGCTGGATCAAATCTGTCGATCCTTCCCGCCCG
GTGCAGTATGAAGGCGGCGGAGCCGACACCACGGCCACCGATATT
ATTTGCCCGATGTACGCGCGCGTGGATGAAGACCAGCCCTTCCCG
GCTGTGCCGAAATGGTCCATCAAAAAATGGCTTTCGCTACCTGGA
GAGACGCGCCCGCTGATCCTTTGCGAATACGCCCACGCGATGGGT
AACAGTCTTGGCGGTTTCGCTAAATACTGGCAGGCGTTTCGTCAG
TATCCCCGTTTACAGGGCGGCTTCGTCTGGGACTGGGTGGATCAG
TCGCTGATTAAATATGATGAAAACGGCAACCCGTGGTCGGCTTAC
GGCGGTGATTTTGGCGATACGCCGAACGATCGCCAGTTCTGTATG
AACGGTCTGGTCTTTGCCGACCGCACGCCGCATCCAGCGCTGACG
GAAGCAAAACACCAGCAGCAGTTTTTCCAGTTCCGTTTATCCGGG
```

```
CAAACCATCGAAGTGACCAGCGAATACCTGTTCCGTCATAGCGAT
AACGAGCTCCTGCACTGGATGGTGGCGCTGGATGGTAAGCCGCTG
GCAAGCGGTGAAGTGCCTCTGGATGTCGCTCCACAAGGTAAACAG
TTGATTGAACTGCCTGAACTACCGCAGCCGGAGAGCGCCGGGCAA
CTCTGGCTCACAGTACGCGTAGTGCAACCGAACGCGACCGCATGG
TCAGAAGCCGGGCACATCAGCGCCTGGCAGCAGTGGCGTCTGGCG
GAAAACCTCAGTGTGACGCTCCCCGCCGCGTCCCACGCCATCCCG
CATCTGACCACCAGCGAAATGGATTTTTGCATCGAGCTGGGTAAT
AAGCGTTGGCAATTTAACCGCCAGTCAGGCTTTCTTTCACAGATG
TGGATTGGCGATAAAAAACAACTGCTGACGCCGCTGCGCGATCAG
TTCACCCGTGCACCGCTGGATAACGACATTGGCGTAAGTGAAGCG
ACCCGCATTGACCCTAACGCCTGGGTCGAACGCTGGAAGGCGGCG
GGCCATTACCAGGCCGAAGCAGCGTTGTTGCAGTGCACGGCAGAT
ACACTTGCTGATGCGGTGCTGATTACGACCGCTCACGCGTGGCAG
CATCAGGGGAAAACCTTATTTATCAGCCGGAAAACCTACCGGATT
GATGGTAGTGGTCAAATGGCGATTACCGTTGATGTTGAAGTGGCG
AGCGATACACCGCATCCGGCGCGGATTGGCCTGAACTGCCAGCTG
GCGCAGGTAGCAGAGCGGGTAAACTGGCTCGGATTAGGGCCGCAA
GAAAACTATCCCGACCGCCTTACTGCCGCCTGTTTTGACCGCTGG
GATCTGCCATTGTCAGACATGTATACCCCGTACGTCTTCCCGAGC
GAAAACGGTCTGCGCTGCGGGACGCGCGAATTGAATTATGGCCCA
CACCAGTGGCGCGGCGACTTCCAGTTCAACATCAGCCGCTACAGT
CAACAGCAACTGATGGAAACCAGCCATCGCCATCTGCTGCACGCG
GAAGAAGGCACATGGCTGAATATCGACGGTTTCCATATGGGGATT
GGTGGCGACGACTCCTGGAGCCCGTCAGTATCGGCGGAATTCCAG
CTGAGCGCCGGTCGCTACCATTACCAGTTGGTCTGGTGTCAAAAA
CTCGAGCACCACCACCACCACCAC
```

C*-β-Gal translated:

(SEQ ID NO: 16)
MIKIATRKYLGKQNVYGIGVERDHNFALKNGFIASNCFNASMTMI
TDSLAVVLQRRDWENPGVTQLNRLAAHPPFASWRNSEEARTDRPS
QQLRSLNGEWRFAWFPAPEAVPESWLECDLPEADTVVVPSNWQMH
GYDAPIYTNVTYPITVNPPFVPTENPTGCYSLTFNVDESWLQEGQ
TRIIFDGVNSAFHLWCNGRWVGYGQDSRLPSEFDLSAFLRAGENR
LAVMVLRWSDGSYLEDQDMWRMSGIFRDVSLLHKPTTQISDFHVA
TRFNDDFSRAVLEAEVQMCGELRDYLRVTVSLWQGETQVASGTAP
FGGEIIDERGGYADRVTLRLNVENPKLWSAEIPNLYRAVVELHTA
DGTLIEAEACDVGFREVRIENGLLLLNGKPLLIRGVNRHEHHPLH
GQVMDEQTMVQDILLMKQNNFNAVRCSHYPNHPLWYTLCDRYGLY
VVDEANIETHGMVPMNRLTDDPRWLPAMSERVTRMVQRDRNHPSV
IIWSLGNESGHGANHDALYRWIKSVDPSRPVQYEGGGADTTATDI

```
ICPMYARVDEDQPFPAVPKWSIKKWLSLPGETRPLILCEYAHAMG
NSLGGFAKYWQAFRQYPRLQGGFVWDWVDQSLIKYDENGNPWSAY
GGDFGDTPNDRQFCMNGLVFADRTPHPALTEAKHQQQFFQFRLSG
QTIEVTSEYLFRHSDNELLHWMVALDGKPLASGEVPLDVAPQGKQ
LIELPELPQPESAGQLWLTVRVVQPNATAWSEAGHISAWQQWRLA
ENLSVTLPAASHAIPHLTTSEMDFCIELGNKRWQFNRQSGFLSQM
WIGDKKQLLTPLRDQFTRAPLDNDIGVSEATRIDPNAWVERWKAA
GHYQAEAALLQCTADTLADAVLITTAHAWQHQGKTLFISRKTYRI
DGSGQMAITVDVEVASDTPHPARIGLNCQLAQVAERVNWLGLGPQ
ENYPDRLTAACFDRWDLPLSDMYTPYVFPSENGLRCGTRELNYGP
HQWRGDFQFNISRYSQQQLMETSHRHLLHAEEGTWLNIDGFHMGI
GGDDSWSPSVSAEFQLSAGRYHYQLVWCQKLEHHHHHH
```

Construct 9
C*-CAT (SEQ ID NO: 17)
```
ATGATCAAAATAGCCACACGTAAATATTTAGGCAAACAAAATGTC
TATGGCATTGGAGTTGAGCGCGACCATAATTTTGCACTCAAAAAT
GGCTTCATAGCTTCTAATTGTTTCAATGCTAGCATGGAGAAAAAA
ATCACTGGATATACCACCGTTGATATATCCCAATGGCATCGTAAA
GAACATTTTGAGGCATTTCAGTCAGTTGCTCAATGTACCTATAAC
CAGACCGTTCAGCTGGATATTACGGCCTTTTTAAAGACCGTAAAG
AAAAATAAGCACAAGTTTTATCCGGCCTTTATTCACATTCTTGCC
CGCCTGATGAATGCTCATCCGGAATTTCGTATGGCAATGAAAGAC
GGTGAGCTGGTGATATGGGATAGTGTTCACCCTTGTTACACCGTT
TTCCATGAGCAAACTGAAACGTTTTCATCGCTCTGGAGTGAATAC
CACGACGATTTCCGGCAGTTTCTACACATATATTCGCAAGATGTG
GCGTGTTACGGTGAAAACCTGGCCTATTTCCCTAAAGGGTTTATT
GAGAATATGTTTTTCGTCTCAGCCAATCCCTGGGTGAGTTTCACC
AGTTTTGATTTAAACGTGGCCAATATGGACAACTTCTTCGCCCCC
GTTTTCACCATGGGCAAATATTATACGCAAGGCGACAAGGTGCTG
ATGCCGCTGGCGATTCAGGTTCATCATGCCGTCTGTGATGGCTTC
CATGTCGGCAGAATGCTTAATGAATTACAACAGTACTGCGATGAG
TGGCAGGGCGGGGCGCTCGAGCACCACCACCACCACCAC
```

Translated C*-CAT:

(SEQ ID NO: 18)
```
MIKIATRKYLGKQNVYGIGVERDHNFALKNGFIASNCFNASMEKK
ITGYTTVDISQWHRKEHFEAFQSVAQCTYNQTVQLDITAFLKTVK
KNKHKFYPAFIHILARLMNAHPEFRMAMKDGELVIWDSVHPCYTV
FHEQTETFSSLWSEYHDDFRQFLHIYSQDVACYGENLAYFPKGFI
ENMFFVSANPWVSFTSFDLNVANMDNFFAPVFTMGKYYTQGDKVL
MPLAIQVHHAVCDGFHVGRMLNELQQYCDEWQGGALEHHHHHH
```

Construct 10
C*-MBP (SEQ ID NO: 19)
```
ATGATCAAAATAGCCACACGTAAATATTTAGGCAAACAAAATGTC
TATGGCATTGGAGTTGAGCGCGACCATAATTTTGCACTCAAAAAT
GGCTTCATAGCTTCTAATTGTTTCAATGCTAGCATGAAAATCGAA
GAAGGTAAACTGGTAATCTGGATTAACGGCGATAAAGGCTATAAC
GGTCTCGCTGAAGTCGGTAAGAAATTCGAGAAAGATACCGGAATT
AAAGTCACCGTTGAGCATCCGGATAAACTGGAAGAGAAATTCCCA
CAGGTTGCGGCAACTGGCGATGGCCCTGACATTATCTTCTGGGCA
CACGACCGCTTTGGTGGCTACGCTCAATCTGGCCTGTTGGCTGAA
ATCACCCCGGACAAAGCGTTCCAGGACAAGCTGTATCCGTTTACC
TGGGATGCCGTACGTTACAACGGCAAGCTGATTGCTTACCCGATC
GCTGTTGAAGCGTTATCGCTGATTTATAACAAAGATCTGCTGCCG
AACCCGCCAAAAACCTGGGAAGAGATCCCGGCGCTGGATAAAGAA
CTGAAAGCGAAAGGTAAGAGCGCGCTGATGTTCAACCTGCAAGAA
CCGTACTTCACCTGGCCGCTGATTGCTGCTGACGGGGGTTATGCG
TTCAAGTATGAAAACGGCAAGTACGACATTAAAGACGTGGGCGTG
GATAACGCTGGCGCGAAAGCGGGTCTGACCTTCCTGGTTGACCTG
ATTAAAAACAAACACATGAATGCAGACACCGATTACTCCATCGCA
GAAGCTGCCTTTAATAAAGGCGAAACAGCGATGACCATCAACGGC
CCGTGGGCATGGTCCAACATCGACACCAGCAAAGTGAATTATGGT
GTAACGGTACTGCCGACCTTCAAGGGTCAACCATCCAAACCGTTC
GTTGGCGTGCTGAGCGCAGGTATTAACGCCGCCAGTCCGAACAAA
GAGCTGGCAAAAGAGTTCCTCGAAAACTATCTGCTGACTGATGAA
GGTCTGGAAGCGGTTAATAAAGACAAACCGCTGGGTGCCGTAGCG
CTGAAGTCTTACGAGGAAGAGTTGGCGAAAGATCCACGTATTGCC
GCCACCATGGAAAACGCCCAGAAAGGTGAAATCATGCCGAACATC
CCGCAGATGTCCGCTTTCTGGTATGCCGTGCGTACTGCGGTGATC
AACGCCGCCAGCGGTCGTCAGACTGTCGATGAAGCCCTGAAAGAC
GCGCAGACTAATTCGAGCTCGAACAACAACAACAATAACAATAAC
AACAACCTCGGGATCGAGGGAAGGGGACTCGAGCACCACCACCAC
CACCAC
```

C*-MBP translated:

(SEQ ID NO: 20)
```
MIKIATRKYLGKQNVYGIGVERDHNFALKNGFIASNCFNASMKIE
EGKLVIWINGDKGYNGLAEVGKKFEKDTGIKVTVEHPDKLEEKFP
QVAATGDGPDIIFWAHDRFGGYAQSGLLAEITPDKAFQDKLYPFT
WDAVRYNGKLIAYPIAVEALSLIYNKDLLPNPPKTWEEIPALDKE
LKAKGKSALMFNLQEPYFTWPLIAADGGYAFKYENGKYDIKDVGV
DNAGAKAGLTFLVDLIKNKHMNADTDYSIAEAAFNKGETAMTING
PWAWSNIDTSKVNYGVTVLPTFKGQPSKPFVGVLSAGINAASPNK
ELAKEFLENYLLTDEGLEAVNKDKPLGAVALKSYEEELAKDPRIA
ATMENAQKGEIMPNIPQMSAFWYAVRTAVINAASGRQTVDEALKD
AQTNSSSNNNNNNNNNNLGIEGRGLEHHHHHH
```

Construct 11
N-CBD:
(SEQ ID NO: 21)
ATGTGTTTAAGCTATGAAACGGAAATATTGACAGTAGAATATGGA

TTATTACCGATTGGTAAAATTGTAGAAAAGCGCATCGAATGTACT

GTTTATAGCGTTGATAATAATGGAAATATTTATACACAACCTGTA

GCACAATGGCACGATCGCGGAGAACAAGAGGTGTTTGAGTATTGT

TTGGAAGATGGTTCATTGATTCGGGCAACAAAAGACCATAAGTTT

ATGACTGTTGATGGTCAAATGTTGCCAATTGATGAAATATTTGAA

CGTGAATTGGATTTGATGCGGGTTGATAATTTGCCGAATAAGCTT

GGAGGCGGAGGGAGCGGAGGCGGAGGGAGCGCTAGCATGAAAATC

GAAGAAGGTAAACTGACAAATCCTGGTGTATCCGCTTGGCAGGTC

AACACAGCTTATACTGCGGGACAATTGGTCACATATAACGGCAAG

ACGTATAAATGTTTGCAGCCCCACACCTCCTTGGCAGGATGGGAA

CCATCCAACGTTCCTGCCTTGTGGCAGCTTCAACTCGAGCACCAC

CACCACCACCACTGA

N-CBD Translated:
(SEQ ID NO: 22)
MCLSYETEILTVEYGLLPIGKIVEKRIECTVYSVDNNGNIYTQPV

AQWHDRGEQEVFEYCLEDGSLIRATKDHKFMTVDGQMLPIDEIFE

RELDLMRVDNLPNKLGGGSGGGGSASMKIEEGKLTNPGVSAWQV

NTAYTAGQLVTYNGKTYKCLQPHTSLAGWEPSNVPALWQLQLEHH

HHHH

Construct 12
NC1A-CBD:
(SEQ ID NO: 23)
ATGGCTTTAAGCTATGAAACGGAAATATTGACAGTAGAATATGGA

TTATTACCGATTGGTAAAATTGTAGAAAAGCGCATCGAATGTACT

GTTTATAGCGTTGATAATAATGGAAATATTTATACACAACCTGTA

GCACAATGGCACGATCGCGGAGAACAAGAGGTGTTTGAGTATTGT

TTGGAAGATGGTTCATTGATTCGGGCAACAAAAGACCATAAGTTT

ATGACTGTTGATGGTCAAATGTTGCCAATTGATGAAATATTTGAA

CGTGAATTGGATTTGATGCGGGTTGATAATTTGCCGAATAAGCTT

GGAGGCGGAGGGAGCGGAGGCGGAGGGAGCGCTAGCATGAAAATC

GAAGAAGGTAAACTGACAAATCCTGGTGTATCCGCTTGGCAGGTC

AACACAGCTTATACTGCGGGACAATTGGTCACATATAACGGCAAG

ACGTATAAATGTTTGCAGCCCCACACCTCCTTGGCAGGATGGGAA

CCATCCAACGTTCCTGCCTTGTGGCAGCTTCAACTCGAGCACCAC

CACCACCACCACTGA

NC1A-CBD Translated:
(SEQ ID NO: 24)
MALSYETEILTVEYGLLPIGKIVEKRIECTVYSVDNNGNIYTQPV

AQWHDRGEQEVFEYCLEDGSLIRATKDHKFMTVDGQMLPIDEIFE

RELDLMRVDNLPNKLGGGSGGGGSASMKIEEGKLTNPGVSAWQV

NTAYTAGQLVTYNGKTYKCLQPHTSLAGWEPSNVPALWQLQLEHH

HHHH

Construct 13
C-PTDH:
(SEQ ID NO: 25)
ATGATCAAAATAGCCACACGTAAATATTTAGGCAAACAAAATGTC

TATGACATTGGAGTTGAGCGCGACCATAATTTTGCACTCAAAAAT

GGCTTCATAGCTTCTAATTGTTTCAATGCTAGCATGCTGCCGAAA

CTCGTTATAACTCACCGAGTACACGAAGAGATCCTGCAACTGCTG

GCGCCACATTGCGAGCTGATAACCAACCAGACCGACAGCACGCTG

ACGCGCGAGGAAATTCTGCGCCGCTGTCGCGATGCTCAGGCGATG

ATGGCGTTCATGCCCGATCGGGTCGATGCAGACTTTCTTCAAGCC

TGCCCTGAGCTGCGTGTAATCGGCTGCGCGCTCAAGGGCTTCGAC

AATTTCGATGTGGACGCCTGTACTGCCCGCGGGGTCTGGCTGACC

TTCGTGCCTGATCTGTTGACGGTCCCGACTGCCGAGCTGGCGATC

GGACTGGCGGTGGGGCTGGGGCGGCATCTGCGGGCAGCAGATGCG

TTCGTCCGCTCTGGCAAGTTCCGGGGCTGGCAACCACGGTTCTAC

GGCACGGGGCTGGATAACGCTACGGTCGGCTTCCTTGGCATGGGC

GCCATCGGACTGGCCATGGCTGATCGCTTGCAGGGATGGGGCGCG

ACCCTGCAGTACCACGCGCGGAAGGCTCTGGATACACAAACCGAG

CAACGGCTCGGCCTGCGCCAGGTGGCGTGCAGCGAACTCTTCGCC

AGCTCGGACTTCATCCTGCTGGCGCTTCCCTTGAATGCCGATACC

CTGCATCTGGTCAACGCCGAGCTGCTTGCCCTCGTACGGCCGGGC

GCTCTGCTTGTAAACCCCTGTCGTGGCTCGGTAGTGGATGAAGCC

GCCGTGCTCGCGGCGCTTGAGCGAGGCCAGCTCGGCGGGTATGCG

GCGGATGTATTCGAAATGGAAGACTGGGCTCGCGCGGACCGGCCG

CAGCAGATCGATCCTGCGCTGCTCGCGCATCCGAATACGCTGTTC

ACTCCGCACATAGGGTCGGCAGTGCGCGCGGTGCGCCTGGAGATT

GAACGTTGTGCAGCGCAGAACATCCTCCAGGCATTGGCAGGTGAG

CGCCCAATCAACGCTGTGAACCGTCTGCCCAAGGCCAATCCTGCC

GCAGACCTCGAGCACCACCACCACCACCAC

C-PTDH Translated:
(SEQ ID NO: 26)
MIKIATRKYLGKQNVYDIGVERDHNFALKNGFIASNCFNASMLPK

LVITHRVHEEILQLLAPHCELITNQTDSTLTREEILRRCRDAQAM

MAFMPDRVDADFLQACPELRVIGCALKGFDNFDVDACTARGVWLT

FVPDLLTVPTAELAIGLAVGLGRHLRAADAFVRSGKFRGWQPRFY

GTGLDNATVGFLGMGAIGLAMADRLQGWGATLQYHARKALDTQTE

QRLGLRQVACSELFASSDFILLALPLNADTLHLVNAELLALVRPG

ALLVNPCRGSVVDEAAVLAALERGQLGGYAADVFEMEDWARADRP

QQIDPALLAHPNTLFTPHIGSAVRAVRLEIERCAAQNILQALAGE

RPINAVNRLPKANPAADLEHHHHHH

Construct 14
C*-A-GFP:
(SEQ ID NO: 27)
ATGATCAAAATAGCCACACGTAAATATTTAGGCAAACAAAATGTC -continued
TATGGCATTGGAGTTGAGCGCGACCATAATTTTGCACTCAAAAAT
GGCTTCATAGCTTCTAATGCGTTCAATGTGAGCAAGGGCGAGGAG
CTGTTCACCGGGGTGGTGCCCATCCTGGTCGAGCTGGACGGCGAC
GTAAACGGCCACAAGTTCAGCGTGTCCGGCGAGGGCGAGGGCGAT
GCCACCTACGGCAAGCTGACCCTGAAGTTCATCTGCACCACCGGC
AAGCTGCCCGTGCCCTGGCCCACCCTCGTGACCACCCTGACCTAC
GGCGTGCAGTGCTTCAGCCGCTACCCCGACCACATGAAGCAGCAC
GACTTCTTCAAGTCCGCCATGCCCGAAGGCTACGTCCAGGAGCGC
ACCATCTTCTTCAAGGACGACGGCAACTACAAGACCCGCGCCGAG
GTGAAGTTCGAGGGCGACACCCTGGTGAACCGCATCGAGCTGAAG
GGCATCGACTTCAAGGAGGACGGCAACATCCTGGGGCACAAGCTG
GAGTACAACTACAACAGCCACAACGTCTATATCATGGCCGACAAG
CAGAAGAACGGCATCAAGGTGAACTTCAAGATCCGCCACAACATC
GAGGACGGCAGCGTGCAGCTCGCCGACCACTACCAGCAGAACACC
CCCATCGGCGACGGCCCCGTGCTGCTGCCCGACAACCACTACCTG
AGCACCCAGTCCGCCCTGAGCAAAGACCCCAACGAGAAGCGCGAT
CACATGGTCCTGCTGGAGTTCGTGACCGCCGCCGGGATCACTCTC
GGCATGGACGAGTTACTCGAGCACCACCACCACCACCAC C*-A-GFP Translated:
(SEQ ID NO: 28)
MIKIATRKYLGKQNVYGIGVERDHNFALKNGFIASNAFNVSKGEE
LFTGVVPILVELDGDVNGHKFSVSGEGEGDATYGKLTLKFICTTG
KLPVPWPTLVTTLTYGVQCFSRYPDHMKQHDFFKSAMPEGYVQER
TIFFKDDGNYKTRAEVKFEGDTLVNRIELKGIDFKEDGNILGHKL
EYNYNSHNVYIMADKQKNGIKVNFKIRHNIEDGSVQLADHYQQNT
PIGDGPVLLPDNHYLSTQSALSKDPNEKRDHMVLLEFVTAAGITL
GMDELLEHHHHHH Construct 15
C*-D-GFP:
(SEQ ID NO: 29)
ATGATCAAAATAGCCACACGTAAATATTTAGGCAAACAAAATGTC
TATGGCATTGGAGTTGAGCGCGACCATAATTTTGCACTCAAAAAT
GGCTTCATAGCTTCTAATGATTTCAATGTGAGCAAGGGCGAGGAG
CTGTTCACCGGGGTGGTGCCCATCCTGGTCGAGCTGGACGGCGAC
GTAAACGGCCACAAGTTCAGCGTGTCCGGCGAGGGCGAGGGCGAT
GCCACCTACGGCAAGCTGACCCTGAAGTTCATCTGCACCACCGGC
AAGCTGCCCGTGCCCTGGCCCACCCTCGTGACCACCCTGACCTAC
GGCGTGCAGTGCTTCAGCCGCTACCCCGACCACATGAAGCAGCAC
GACTTCTTCAAGTCCGCCATGCCCGAAGGCTACGTCCAGGAGCGC
ACCATCTTCTTCAAGGACGACGGCAACTACAAGACCCGCGCCGAG
GTGAAGTTCGAGGGCGACACCCTGGTGAACCGCATCGAGCTGAAG
GGCATCGACTTCAAGGAGGACGGCAACATCCTGGGGCACAAGCTG
GAGTACAACTACAACAGCCACAACGTCTATATCATGGCCGACAAG CAGAAGAACGGCATCAAGGTGAACTTCAAGATCCGCCACAACATC
GAGGACGGCAGCGTGCAGCTCGCCGACCACTACCAGCAGAACACC
CCCATCGGCGACGGCCCCGTGCTGCTGCCCGACAACCACTACCTG
AGCACCCAGTCCGCCCTGAGCAAAGACCCCAACGAGAAGCGCGAT
CACATGGTCCTGCTGGAGTTCGTGACCGCCGCCGGGATCACTCTC
GGCATGGACGAGTTACTCGAGCACCACCACCACCACCAC C*-D-GFP Translated:
(SEQ ID NO: 30)
MIKIATRKYLGKQNVYGIGVERDHNFALKNGFIASNDFNVSKGEE
LFTGVVPILVELDGDVNGHKFSVSGEGEGDATYGKLTLKFICTTG
KLPVPWPTLVTTLTYGVQCFSRYPDHMKQHDFFKSAMPEGYVQER
TIFFKDDGNYKTRAEVKFEGDTLVNRIELKGIDFKEDGNILGHKL
EYNYNSHNVYIMADKQKNGIKVNFKIRHNIEDGSVQLADHYQQNT
PIGDGPVLLPDNHYLSTQSALSKDPNEKRDHMVLLEFVTAAGITL
GMDELLEHHHHHH Construct 16
C*-L-GFP:
(SEQ ID NO: 31)
ATGATCAAAATAGCCACACGTAAATATTTAGGCAAACAAAATGTC
TATGGCATTGGAGTTGAGCGCGACCATAATTTTGCACTCAAAAAT
GGCTTCATAGCTTCTAATCTGTTCAATGTGAGCAAGGGCGAGGAG
CTGTTCACCGGGGTGGTGCCCATCCTGGTCGAGCTGGACGGCGAC
GTAAACGGCCACAAGTTCAGCGTGTCCGGCGAGGGCGAGGGCGAT
GCCACCTACGGCAAGCTGACCCTGAAGTTCATCTGCACCACCGGC
AAGCTGCCCGTGCCCTGGCCCACCCTCGTGACCACCCTGACCTAC
GGCGTGCAGTGCTTCAGCCGCTACCCCGACCACATGAAGCAGCAC
GACTTCTTCAAGTCCGCCATGCCCGAAGGCTACGTCCAGGAGCGC
ACCATCTTCTTCAAGGACGACGGCAACTACAAGACCCGCGCCGAG
GTGAAGTTCGAGGGCGACACCCTGGTGAACCGCATCGAGCTGAAG
GGCATCGACTTCAAGGAGGACGGCAACATCCTGGGGCACAAGCTG
GAGTACAACTACAACAGCCACAACGTCTATATCATGGCCGACAAG
CAGAAGAACGGCATCAAGGTGAACTTCAAGATCCGCCACAACATC
GAGGACGGCAGCGTGCAGCTCGCCGACCACTACCAGCAGAACACC
CCCATCGGCGACGGCCCCGTGCTGCTGCCCGACAACCACTACCTG
AGCACCCAGTCCGCCCTGAGCAAAGACCCCAACGAGAAGCGCGAT
CACATGGTCCTGCTGGAGTTCGTGACCGCCGCCGGGATCACTCTC
GGCATGGACGAGTTACTCGAGCACCACCACCACCACCAC C*-L-GFP Translated:
(SEQ ID NO: 32)
MIKIATRKYLGKQNVYGIGVERDHNFALKNGFIASNLFNVSKGEE
LFTGVVPILVELDGDVNGHKFSVSGEGEGDATYGKLTLKFICTTG
KLPVPWPTLVTTLTYGVQCFSRYPDHMKQHDFFKSAMPEGYVQER
TIFFKDDGNYKTRAEVKFEGDTLVNRIELKGIDFKEDGNILGHKL
EYNYNSHNVYIMADKQKNGIKVNFKIRHNIEDGSVQLADHYQQNT Construct 17
C*-P-GFP:
(SEQ ID NO: 33)
ATGATCAAAATAGCCACACGTAAATATTTAGGCAAACAAAATGTC
TATGGCATTGGAGTTGAGCGCGACCATAATTTTGCACTCAAAAAT
GGCTTCATAGCTTCTAATCCGTTCAATGTGAGCAAGGGCGAGGAG
CTGTTCACCGGGGTGGTGCCCATCCTGGTCGAGCTGGACGGCGAC
GTAAACGGCCACAAGTTCAGCGTGTCCGGCGAGGGCGAGGGCGAT
GCCACCTACGGCAAGCTGACCCTGAAGTTCATCTGCACCACCGGC
AAGCTGCCCGTGCCCTGGCCCACCCTCGTGACCACCCTGACCTAC
GGCGTGCAGTGCTTCAGCCGCTACCCCGACCACATGAAGCAGCAC
GACTTCTTCAAGTCCGCCATGCCCGAAGGCTACGTCCAGGAGCGC
ACCATCTTCTTCAAGGACGACGGCAACTACAAGACCCGCGCCGAG
GTGAAGTTCGAGGGCGACACCCTGGTGAACCGCATCGAGCTGAAG
GGCATCGACTTCAAGGAGGACGGCAACATCCTGGGGCACAAGCTG
GAGTACAACTACAACAGCCACAACGTCTATATCATGGCCGACAAG
CAGAAGAACGGCATCAAGGTGAACTTCAAGATCCGCCACAACATC
GAGGACGGCAGCGTGCAGCTCGCCGACCACTACCAGCAGAACACC
CCCATCGGCGACGGCCCCGTGCTGCTGCCCGACAACCACTACCTG
AGCACCCAGTCCGCCCTGAGCAAAGACCCCAACGAGAAGCGCGAT
CACATGGTCCTGCTGGAGTTCGTGACCGCCGCCGGGATCACTCTC
GGCATGGACGAGTTACTCGAGCACCACCACCACCACCAC C*-P-GFP Translated:
(SEQ ID NO: 34)
MIKIATRKYLGKQNVYGIGVERDHNFALKNGFIASNPFNVSKGEE
LFTGVVPILVELDGDVNGHKFSVSGEGEGDATYGKLTLKFICTTG
KLPVPWPTLVTTLTYGVQCFSRYPDHMKQHDFFKSAMPEGYVQER
TIFFKDDGNYKTRAEVKFEGDTLVNRIELKGIDFKEDGNILGHKL
EYNYNSHNVYIMADKQKNGIKVNFKIRHNIEDGSVQLADHYQQNT
PIGDGPVLLPDNHYLSTQSALSKDPNEKRDHMVLLEFVTAAGITL
GMDELLEHHHHHH Construct 18
C*-R-GFP:
(SEQ ID NO: 35)
ATGATCAAAATAGCCACACGTAAATATTTAGGCAAACAAAATGTC
TATGGCATTGGAGTTGAGCGCGACCATAATTTTGCACTCAAAAAT
GGCTTCATAGCTTCTAATCGTTTCAATGTGAGCAAGGGCGAGGAG
CTGTTCACCGGGGTGGTGCCCATCCTGGTCGAGCTGGACGGCGAC
GTAAACGGCCACAAGTTCAGCGTGTCCGGCGAGGGCGAGGGCGAT
GCCACCTACGGCAAGCTGACCCTGAAGTTCATCTGCACCACCGGC
AAGCTGCCCGTGCCCTGGCCCACCCTCGTGACCACCCTGACCTAC
GGCGTGCAGTGCTTCAGCCGCTACCCCGACCACATGAAGCAGCAC
GACTTCTTCAAGTCCGCCATGCCCGAAGGCTACGTCCAGGAGCGC
ACCATCTTCTTCAAGGACGACGGCAACTACAAGACCCGCGCCGAG
GTGAAGTTCGAGGGCGACACCCTGGTGAACCGCATCGAGCTGAAG
GGCATCGACTTCAAGGAGGACGGCAACATCCTGGGGCACAAGCTG
GAGTACAACTACAACAGCCACAACGTCTATATCATGGCCGACAAG
CAGAAGAACGGCATCAAGGTGAACTTCAAGATCCGCCACAACATC
GAGGACGGCAGCGTGCAGCTCGCCGACCACTACCAGCAGAACACC
CCCATCGGCGACGGCCCCGTGCTGCTGCCCGACAACCACTACCTG
AGCACCCAGTCCGCCCTGAGCAAAGACCCCAACGAGAAGCGCGAT
CACATGGTCCTGCTGGAGTTCGTGACCGCCGCCGGGATCACTCTC
GGCATGGACGAGTTACTCGAGCACCACCACCACCACCAC C*-R-GFP Translated:
(SEQ ID NO: 36)
MIKIATRKYLGKQNVYGIGVERDHNFALKNGFIASNRFNVSKGEE
LFTGVVPILVELDGDVNGHKFSVSGEGEGDATYGKLTLKFICTTG
KLPVPWPTLVTTLTYGVQCFSRYPDHMKQHDFFKSAMPEGYVQER
TIFFKDDGNYKTRAEVKFEGDTLVNRIELKGIDFKEDGNILGHKL
EYNYNSHNVYIMADKQKNGIKVNFKIRHNIEDGSVQLADHYQQNT
PIGDGPVLLPDNHYLSTQSALSKDPNEKRDHMVLLEFVTAAGITL
GMDELLEHHHHHH C*-Translated:
(SEQ ID NO: 37)
MIKIATRKYLGKQNVYGIGVERDHNFALKNGFIASN aa sequence of ELP:
(SEQ ID NO: 38)
MGHGVGVPGVGVPGGGVPGAGVPGVGVPGVGVPGVGVPGGGVPGA
GVPGGGVPGVGVPGVGVPGGGVPGAGVPGVGVPGVGVPGVGVPGG
GVPGAGVPGGGVPGVGVPGVGVPGGGVPGAGVPGVGVPGVGVPGV
GVPGGGVPGAGVPGGGVPGVGVPGVGVPGGGVPGAGVPGVGVPGV
GVPGVGVPGGGVPGAGVPGGGVPGVGVPGVGVPGGGVPGAGVPGV
GVPGVGVPGVGVPGGGVPGAGVPGGGVPGVGVPGVGVPGGGVPGA
GVPGVGVPGVGVPGVGVPGGGVPGAGVPGGGVPGVGVPGVGVPGG
GVPGAGVPGVGVPGVGVPGVGVPGGGVPGAGVPGGGVPGVGVPGV
GVPGGGVPGAGVPGVGVPGVGVPGVGVPGGGVPGAGVPGGGVPGV
GVPGVGVPGGGVPGAGVPGVGVPGVGVPGVGVPGGGVPGAGVPGG
GVPGVGVPGVGVPGGGVPGAGVPGVGVPGVGVPGVGVPGVGVPGG
GVPGAGVPGGGVPGGLVSSNNNNNNNNNNNNLGIEGRISEF aa sequence of intein N-fragment:
(SEQ ID NO: 39)
ALSYETEILTVEYGLLPIGKIVEKRIECTVYSVDNNGNIYTQPVA
QWHDRGEQEVFEYCLEDGSLIRATKDHKFMTVDGQMLPIDEIFER
ELDLMRVDNLPN

C*-DNA:
(SEQ ID NO: 40)
ATGATCAAAATAGCCACACGTAAATATTTAGGCAAACAAAATGTC

TATGGCATTGGAGTTGAGCGCGACCATAATTTTGCACTCAAAAAT

GGCTTCATAGCTTCTAAT

ELP-intein N-fragment:
(SEQ ID NO: 41)
ATGGGCCACGGCGTGGGTGTTCCGGGCGTGGGTGTTCCGGGTGGC

GGTGTGCCGGGCGCAGGTGTTCCTGGTGTAGGTGTGCCGGGTGTT

GGTGTGCCGGGTGTTGGTGTACCAGGTGGCGGTGTTCCGGGTGCA

GGCGTTCCGGGTGGCGGTGTGCCGGGCGTGGGTGTTCCGGGCGTG

GGTGTTCCGGGTGGCGGTGTGCCGGGCGCAGGTGTTCCTGGTGTA

GGTGTGCCGGGTGTTGGTGTGCCGGGTGTTGGTGTACCAGGTGGC

GGTGTTCCGGGTGCAGGCGTTCCGGGTGGCGGTGTGCCGGGCGTG

GGTGTTCCGGGCGTGGGTGTTCCGGGTGGCGGTGTGCCGGGCGCA

GGTGTTCCTGGTGTAGGTGTGCCGGGTGTTGGTGTGCCGGGTGTT

GGTGTACCAGGTGGCGGTGTTCCGGGTGCAGGCGTTCCGGGTGGC

GGTGTGCCGGGCGTGGGTGTTCCGGGCGTGGGTGTTCCGGGTGGC

GGTGTGCCGGGCGCAGGTGTTCCTGGTGTAGGTGTGCCGGGTGTT

GGTGTGCCGGGTGTTGGTGTACCAGGTGGCGGTGTTCCGGGTGCA

GGCGTTCCGGGTGGCGGTGTGCCGGGCGTGGGTGTTCCGGGCGTG

GGTGTTCCGGGTGGCGGTGTGCCGGGCGCAGGTGTTCCTGGTGTA

GGTGTGCCGGGTGTTGGTGTGCCGGGTGTTGGTGTACCAGGTGGC

GGTGTTCCGGGTGCAGGCGTTCCGGGTGGCGGTGTGCCGGGCGTG

GGTGTTCCGGGCGTGGGTGTTCCGGGTGGCGGTGTGCCGGGCGCA

GGTGTTCCTGGTGTAGGTGTGCCGGGTGTTGGTGTGCCGGGTGTT

GGTGTACCAGGTGGCGGTGTTCCGGGTGCAGGCGTTCCGGGTGGC

GGTGTGCCGGGCGTGGGTGTTCCGGGCGTGGGTGTTCCGGGTGGC

GGTGTGCCGGGCGCAGGTGTTCCTGGTGTAGGTGTGCCGGGTGTT

GGTGTGCCGGGTGTTGGTGTACCAGGTGGCGGTGTTCCGGGTGCA

GGCGTTCCGGGTGGCGGTGTGCCGGGCGTGGGTGTTCCGGGCGTG

GGTGTTCCGGGTGGCGGTGTGCCGGGCGCAGGTGTTCCTGGTGTA

GGTGTGCCGGGTGTTGGTGTGCCGGGTGTTGGTGTACCAGGTGGC

GGTGTTCCGGGTGCAGGCGTTCCGGGTGGCGGTGTGCCGGGCGGG

CTGGTGAGCTCGAACAACAACAACAATAACAATAACAACAACCTC

GGGATCGAGGGAAGGATTTCAGAATTCGGAGGCGGAGGGAGCGGA

GGCGGAGGGAGCGCTAGCTGTTTAAGCTATGAAACGGAAATATTG

ACAGTAGAATATGGATTATTACCGATTGGTAAAATTGTAGAAAAG

CGCATCGAATGTACTGTTTATAGCGTTGATAATAATGGAAATATT

TATACACAACCTGTAGCACAATGGCACGATCGCGGAGAACAAGAG

GTGTTTGAGTATTGTTTGGAAGATGGTTCATTGATTCGGGCAACA

AAAGACCATAAGTTTATGACTGTTGATGGTCAAATGTTGCCAATT

GATGAAATATTTGAACGTGAATTGGATTTGATGCGGGTTGATAAT

TTGCCGAATCTCGAGCACCACCACCACCACCAC.

ELP intein N-fragment translated:
(SEQ ID NO: 42)
MGHGVGVPGVGVPGGGVPGAGVPGVGVPGVGVPGVGVPGGGVPGA

GVPGGGVPGVGVPGVGVPGGGVPGAGVPGVGVPGVGVPGVGVPGG

GVPGAGVPGGGVPGVGVPGVGVPGGGVPGAGVPGVGVPGVGVPGV

GVPGGGVPGAGVPGGGVPGVGVPGVGVPGGGVPGAGVPGVGVPGV

GVPGVGVPGGGVPGAGVPGGGVPGVGVPGVGVPGGGVPGAGVPGV

GVPGVGVPGVGVPGGGVPGAGVPGGGVPGVGVPGVGVPGGGVPGA

GVPGVGVPGVGVPGVGVPGGGVPGAGVPGGGVPGVGVPGVGVPGG

GVPGAGVPGVGVPGVGVPGVGVPGGGVPGAGVPGGGVPGVGVPGV

GVPGGGVPGAGVPGVGVPGVGVPGVGVPGGGVPGAGVPGGGVPGV

GVPGVGVPGGGVPGAGVPGVGVPGVGVPGVGVPGGGVPGAGVPGG

GVPGVGVPGVGVPGGGVPGAGVPGVGVPGVGVPGVGVPGGGVPGA

GVPGGGVPGVGVPGVGVPGGGVPGAGVPGVGVPGVGVPGVGVPGG

GVPGAGVPGGGVPGGLVSSNNNNNNNNNNNLGIEGRISEFGGGGSG

GGGSASCLSYETEILTVEYGLLPIGKIVEKRIECTVYSVDNNGNI

YTQPVAQWHDRGEQEVFEYCLEDGSLIRATKDHKFMTVDGQMLPI

DEIFERELDLMRVDNLPNLEHHHHHH

Primers used in this study:
NPUC_F_NDEI 104:
(SEQ ID NO: 43)
TTAGAAGGCATATGATCAAAATAGCCACACGTAAATATTTAGG.

OXP-NC-G-REV:
(SEQ ID NO: 44)
CCTCGCCCTTGCTCACATTGAAACAATTAGAAGCTATGAAGCCAT.

OXP-GFP-NC-FWD:
(SEQ ID NO: 45)
ATAGCTTCTAATTGTTTCAATGTGAGCAAGGGCGAGG.

XHOI_GFP_R:
(SEQ ID NO: 46)
TAAAATCTCGAGTAACTCGTCCATGCCGAGAG.

NPUCD17G-F:
(SEQ ID NO: 47)
GGCAAACAAAATGTCTATGGCATTGGAGTT.

NPUCD17G-R:
(SEQ ID NO: 48)
GTCGCGCTCAACTCCAATGCCATAGACATT.

HINDIII-LINK-NPU F:
(SEQ ID NO: 49)
CCTGGAAGCTTGTGGAGGCGGAGGGAGCGGAGGCGGAGGGAGCGC

```
NPUN_R_XHOI:
                                                        (SEQ ID NO: 50)
ATATAGCTCGAGATTCGGCAAATTATCAACCCG.

NDEI-CBD-F:
                                                        (SEQ ID NO: 51)
TAATTTAACATATGAAAATCGAAGAAGGTAAACTGACAAATCCT.

HINDIII-CBD-R:
                                                        (SEQ ID NO: 52)
AAGATTAAAGCTTCTTGAAGCTGCCACAAGGCA.

NHEI-C1A-F:
                                                        (SEQ ID NO: 53)
AATTAAGCTAGCGCCTTAAGCTATGAAACGGAAATATTGACA.

ECORI-LINKER-NPUN F:
                                                        (SEQ ID NO: 54)
AATATGGGAATTCGGAGGCGGAGGGAGCGG.

HINDIII-6H-NUPN-R:
                                                        (SEQ ID NO: 55)
GTACATTAAGCTTAGCAGCCGGATCTCAGT.

NHEI-NPUC CFN-R:
                                                        (SEQ ID NO: 56)
ATTCGCGCTAGCATTGAAACAATTAGAAGCTATGAAGCC.

XHOI_DSRED_R:
                                                        (SEQ ID NO: 57)
TAAAATCTCGAGCAGGAACAGGTGGTGGC.

HINDII-L-DSRED-FWD:
                                                        (SEQ ID NO: 58)
TTCAATAAGCTTGGAGGCGGAGGGAGCGGAGGCGGAGGGAGCGCT
AGCGCCTCCTCCGAGGACG.

NHEI-PTDH-F:
                                                        (SEQ ID NO: 59)
ATTTAACGCTAGCATGCTGCCGAAACTCGTTATAACTC.

XHOI-PTDH12X-R:
                                                        (SEQ ID NO: 60)
AGTTTAGCTCGAGGTCTGCGGCAGGATTGG.

NHEI-LACZ-F:
                                                        (SEQ ID NO: 61)
ATTTCAATGCTAGCATGACCATGATTACGGATTCACT.

XHOI-LACZ-R:
                                                        (SEQ ID NO: 62)
TGATAATCTCGAGTTTTTGACACCAGACCAACTG.

NHEI-CAT-F:
                                                        (SEQ ID NO: 63)
GTTTCAATGCTAGCATGGAGAAAAAAATCACTGGATATACCACCG
TTGATATAT.

XHOI-CAT-R:
                                                        (SEQ ID NO: 64)
TAATAATTAACTCGAGCGCCCCGCCCTGCCAC.

NHEI-MBP-F:
                                                        (SEQ ID NO: 65)
GTTTCAATGCTAGCATGAAAATCGAAGAAGGTAAACTGGTAATCT.

XHOI-MBP-R:
                                                        (SEQ ID NO: 66)
AAGTTATACTCGAGTCCCCTTCCCTCGATCC.
```

What is claimed is:

1. A method of purifying a protein of interest (POI) comprising:
   contacting a first fusion protein comprising the POI fused to the C-terminus of an intein C-fragment with a second fusion protein comprising an intein N-fragment and a purification tag to form a complex between the first fusion protein and the second fusion protein, wherein a mutation is introduced into the C-intein fragment at Asp118Gly as aligned in FIG. 24A;
   cleaving the POI from the intein C-fragment, wherein the POI is released from the complex, wherein over 85% C-terminal cleavage is achieved within 30 minutes; and
   isolating the POI, wherein the intein is a split intein or a naturally split intein and wherein the effect of the mutation is at least one of: decreases N-terminal cleavage, suppresses trans-splicing ability, or increases C-terminal cleavage rate and efficiency, compared to a non-mutated intein C-fragment, and wherein the intein is at least one of: a split intein, a naturally split intein DnaE from *Nostoc punctiforme*, an Ssp from *Synechocystis* species, an Aha from *Aphanothece halophytica*, an Aov from *Aphanizomenon ovalisporum*, an Asp from *Anabaena* species, an Ava from *Anabaena variabilis*, a Cra(CS505) from *Cylindrospermopsis raciborskii*, a Csp(CCYO110) from *Cyanotilece* species, a Csp(PCC8801) from *Cyanothece* species, a Cwa from *Crocosphaera watsonii*, a Maer (NIES843) from *Microcystis aeruginosa*, a Mcht (PCC7420)-2 from *Microcoleus chthonoplastes*, an Oli from *Oscillatoria limnetica*, a Sel (PC7942) from *Synechococcus elongates*, an Ssp (PCC7002) from *Synechococcus* species, a Tel from *Thernlosynechococcus elongates*, a Ter-3 from *Trichodesmium erythraeum*, or a Tvu from *Thernlosynechococcus vulcanus*.

2. The method of claim 1, wherein the intein C-fragment comprises the amino acid sequence of SEQ ID NO: 37.

3. The method of claim 1, wherein the purification tag is at least one of: located at an intein split junction, which is at the C-terminus of the intein N-fragment; or is an affinity tag selected from at least one of a chitin-binding domain (CBD), a 6×Histidine, a maltose binding domain (MBP), a glutathione S-transferase (GST), is an elastin-like peptide, or SEQ ID NO: 38.

4. The method of claim 1, wherein the intein N-fragment comprises the amino acid sequence of SEQ ID NO: 39; or the second fusion protein comprises a sequence selected from a group consisting of SEQ ID NO: 4, 10, 24, and combinations thereof.

5. The method of claim 1, wherein the purification tag is defined further as a precipitation tag and the method further comprises:
   precipitating the complex;
   washing the complex;
   solubilizing the complex; and
   inducing intein cleavage, wherein the steps of precipitating the complex or washing the complex optionally comprise contacting the complex with one or more cleavage inhibitors.

6. The method of claim 1, wherein the purification tag is an affinity tag and the method further comprises:
   binding the complex to an affinity resin capable of binding the affinity tag;
   washing the complex with a washing buffer before the cleavage step; and
   inducing intein cleavage, wherein the steps of binding the complex or washing the complex optionally comprise contacting the complex with one or more cleavage inhibitors.

7. The method of claim 6, wherein inducing intein cleavage comprises contacting the complex with one or more reducing agents or chelating agents, and wherein the one or more chelating agents are selected from at least one of ethyleneglycolaminoethylestertetraacetic acid (EGTA), diethylenetriaminepentaacetic acid (DTPA), dipicolinic acid (DPA), or nitrilotriacetic acid (NTA).

8. The method of claim 1, further comprising the step of incubating the complex with a first washing buffer before inducing cleavage, wherein the washing buffer inhibits cleavage, or comprises a cleavage inhibitor selected from at least one of $Zn^{2+}$, $Cu^2$, $Mg^{2+}$, $Co^{2+}$, $Mn^{2+}$, or $Fe^{2+}$.

9. The method of claim 1, further comprising the step of washing the complex with a first washing buffer before inducing cleavage, wherein the washing buffer comprises a cleavage inhibitor that inhibits the C-terminal cleavage reaction.

10. The method of claim 1, wherein inducing the C-terminal protein cleavage comprises at least one of inducing a thio-induced C-terminal cleavage; or inducing a C-terminal protein cleavage comprises inducing a thio-induced C-terminal cleavage in the presence of a cleavage inducer selected from at least one of DTT, $Zn^{2+}$ chelating agents, trialkylphosphine, tris(2-carboxyethyl)phosphine (TCEP), 2-mercaptoethanol, cysteine, and combinations thereof; inducing a C-terminal protein cleavage comprises inducing intein cleavage by chelating a cleavage inhibitor using chelating agents.

11. The method of claim 1, wherein the purification tag is a precipitation tag, wherein the method further comprises:
   precipitating the complex, wherein a precipitated complex is formed; and
   wherein separating the POI from the complex comprises solubilizing the precipitated complex, wherein a solubilized complex is formed; and
   separating the POI from the solubilized complex, wherein the purification tag is optionally an affinity tag and the method further comprises binding the complex to an affinity resin and
   wherein separating the POI from the complex comprises separating the POI from the affinity resin to which the complex is bound.

12. The method of claim 1, further comprising regenerating the second fusion protein by dissociating the intein C-fragment from the second fusion protein.

13. The method of claim 1, wherein the POI is selected from a bioactive peptide, an enzyme, an enzyme inhibitor, an enzymatic catalytic site, a DNA-binding protein, an isolated protein domain, a ligand for receptors, a receptor, a growth factor, a cytokine, a structural protein, an antibody, an antibody fragment, an epitope, an epitope-binding region, an antigen, an allergen, and contiguous or overlapping fragments of a protein sequence of interest.

14. The method of claim 1, wherein the purification tag is an affinity tag and the method further comprises:
   binding the complex to an affinity resin before inducing the C-terminal protein cleavage; and
   regenerating the affinity resin by dissociating the intein C-fragment from the second fusion protein, wherein the affinity resin optionally comprises Chitin beads, Nickel resin, amylose resin, glutathione, and combinations thereof; or the purification tag is a precipitation tag that mediates precipitation of the second fusion protein, and wherein the complex is precipitated.

15. The method of claim 1, further comprising regenerating the second fusion protein by dissociating the intein C-fragment from the second fusion protein and again contacting the regenerated second fusion protein with the first fusion protein.

* * * * *